(12) United States Patent
Song et al.

(10) Patent No.: US 7,479,479 B2
(45) Date of Patent: Jan. 20, 2009

(54) CNGH0010 SPECIFIC POLYNUCLEOTIDES, POLYPEPTIDES, ANTIBODIES, COMPOSITIONS, METHODS AND USES

(75) Inventors: Xiao-yu R. Song, West Chester, PA (US); Chong Huang, Paoli, PA (US); Keying Ma, West Chester, PA (US); Bailin Liang, Gilbertsville, PA (US); Michael Naso, Philadelphia, PA (US)

(73) Assignee: Centocor, Inc., Malvern, PA (US)

( * ) Notice: Subject to any disclaimer, the term of this patent is extended or adjusted under 35 U.S.C. 154(b) by 17 days.

(21) Appl. No.: 11/680,113

(22) Filed: Feb. 28, 2007

(65) Prior Publication Data

US 2008/0044422 A1 Feb. 21, 2008

Related U.S. Application Data

(63) Continuation-in-part of application No. 10/835,904, filed on Apr. 30, 2004, now Pat. No. 7,326,687.

(60) Provisional application No. 60/466,573, filed on Apr. 30, 2003, provisional application No. 60/777,740, filed on Feb. 28, 2006.

(51) Int. Cl.
*C07K 14/00* (2006.01)
(52) U.S. Cl. .......................................... 514/2; 530/300
(58) Field of Classification Search ........................ None
See application file for complete search history.

(56) References Cited

FOREIGN PATENT DOCUMENTS

| WO | WO 99/55721 | 11/1999 |
|---|---|---|
| WO | WO 00/61623 | 10/2000 |
| WO | WO 02/08288 A2 | 1/2002 |

OTHER PUBLICATIONS

Strausberg, et al., "Generation and initial analysis of more than 15,000 full-length human and mouse cDNA sequences," *Proceedings of the National Academy of Science*, 99(26): 16899-16903 (2002).
Matsui, et al., "Identification of novel keratinocyte-secreted peptides dermokine-α/-β and a new stratified epithelium-secreted protein gene complex on human chromosome 19q13.1," Genomics, 84: 384-397 (2004).
Moffatt, et al., "Identification of a conserved cluster of skin-specific genes encoding secreted proteins," Gene, 334: 123-131 (2004).

GenBank Accession No. AA873028 (Mar. 1998).
GenBank Accession No. AC002389 (Jul. 1997).
GenBank Accession No. AD001502 (Apr. 1997).
GenBank Accession No. AF086315 (Aug. 1998).
GenBank Accession No. BC004493 (Jul. 2004).
GenBank Accession No. BC011886 (Jul. 2004).
GenBank Accession No. BC035311 (Aug. 2006).
GenBank Accession No. NM_033317 (Jun. 2007).
GenBank Accession No. AY358412 (Oct. 2003).
GenBank Accession No. AK096215 (Sep. 2006).
GenBank Accession No. AL832080 (May 2003).
GenBank Accession No. AC138125 (Dec. 2002).
Derwent Accession No. ADH98933 (Apr. 2004).
Derwent Accession No. ADII 1268 (Apr. 2004).
Derwent Accession No. ADH99244 (Apr. 2004).
Derwent Accession No. AAF54238 (Apr. 2001).
Derwent Accession No. AAA37036 (Aug. 2000).
Derwent Accession No. AAH23810 (Jul. 2001).
Derwent Accession No. AAZ43803 (Mar. 2000).
Derwent Accession No. ADE28278 (Jan. 2004).
Derwent Accession No. AAZ80280 (Apr. 2000).
Derwent Accession No. AAF97894 (Jun. 2001).
Derwent Accession No. AAS02641 (Jul. 2001).
PCT International Search Report dated Jan. 31, 2006.
Supplementary Partial European Search Report dated Jun. 13, 2007.

*Primary Examiner*—Karen Cochrane Carlson
(74) *Attorney, Agent, or Firm*—Eric A. Dichter

(57) ABSTRACT

Novel polypeptides (CNGH0010) and antibodies, including specified portions or variants, specific for at least one such CNGH0010 polypeptide, variant, or fragment thereof, as well as nucleic acids encoding such CNGH0010 polypeptides and antibodies, complementary nucleic acids, vectors, host cells, and methods of making and using thereof, are useful for therapeutic and diagnostic formulations, administration and devices. The aforesaid polypeptides can be used to generate human, primate, rodent, mammalian, chimeric, humanized and/or CDR-grafted anti-CNGH0010 antibodies. The CNGH0010 polypeptides and antibodies are used in modulating or treating at least one CNGH0010-related disease in a cell, tissue, organ, animal, or patient. Such diseases may include, but are not limited to, psoriasis, rheumatoid arthritis, emphysema, asthma, diabetes, autoimmune thyroiditis, inflammatory bowel diseases, including Crohn's disease and ulcerative colitis, different types of dermatitis including allergic dermatitis, contact dermatitis, actinic keratosis, wound healing, scar formation, various renal diseases, various respiratory diseases, various diseases of reproductive organs, such as endometriosis, melanoma, squamous cell carcinoma, ovarian cancer, breast cancer, lung cancer, colon cancer, prostate cancer, renal cell carcinoma, Grave's diseases and other inflammatory and hyperproliferative diseases.

10 Claims, 10 Drawing Sheets

Oligo pair specific for: 10.1 10.2 10.3 10.4 10.5

SELDI Mass spectrometry of CNGH00010.2 protein

SEQUENCE LISTING

```
<160> NUMBER OF SEQ ID NOS: 41

<210> SEQ ID NO 1
<211> LENGTH: 16356
<212> TYPE: DNA
<213> ORGANISM: Homo sapiens
<220> FEATURE:
<221> NAME/KEY: exon
<222> LOCATION: (101)..(526)
<223> OTHER INFORMATION: exon 1
<220> FEATURE:
<221> NAME/KEY: exon
<222> LOCATION: (786)..(986)
<223> OTHER INFORMATION: exon 2
<220> FEATURE:
<221> NAME/KEY: exon
<222> LOCATION: (1099)..(1155)
<223> OTHER INFORMATION: exon 3
<220> FEATURE:
<221> NAME/KEY: exon
<222> LOCATION: (1763)..(1813)
<223> OTHER INFORMATION: exon 4
<220> FEATURE:
<221> NAME/KEY: exon
<222> LOCATION: (1983)..(2165)
<223> OTHER INFORMATION: exon 5
<220> FEATURE:
<221> NAME/KEY: exon
<222> LOCATION: (2936)..(2980)
<223> OTHER INFORMATION: exon 6
<220> FEATURE:
<221> NAME/KEY: exon
<222> LOCATION: (3149)..(3205)
<223> OTHER INFORMATION: exon 7
<220> FEATURE:
<221> NAME/KEY: exon
```

```
<222> LOCATION: (3324)..(3392)
<223> OTHER INFORMATION: exon 8
<220> FEATURE:
<221> NAME/KEY: exon
<222> LOCATION: (3615)..(3665)
<223> OTHER INFORMATION: exon 9
<220> FEATURE:
<221> NAME/KEY: exon
<222> LOCATION: (5336)..(5371)
<223> OTHER INFORMATION: exon 10
<220> FEATURE:
<221> NAME/KEY: exon
<222> LOCATION: (6065)..(6118)
<223> OTHER INFORMATION: exon 11
<220> FEATURE:
<221> NAME/KEY: exon
<222> LOCATION: (7391)..(7450)
<223> OTHER INFORMATION: exon 12
<220> FEATURE:
<221> NAME/KEY: exon
<222> LOCATION: (7590)..(7637)
<223> OTHER INFORMATION: exon 13
<220> FEATURE:
<221> NAME/KEY: exon
<222> LOCATION: (7811)..(7858)
<223> OTHER INFORMATION: exon 14
<220> FEATURE:
<221> NAME/KEY: exon
<222> LOCATION: (10129)..(10155)
<223> OTHER INFORMATION: exon 15
<220> FEATURE:
<221> NAME/KEY: exon
<222> LOCATION: (10690)..(10746)
<223> OTHER INFORMATION: exon 16
<220> FEATURE:
<221> NAME/KEY: exon
<222> LOCATION: (11393)..(11440)
<223> OTHER INFORMATION: exon 17
<220> FEATURE:
<221> NAME/KEY: exon
<222> LOCATION: (11679)..(11753)
<223> OTHER INFORMATION: exon 18
<220> FEATURE:
<221> NAME/KEY: exon
<222> LOCATION: (12996)..(13043)
<223> OTHER INFORMATION: exon 19
<220> FEATURE:
<221> NAME/KEY: exon
<222> LOCATION: (13157)..(13198)
<223> OTHER INFORMATION: exon 20
<220> FEATURE:
<221> NAME/KEY: exon
<222> LOCATION: (13547)..(13618)
<223> OTHER INFORMATION: exon 21
<220> FEATURE:
<221> NAME/KEY: exon
<222> LOCATION: (14679)..(14702)
<223> OTHER INFORMATION: exon 22
<220> FEATURE:
<221> NAME/KEY: exon
<222> LOCATION: (14813)..(14860)
<223> OTHER INFORMATION: exon 23
<220> FEATURE:
<221> NAME/KEY: 3'UTR
<222> LOCATION: (15895)..(15929)
<223> OTHER INFORMATION: exon 24
<220> FEATURE:
<221> NAME/KEY: 3'UTR
<222> LOCATION: (16038)..(16356)
<223> OTHER INFORMATION: exon 25

<400> SEQUENCE: 1
gaggaggaca gaggagggca cagagacgca gagcaagggc ggcaaggagg agaccctggt    60
gggaggaaga cactctggag agagaggggg ctgggcagag atg aag ttc cag ggg   115
                                           Met Lys Phe Gln Gly
                                           1               5
```

| | | |
|---|---|---|
| ccc ctg gcc tgc ctc ctg ctg gcc ctc tgc ctg ggc agt ggg gag gct<br>Pro Leu Ala Cys Leu Leu Leu Ala Leu Cys Leu Gly Ser Gly Glu Ala<br>10 15 20 | | 163 |
| ggc ccc ctg cag agc gga gag gaa agc act ggg aca aat att ggg gag<br>Gly Pro Leu Gln Ser Gly Glu Glu Ser Thr Gly Thr Asn Ile Gly Glu<br>25 30 35 | | 211 |
| gcc ctt gga cat ggc ctg gga gac gcc ctg agc gaa ggg gtg gga aag<br>Ala Leu Gly His Gly Leu Gly Asp Ala Leu Ser Glu Gly Val Gly Lys<br>40 45 50 | | 259 |
| gcc att ggc aaa gag gcc gga ggg gca gct ggc tct aaa gtc agt gag<br>Ala Ile Gly Lys Glu Ala Gly Gly Ala Ala Gly Ser Lys Val Ser Glu<br>55 60 65 | | 307 |
| gcc ctt ggc caa ggg acc aga gaa gca gtt ggc act gga gtc agg cag<br>Ala Leu Gly Gln Gly Thr Arg Glu Ala Val Gly Thr Gly Val Arg Gln<br>70 75 80 85 | | 355 |
| gtt cca ggc ttt ggc gta gca gat gct ttg ggc aac agg gtc ggg gaa<br>Val Pro Gly Phe Gly Val Ala Asp Ala Leu Gly Asn Arg Val Gly Glu<br>90 95 100 | | 403 |
| gca gcc cat gct ctg gga aac act ggg cac gag att ggc aga cag gca<br>Ala Ala His Ala Leu Gly Asn Thr Gly His Glu Ile Gly Arg Gln Ala<br>105 110 115 | | 451 |
| gaa gat gtc att cga cac gga gca gat gct gtc cgc ggc tcc tgg cag<br>Glu Asp Val Ile Arg His Gly Ala Asp Ala Val Arg Gly Ser Trp Gln<br>120 125 130 | | 499 |
| ggg gtg cct ggc cac aat ggt gct tgg gtgagtggct gtgggctgc<br>Gly Val Pro Gly His Asn Gly Ala Trp<br>135 140 | | 546 |
| atgtggaaat gggaggctgt gggctgctgg gctgagattc ttgggaaacg gttgaaagga | | 606 |
| tggatggatc tcttacttgc aggcttctgg ggcagcttcc ttctatgttc tgccccctc | | 666 |
| ctatgccacc ctggagtccc tctgcctgtc tctctcctgg tctctttatg atttgccctg | | 726 |
| gctcttctct accagggtca gagatggtcc cactaagtgc aggtatgttg ttcttgcag | | 785 |
| gaa act tct gga ggc cat ggc atc ttt ggc tct caa ggt ggc ctt gga<br>Glu Thr Ser Gly Gly His Gly Ile Phe Gly Ser Gln Gly Gly Leu Gly<br>145 150 155 | | 833 |
| ggc cag ggc cag ggc aat cct gga ggt ctg ggg act ccg tgg gtc cac<br>Gly Gln Gly Gln Gly Asn Pro Gly Gly Leu Gly Thr Pro Trp Val His<br>160 165 170 | | 881 |
| gga tac ccc gga aac tca gca ggc agc ttt gga atg aat cct cag gga<br>Gly Tyr Pro Gly Asn Ser Ala Gly Ser Phe Gly Met Asn Pro Gln Gly<br>175 180 185 190 | | 929 |
| gct ccc tgg ggt caa gga ggc aat gga ggg cca cca aac ttt ggg acc<br>Ala Pro Trp Gly Gln Gly Gly Asn Gly Gly Pro Pro Asn Phe Gly Thr<br>195 200 205 | | 977 |
| aac act cag gtaaagtcac cccagacct gctacctgcc acctccctcc<br>Asn Thr Gln | | 1026 |
| ctccaagccc acatgctccg cgtgcctccc tggtccctct ggatcctact ctcagtctca | | 1086 |
| ccctctctgc ag gga gct gtg gcc cag cct ggc tat ggt tca gtg aga gcc<br>Gly Ala Val Ala Gln Pro Gly Tyr Gly Ser Val Arg Ala<br>210 215 220 | | 1137 |
| agc aac cag aat gaa ggg gtaagaggaa ggggctggga acaaatgaag<br>Ser Asn Gln Asn Glu Gly<br>225 | | 1185 |
| aagccactgg gtgcaggcta cagagagctg gggaaagaca aagaggaaag caagatgggg | | 1245 |
| gagtggaggg attggggtga gaggaagaga tggggctggg cgaggtggct cacacctgta | | 1305 |
| atcccagcac tttgggaggc caaggcacgt ggatcacctg aggtcaggag ttcaagacca | | 1365 |

-continued

```
gcctggtcaa catggtgaaa ccctgtcttc actaaaaata caaaaatcag ccggtcatag    1425
tggcatgcgc ctgtaattgc agccacttgg gaggcggagg caggagaatc acttgaacct    1485
gggagatgga ggttgcagtg agccgagatc gcatcactgc actccagcct gagcaacaga    1545
gtgagaccct gtctcaaaaa aaaaaaaaaa aaaaaagga ggaagagacg ggcctgggcc    1605
tggggaggag gcagatggga agggaggtg ggagaaacac attaggagaa aggaagccaa     1665
gccccaaaga atgggagagg cctggcctgt gtccatggcc gaggccaacg tctccaaact    1725
caccgtcccc aaactcacca tcccttccc tcgacag tgc acg aat ccc cca cca       1780
                                        Cys Thr Asn Pro Pro Pro
                                                    230 tct ggc tca ggt gga ggc tcc agc aac tct ggg gtgagtggag aggggcaacc    1833
Ser Gly Ser Gly Gly Gly Ser Ser Asn Ser Gly
235                 240                 245 caggagttgt gcaccaggag gaaatggaga agttctgctc cccttagact gggcatcatg    1893
gaatatggcc tgggtggaga gggagggagg aggggcccgt cttggtgctc tgtctttaat    1953
cccagccctg ctcccttcct gccctcag gga ggc agc ggc tca cag tcg ggc       2006
                                 Gly Gly Ser Gly Ser Gln Ser Gly
                                                         250 agc agt ggc agt ggc agc aat ggt gac aac aac aat ggc agc agc agt      2054
Ser Ser Gly Ser Gly Ser Asn Gly Asp Asn Asn Asn Gly Ser Ser Ser
    255                 260                 265 ggt ggc agc agc agt ggc agc agc agt ggc ggc agc agt ggc ggc agc      2102
Gly Gly Ser Ser Ser Gly Ser Ser Ser Gly Gly Ser Ser Gly Gly Ser
270                 275                 280                 285 agt ggt ggc agc agt ggc aac agt ggt ggc agc aga ggt gac agc ggc      2150
Ser Gly Gly Ser Ser Gly Asn Ser Gly Gly Ser Arg Gly Asp Ser Gly
                290                 295                 300 agt gag tcc tcc tgg gtgagtttgg cacctctgtg gaaggctgag atggggtgag      2205
Ser Glu Ser Ser Trp
            305 gccctagtgg tccctgccgg gagagggctc caagtttctc tgaaagctgc cgctgcccga    2265 ggatgggcgg cctcgctgat agtcgtcacc ctgaggctcc ctcagcctcc tgttccccac    2325 ccatgctgtg cccctgatgc gcgcactatc gtttctgcca gagccacccc actgcttctg    2385 actctgtatc cctatttcc actctgtgat ggtggggacg ttatcccgcc tgtctaagct     2445 cttgcagtca agtccacttg gcaagtctca ggagaccgtg gggtggcgga gaaagagggg    2505 gacatgggag aatatgacac ttgtctggga agctcccagg agaatggggg caggactgtg    2565 atccgggaga cctacggacg ctgacagagc gacggtgcag acgacattca cacatggggc    2625 ccctgcacga tgggtgtgag ggcaggaagg ggcgctgtga ccccgcagct gccaccccag    2685 ggccccgggc ctcactgact ccagagccgg cagtctctcc agcctcctgg tcaatggcct    2745 gtccaacccc ttggctgacg gcctctccca tcccgtgtct tggagtcgag ctggagaggg    2805 agccacatct ggcttcctcg ggggtcggga aaagtgtcag acaggaggag gtgcgtggac    2865 acaataagcc gaataacctg agctgctctc atgcgccgct ccccgtatga tcctcctctc    2925 ccccatctag ggc agt tct ggg aat ggt gac caa ggc agc tac ggc cgc       2974
              Gly Ser Ser Gly Asn Gly Asp Gln Gly Ser Tyr Gly Arg
                                310                 315 tcc cag gtgagggctc tagggtccct tccacttgct gccccctggt ggcaggatcg       3030
Ser Gln
320 cggctactgc gcggccgggc tcagggggtt cccaccccg gcctgcggtg ggcagcagct     3090 caggttctcc aaatcattgc gtagttccga ataccctcgg ccacacctgg ccttctcc     3148
```

```
atg ctc gga ata act tcc tgc agc gac caa cag gct aaa gag ggg gaa      3196
Met Leu Gly Ile Thr Ser Cys Ser Asp Gln Gln Ala Lys Glu Gly Glu
            325                 330                 335 ggt ctg gag gttggaaaga ggactggaat ctgattgggg ttccaacaaa              3245
Gly Leu Glu
        340 tctgtaacac cgctgggaac gactgggtcc cctttaggtc ctttaggaca gcgtttgaaa    3305 tcttgctttc ccctgcag gga tcc agc acc ggc tcc tcc tcc ggc aac cac     3356
                    Gly Ser Ser Thr Gly Ser Ser Ser Gly Asn His
                                    345                 350 ggt ggg agc ggc gga gga aat gga cat aaa ccc ggg gtgagtggct           3402
Gly Gly Ser Gly Gly Gly Asn Gly His Lys Pro Gly
                355                 360 ggcgtgaatc tcccaccaac cgcgggaagg aaaaggagag cagctggttt cactcgcagg    3462
atcggggagc caaggctccg cggagatggg gctggatggc cgcggaggtg gagcggaagc    3522
ggctcgcccc agggttaaaa tgctgccatt ttggggctgg gactggtctg ggaggggact    3582
gagggaaagt ctccccttc tctccccggc ag tgt gaa aag cca ggg aat gaa       3635
                                   Cys Glu Lys Pro Gly Asn Glu
                                                365             370 gcc cgc ggg agc ggg gaa tct ggg att cag gtgagagcca aagtctctta        3685
Ala Arg Gly Ser Gly Glu Ser Gly Ile Gln
            375                 380 agtctcctgg ggactgcagt tcctgcccag gactgtgccc actcctccta actcaactct    3745
gctcaacccc ctcctgcctt gtctgcaggg aactgactat tcggcagaa gaaaccaaat    3805 gcactcctaa aaatgctaac gatttccaaa gtactaatta attgcaaatc ttgctgtgat    3865
atacctcacc ttataccaca gatggggctg ggagaaattc catgtaaacc ggtccttta    3925 gaagcacaat tgtcttaaat gtcctctatc cagccgggga acagactgtg gtgaactctg    3985
ggggattcag agtgctttgg aaaaacattc cccccagtta tgctggaaat gtgggctta    4045 tgtcagcacc tgtggtgctg agagttagtg tcacggagat cttgtgaaag tgcaggttgc    4105
tctaacaggg ctgggtgggg ctgagcctgt tagccgcgtt gctaacaagc tcctgggtga    4165
ggcgttggtg ggaaaggacc cacgtggcca ggggcaaggc cagaccggag gtgctgggc    4225 tgagtagaga catctctttt tagataatct atgaggggata ctaaccttt atgggaacaa    4285 actggttttt ttaaaaaaaa atttcttccc atttgtaacc ctctttctag tttgtgtttt    4345
tttccttttt gagatggagt cccgctctgt tacccaggct ggagggcagt ggtgcgatct    4405
gagctcactg gaaactccac ctcctgggtt caagcgattc tcttacctca gcctcccgag    4465
tagctgggat tacagacgcc agccaccacc tctggctaat ttttttttgt atttttagta    4525
gagatggggt ttcaccatgt tggccagct ggtctcaaac tcctgatctc aggtgatctg    4585
tccgcctctg cctctcaaag tgctgggatt acaggcatga gctactgcac tcggactttt    4645 ctagttttt aatataccctc agttttaagt atataagtag tcaaaagca gccatctttt    4705 cctctatggt ttttgctctt ggtgtaccgc tttaaggtaa tttcttcta gcactatgca    4765 tactcctgca atttcacttt tcagtttaa ctgggatgca tctggacttt gttttcctat    4825
atgctgtcta gtcccacccc tccatctaac cagacttacc ctacgctttg tatccgagct    4885
gtgtcctcct ttatgagggg aaaactggtt aaaaacagag aggaggaaat tgatgagcta    4945
gaactaaaat tttcccccaa aatacttcac tgatattccc attccatgt attcaatcac    5005 ttcaaccact gatttaaaat gcctcttgta aataccttag tattttgggg agtttctggg    5065
```

```
aattctgtcg gacaggactg ctttatttat ggtagcttta gagtatgtta ctatctacct      5125
cttatcttca cttaccattt atcttttcca gtgttttctt acctattctt aaactttcat      5185
tctcctaaaa aaatgtcagt gtttggacca gttccaaaag agagtgccat taggattctt      5245
agaggaatca tattaaatca atacattaat tttcgggggt ggcctcagga tcttcagcag      5305
gggtctgtgt ttctttgtct caccctgcag ggc ttc aga gga cag gga gtt tcc      5359
                                   Gly Phe Arg Gly Gln Gly Val Ser
                                                        385 agc aac atg agg gtaagaggat ggtagatgtg gggtcagaga ctgtgccggt             5411
Ser Asn Met Arg
        390 agtaagtggg gtagaggtct gttctccagg agcaatactg gcagacaggt ggtcccacat      5471 ccctgccagg tctacctgag agctctggga acgaggaagt actgatgggt ctggccatgt      5531 ttcacagcag ataaagcagg actccagagg agcccacctc tcccttaaga ggggaccagc      5591 cagtctactc tatgccgcct cagccccac tggctctcca gctagcatct cctttttta       5651 ctaatgccaa tcagcccaga cagggtcctt cagtttgaat caatttagtg taacagcctg      5711 gcccactcca gctccaaagc caggggagaa ttcggatgct tgctggcaa agccctccct       5771 gatggatttt gggcggcttg cagaaatgaa cataaacaga gatggcgatg ttatctatgg      5831 acatcgtaag tgagcagcca cccgacccac aggagcttga aacgagatct cagggcagat      5891 ggaacttccc cgagagaagg acctcttttct caggcctctg ggaagtcctc tgtcatgctc     5951 atgtctcagt cccccgattc aggaatccct cgccgacacc ctgcttcctt gccctctcgt      6011 cccctgccc gcctgcctcc ccatcaactc ctctccgttt tctgtctccc tag gaa          6067
                                                         Glu ata agc aaa gag ggc aat cgc ctc ctt gga ggc tct gga gac aat tat        6115
Ile Ser Lys Glu Gly Asn Arg Leu Leu Gly Gly Ser Gly Asp Asn Tyr
    395                 400                 405 agg gtgagcctag gggcaggcag ggttggcttt aggagaaggg atggtgaagc              6168
Arg
410 atgctaagat cctgggaaaa gaaacaaaaa tatcagtttc ttcttgcaag ctgctctgaa      6228 tctgcgtcca gtgaccatca agagaccaaa acagggttct gggatcccca tctccatctt      6288 tggttcattc attccttcct tccttttgat ttggatcgga gccatgttac ttttgtaagg      6348 ggagaaaaca gataaaagta acagaagaat ggtcaagggg atttccatac ttagggaggc      6408 agtgttgaga aggagaaagt cactgagctt tgaggtagaa gatgaggttt cgaaagccag      6468 ctctggccag gcaccagcat aactgtaatc ccagcacttt gggaggctga ggtgtggga      6528 tcatttgagc ccagaagttt gagaccagcc tgagcaacgt aggaagaccc tgtctctact      6588 ttttaaaaag aaaataatag gccatgtgca gtggctcaca cctgtaatcc caggtagcta      6648 ggattacatg cctcagcctc ccaagtagct gggattacag gcatgtgcca ccatgcctga      6708 ctaattttgt attttagta gagatggggt ttcactatgt tggccaggct gttttcaaac       6768 tcctgacctc aggtgatcca cccacctcgg cctctcaaag tgctgggatt acaggcgtga      6828 cccacgatgc ccagcctcaa aaaaatttaa gatatatatt aaaatcacca ccagctctat      6888 catgtcatct gtatatcttc aggcaagtca gctaacctct ccgagcctga gcttcctcca      6948 gtaaaatgag gacagtgaaa cctgactcac gcagccttca gttactgtac agcttttccat    7008 gtcaccacca gaccaaggtg ttgtggagtc cagactctgg agacagatgc tgcataaggc      7068 atggtgcttg gcgtgccgtg ggactacacg ttagctaatc tcatttgctt gaggtgtttt      7128
```

```
ggggacagac caggatggag gcaagagtct gaatattgag attcagggga ctgggtgggg    7188
ttccatggga gcaatccatt ctaagaaagc tttcccaagt gaacttttg gtgctgtgta     7248
aggaagagaa ggcagcttta tagagaggag acaggaagc ctggaccgag gtggggatga    7308
agcaatccgg ggcaggttga caggtggcag gcatgatagg aagcataagc cttggacatc    7368
ggtcccccctt tccccaccc ag ggg caa ggg tcg agc tgg ggc agt gga gga    7420
                         Gly Gln Gly Ser Ser Trp Gly Ser Gly Gly
                                     415                 420
ggt gac gct gtt ggt gga gtc aat act gtg gtgagtggag gcaacactcc        7470
Gly Asp Ala Val Gly Gly Val Asn Thr Val
            425                 430
accttgggct gggaccatgg tgtcacacaa tcctcgcctc ccctcctgcc actcagatct    7530
cccgactctg gctcacaaag tgggttcttc tctcatccca tatctccttg gttccatag    7589
aac tct gag acg tct cct ggg atg ttt aac ttt gac act ttc tgg aag     7637
Asn Ser Glu Thr Ser Pro Gly Met Phe Asn Phe Asp Thr Phe Trp Lys
                435                 440                 445
gtgagttctg cgagatggct ctgttcactc gcatttggaa aaccaacccc tgcccttggc    7697
cccacagtct ggggtcctct ttctaaacca acagtcagca gtggcccttg acctctctcg    7757
gccaattacc ttatgactca atttggccat tcttctttt gtttcctcca tag aat       7813
                                                             Asn
ttt aaa tcc aag ctg ggt ttc atc aac tgg gat gcc ata aac aag         7858
Phe Lys Ser Lys Leu Gly Phe Ile Asn Trp Asp Ala Ile Asn Lys
    450                 455                 460
gtaagggctg acatcttcg tcggagaggg ctataggaa gaaagctaaa cctccgctct      7918
gtgagctggg gaaacagtga tgctggccac tgaggaagca tttaggccag tgctaaaaac    7978
aaaaactaaa cacactgggg gtggaggagg gaggacagag gagacctgaa agaggggga    8038
gaatctggag cagctgagat tgaggttgag cagaggggac gggcttcttt gctgtttcag    8098
catatagacc cgagcaggtc ctgaacctca ctttcccctt tgagatgggg aaggttaagg    8158
ggagagtaga ttgactccta gagggcacat ggaatgagga gtgaggtgga gctaagaggc    8218
cccaagagga agggcaccca gagaaaggaa ccagcactgg ccgagagcct caggggtgac    8278
aggcattagt ctctcccgca caaacaaaaa cacagctggg gcgcagaacc cctccctcct    8338
tcctcccctgc ctacccttcc gtcttgcagg ggaaccctg gccaggctgc tttgatacct    8398
gagtagcaca ggcacctcta gagtagaggg ggctggagtg aagggagggg gaggaaggac    8458
aggtggacaa cccatgcaga cacaccccg gcagaagctg cgattcgtga ttggaggatg    8518
ggttttgag acactctatt ttttttttt tttaagaata tgaattaatt gtcaaagttt     8578
aaacatggag agacttcaca taatgatttg gatttctggt ttctttcaaa aactttggta    8638
acactgggtt ccatttccat ggggtggggt taggctagag ctgagaaaca gctgctgctt    8698
ggcccaggtg gggggtgttg ggaatgggtg gggggtcac tccctagtgg ccagactgtc    8758
cctacctgtc acagtcattt tagccacctg actggcccct gtgagcagtg gagtttctgg    8818
cctttaatgt aaaagagaga agactgggct caggaaaatc taagtctgac cttttaggaa    8878
ggagattgag gagacaggag agtacagatg ttcccaccca gctacagtgg attcatgttc    8938
tctgtttctt ttcttttttc ttttctttc tttctttctt ttgttttttt tttttttggt    8998
gagacggagt ctcgctctgt cacccaggtt ggagtgtagt ggttcgatct cagctcaatg    9058
cagcctctgc ctcctgggtt caaaatgatt ctcctgcctc agccgctcca gtagctgagt    9118
ttacaggtgc ccgccaccac acccgggtaa tgtttgtatt tttagtagag atgggctttc    9178
```

```
actatgttgg ccaggctggt ctcgaactcc tgacctccag tgatctgccc accttggctt   9238
cccaaaatgt tgggattaca ggcatgagtc actgcatctg gcctctctgt ttcacagaga   9298
acggtttctg gtaggagcaa gactctttcc tgggtcacag gaacttaggg tctgatggg    9358
agagccgggg cacatacaga cacttcccag agagccagga tagacaccct gccagttttg   9418
cccatctagg gcggcagtcg agggagtgat cgcagtgagg caggatccat ctgggccagc   9478
tcctcaaggg gcagatctcc tagaaagcag ggcagggcag aggtgggcag gggagagaat   9538
ggagccccat tcttcacagt gggGtgaggg agctgaggac ttcagccaga gtgaggaggg   9598
agcagagggg aacgcagtgt aatgttcctg acgatgcagg gggttcttaa gcccaagcca   9658
ggatatctgg gtttgtttgg atagcagtgg tgggcaaaaa ggtccctgta ggtttctgga   9718
gcagggtct  cttataccct tgtgctggct cacaatgccc tggaattcct atttctcaag   9778
ctctctctta gaacctattt ctggccaggc gcggtggctc atgcctgtaa tcctagcact   9838
ttgggaggcc gaggctggca gatcacttga ggtcaggagt ctgaaaccag cctggccaat   9898
gtggtgaaac cccatctcta ctaaaaatac aaaaattagc caggcgtggt ggtgtgcgcc   9958
tgtagtccca gctacttggg aggctgaggc aggagaatcg cttgaacctg ggaagcggag  10018
gttgcggtga gctgatatcg tgccactgca ctccagcctg ggcgacagag cgagactcca  10078
tctcaaaaaa aaaaaaaaaa aaacaaaaaa aaacctgttt ctttgcccag gac cag    10134
                                                         Asp Gln aga agc tct cgc atc ccg tga cctccagaca aggagccacc agattggatg        10185
Arg Ser Ser Arg Ile Pro
465                 470 ggagcccca cactccctcc ttaaaacacc accctctcat cactaatctc agcccttgcc   10245
cttgaaataa accttagctg ccccacactc ctggcctctg ctccttttctt acgtctccgc  10305
tgttatccag ggtggtgtgg aaggggtggc tgcagcccca cagcttcggg aaacgggctg   10365
gaggaggccc ggcaggtgga aagggacac  tctgaggcag gtcctagtct tgaggttttg   10425
ctagaattag gttctgctgg aggctgggga acttgggata gaaaacattg tatgctctgg   10485
gacagggaga gttggttagt gcctctctct tccctgtgt  ttcccaaaat ggtttcctgg   10545
tgtccctaaa gactctcagc tcctcccatc cccaacctta gtcacaatga cattctgaag   10605
gttgagatag gcagtagca  ggaggagggg tgggtgagtg ggcccaggct ctctgctaac   10665
ctgctccccg cctttcatcc acag aac cag gtc ccg ccc ccc agc acc cga    10716
                           Asn Gln Val Pro Pro Pro Ser Thr Arg
                                              475 gcc ctc ctc tac ttc agc cga ctc tgg gag gtaggagaat tcttgctgtt      10766
Ala Leu Leu Tyr Phe Ser Arg Leu Trp Glu
480                 485 tgaagaactg ggggcctggc cctcctgact ctccccaagc ctccctcaag gcagccaccc  10826
tctgctccaa ccacctgttt caaaactccc ccctttttt  ttttgagac  agagtctcgc  10886
tctatcaccc aggctgaagt acagtggcac tatctcggct cactgcaaac tcctgcctcc  10946
tgggttcacg ccattctcct gcctcagcct cccgagtagc tgggactaca ggcgcctgcc  11006
accgtgcccg gctaatttt  ttttgtatt  tttagtagag acagggttta ccatgtta    11066
gccaggatag tctcaatctc ctgacctcgt gatccacctg cctcggcctc ccaaaatgct  11126
gggattacag gcgtgagcca ccgcgcccag ccaactcccc tcttcatttt tgagacagc   11186
tcatccaaat cttatcacca aatcttatca ccaataccat ctcaagtgct gacaccctca  11246
atctcccacg tgcttacctt cctccaaccc caagccacac ccaaaagctc cttcctaccc  11306
```

```
gagatctgga atccccccaa tttgctgcat agaccacccc gtgggttctg cctcccggc       11366 ccactctgcc ctccttctcc ctgcag gat ttc aaa cag aac act cct ttc ctc       11419
               Asp Phe Lys Gln Asn Thr Pro Phe Leu
                490                 495 aac tgg aaa gca att att gag gtaagggggg caggacttct cagctctggg           11470
Asn Trp Lys Ala Ile Ile Glu
    500             505 acacagggtt cggggccctg gcgagccgc tgacccaggt gtctgtccca gtttcttccc       11530
ctcccttccc actttcccag ctttgtgca atcccgagtg ggggcggggt gagagggaga       11590
agccgtgagt cactgaggag cagggtggga ggacctccct agcataaaag ccgaggccga      11650
gggctggggc ctccacaagc acatgaac atg aag ccg gcc act gcc tct gct         11702
                                Met Lys Pro Ala Thr Ala Ser Ala
                                                    510 ctg ctc ctg ctc ctg ctg ggc ctg gcc tgg acc cag ggg agc cac ggc        11750
Leu Leu Leu Leu Leu Leu Gly Leu Ala Trp Thr Gln Gly Ser His Gly
    515                 520                 525 tgg gtgggtaccg cagggtgcac aggtgcgggg agatcgtatt gaggggaaga             11803
Trp
530 aggggcctag gctgcggcat ggggaggaca gctgaggtgg aacgggaggg cggtgtgcag      11863 gggtcaggtc cctgtctagt ggaggcagct gctgagggtc tgaagacctg gtcaggag       11923 gatggggaga acctctgggc ggtgccaaag accacactcc aattctgcat ggccagtagc      11983 ctttgagaaa caggacccgt gggcactgag acaaaggctg cctgctcccg tgtctacgtg      12043 tgccaagtat atgaggctgg acaggtgggg ccctgcaaag gggaggtcg aggcgctcca       12103 gctaagtgca gtcatgcatg catgtgtgaa cagggtggcg tgttgtctga tgtttcacga     12163 agaaccagga tgctgatctc taactgtaac taatttaatt tttaagtaga ccaagcaaaa     12223 aatatctgga ggcccatggt caaccagttt gtgacctcag ggttagggct tgcagtgggg    12283 tttaggttca aggtcaggta tggataaggc agaattaatg ctggagtcag gacttcactg   12343 tcactctgtg tgtgtgtgtg gcagggcgga cggtccaagt ggagaagccg tgatggcagg    12403 aactgaactt cttttcaacg cttagagttt ctcctcttgc gctgggctg gggggggtgt     12463 ccggtgcatc tgcagtgtct taagttgctt tatctgtttt cttgtatttc tcttctttg     12523 cttcctgtgg tccagagcta acctaagcac gcagcttctg cagataacaa cccctccttc    12583 aagcaccctg tggggcatgg cgtcggtgtg cagggactaa gggcctacgg gcatagcagc   12643 aggacttggt gcaggcagaa ggtgggctgg gctgcagtgc ctgcgtctgc cccagaggag    12703 cctgcatggc tgcagctcac ttgttctagc tcagtcttag gctggggctg ccaactctcc    12763 cacggcatgg gtggggaagg tgttgccaaa cctggttctc tccctggctc ccaatgctga    12823 gtgtggatat ctgtcttcta tctatctggg ccatcagctc ctccaggctc actgccttct    12883 ctataggtag cacgtggaaa ggggtgggt gagggagaaa ctgggctct gaaagcccgg     12943 caatgcccgc acgactgcgg aggcacgaac tgtggcccct tcttcctttc ag ggt gcg    13001
                                                          Gly Ala gac gcg tca tca ctg cag aaa cgt gca ggc aga gac gat cag                13043
Asp Ala Ser Ser Leu Gln Lys Arg Ala Gly Arg Asp Asp Gln
535                 540                 545 gtgagtctct gtcctcaagt taccctgcag ggcccttggt ccccccttggc cttgctcccg    13103 ggtctgggca atctgaaatt ctctttcact cctccattca atggctttct cag ccg        13159
                                                             Pro ggt gca gga tgg cag gag gtg gca gct gta act tcc aag gtgagacatc        13208
```

```
Gly Ala Gly Trp Gln Glu Val Ala Ala Val Thr Ser Lys
    550                 555                 560 taccatggac ccgctgggtt acgtcctggc acttcttttc ttggtctcct accctcacct    13268
cccaagtaac acttgaagag ttggcagagg tcttgagggc aggaggagga gtaggaggag    13328
gaggcggcgg ccatttgggc taggacagta aaggcaggtg agggtggggg ccctggctgg    13388
ctggaggaga ttgtataaaa gaaaacacgt gacacaagga gggagcagg caggtgtttt     13448 aggaaaggtc tggtccaggc aggaaggtgg gatgtttatt ccagagcaaa atggccttcg    13508
tccgtctgtt ctaaccgcca tgcccacttc ttccacag aac tac aat tac aac cag   13564
                                          Asn Tyr Asn Tyr Asn Gln
                                                              565 cat gcg tat ccc act gcc tat ggt ggg aag tac tca gtc aag acc cct      13612
His Ala Tyr Pro Thr Ala Tyr Gly Gly Lys Tyr Ser Val Lys Thr Pro
        570                 575                 580 gca aag gtgagaccgg caaccaccct gtcttcccgc tgggggctct gcatgaggga       13668
Ala Lys tggggagaga ggctttcact gccggggtcc tctcggttgg ttgccggagg ccggatcccg    13728
ctctctttga gtccaggcct ccccacccct ttgcaaggga gactcgggtt ccctgagaca    13788
gtttggaagt ggagggcagg agggttcaat gcgcctcaca cccacccagt cagaaaaggt    13848
taaaaaggag cagcagcagc aacagagaaa actgagaacc aacaccctct ccaagaagaa    13908
tataggcttt aaaaaatcat gacacctgca aaacacgcaa gcagctcttc ctcacaggtt    13968
ccctctctgt ggaccttttt ttgcggggga agatggaatg gagggcgagg aaagcagact    14028
agcacttagg ggaggccggc ctgtggatgc ctggttggcg gtgaaatgaa tgctttattc    14088
cacaaaggaa atgaaaagaa aaaatacgtg agaatttggt tttattccgt tgcaaagaag    14148
gcaatctcat aacatcagta atgaatatg ctaagtacaa atttggctga caaagcaaca     14208
gcaggctgtg tatttccatc tctcatgaca ataaagtccc cgcccttggg gagaggacct    14268
tccactgagg gacgagaaac tacaggctgg tgagaggagg gacatgcagc ttctactgcc    14328
tgtggcttcc actctgctga gttatctgtg gcttccactc tgccgggtta tctgtggtca    14388
gtgtctccct acctggcagg ccaaagcgag gcctatgctc ttttgacccc cttggtcagt    14448
acgtgcccag gaaccatgtt caatatcatc ttggatcaag tgcactcagg atgataaacg    14508
tgctgtgaaa ccaactccac agcctgaatg tccacagtca gactggaaaa ccttggtgat    14568
agccctggtg tgagcctgcc cttgctgctg ggccttcat gagcgtggag gccatggcag     14628
agtacaggga ggccatgacc ccacatcact ttcctttgat cttttttgcag ggg gga     14684
                                                          Gly Gly
                                                              585 gtc tca cct tct tcc tcg gtgagtatgg gggcctgatc ttcatctggc              14732
Val Ser Pro Ser Ser Ser
            590 tggagagaga aggggcctga ggccagaggg tatggaaggg accctgtggt ggccactcag    14792 actttctctt tttctggcag gct tcc cgg gtg caa cct ggc ctg ctg cag tgg    14845
                       Ala Ser Arg Val Gln Pro Gly Leu Leu Gln Trp
                                595                 600 gtg aag ttt tgg tag gtgagtgtca gagtgagccg acccaggcca catcctggca     14900
Val Lys Phe Trp
    605 gtggaggcac agtcacccgg ggcagggcca ggatcttggt atatcctcag atctcagtgg    14960 gcagcgacat gaagtcaggt atgctctggg tgcgtgctct aaaggtgata aggaagaggg    15020 gacctcatgg tggggtgtgg agaaagaccc ataataaagt gatctaggc tgggtgcagt     15080
```

```
ggctcatgcc tgtaatctct gtgctttggg aggctggggt gggaggatca cttgagtctg    15140
ggagtttgag accagactgg gcaatatagc aagaccccat ctctaaaaga acaaaacaaa    15200
acaaaccaaa acaaaacaaa ccattccagc ctgggaaaca tggcaaaacc ccgtctacta    15260
aaaatacaaa aaattagcca ggtgaggtgg tgcatgattg taatcccagc tactctggag    15320
gctgaggtgg gagaatcacc tgagcttggg aggttgaggc tgctgcgaac tgcgattgca    15380
ccgctgcact ccagcctggg caatcacagt gagaccttgt ctcaaaacaa acaaacaaac    15440
aaatgaaaaa ccttagccag gcatggtgac acatgcctgt agttctagct acttggaagg    15500
cagaggcagg aagatcgctt gagcccagga gttcaaaact gcagtgagct atgatcacac    15560
cattgcactc caagtctggg caacagaggg agaccctgtc tggaaagaaa gagagaaaga    15620
gagagagaga gaaagaggga aagaaagcaa gcaagagaga aagaagaaag aaaatgacct    15680
aggaccctcg gaaagcacct tagggtggga ccacataggc acagtctga gaagatggtg     15740 ttctagatgg agcacaggga ccgggataga gatgttacag gggaactgtg gagaaaagag    15800
cctcctggtg gaagggttca gaggtgggac gcagcgaggc tgcatgggcg agaggtgata    15860
gcttggctcg gcagaaccac aaactctgtt ttaggcggag caaaagtgag gggcaccaca    15920
ggcgaacagg taggacagca aaagaatggt gggtgcccag acgctgggtg aaaagatgcc    15980
ccgtttccgc aggcttagga gtggccacgt gctaccattt gattttcttt cttctaggca    16040
atttcttgca accaccaccg aggccccgaa aagcactggt cgtcaggag ctcctcccct     16100 tggcccccag cctgtgccag ccctggcccg gctgccacac ctctgtttcc taggctgggg    16160
acccagcttg tctctccttg tttcttccca ctgcactgtg gtgcttcagt ggccaccagc    16220
ctcgtcacat acaccagcat cttttctgtac ctcctcccctt tggtgacctg aagtcactgt   16280
gacagttctc caggaaggag gagcttccta cttttgagtt tctctgtgga aataaaacat    16340
gaatcttgtt tccta                                                     16356

<210> SEQ ID NO 2
<211> LENGTH: 2097
<212> TYPE: DNA
<213> ORGANISM: Homo sapiens
<220> FEATURE:
<221> NAME/KEY: CDS
<222> LOCATION: (101)..(1768)

<400> SEQUENCE: 2
gaggaggaca gaggagggca cagagacgca gagcaagggc ggcaaggagg agaccctggt     60
gggaggaaga cactctggag agagaggggg ctgggcagag atg aag ttc cag ggg    115
                                             Met Lys Phe Gln Gly
                                             1               5 ccc ctg gcc tgc ctc ctg ctg gcc ctc tgc ctg ggc agt ggg gag gct    163
Pro Leu Ala Cys Leu Leu Leu Ala Leu Cys Leu Gly Ser Gly Glu Ala
            10                  15                  20 ggc ccc ctg cag agc gga gag gaa agc act ggg aca aat att ggg gag    211
Gly Pro Leu Gln Ser Gly Glu Glu Ser Thr Gly Thr Asn Ile Gly Glu
        25                  30                  35 gcc ctt gga cat ggc ctg gga gac gcc ctg agc gaa ggg gtg gga aag    259
Ala Leu Gly His Gly Leu Gly Asp Ala Leu Ser Glu Gly Val Gly Lys
    40                  45                  50 gcc att ggc aaa gag gcc gga ggg gca gct ggc tct aaa gtc agt gag    307
Ala Ile Gly Lys Glu Ala Gly Gly Ala Ala Gly Ser Lys Val Ser Glu
55                  60                  65 gcc ctt ggc caa ggg acc aga gaa gca gtt ggc act gga gtc agg cag    355
```

| | | | |
|---|---|---|---|
| Ala Leu Gly Gln Gly Thr Arg Glu Ala Val Gly Thr Gly Val Arg Gln | | | |
| 70 | 75 | 80 | 85 |

| | | |
|---|---|---|
| gtt cca ggc ttt ggc gca gca gat gct ttg ggc aac agg gtc ggg gaa | | 403 |
| Val Pro Gly Phe Gly Ala Ala Asp Ala Leu Gly Asn Arg Val Gly Glu | | |
| 90 | 95 | 100 |
| gca gcc cat gct ctg gga aac act ggg cac gag att ggc aga cag gca | | 451 |
| Ala Ala His Ala Leu Gly Asn Thr Gly His Glu Ile Gly Arg Gln Ala | | |
| 105 | 110 | 115 |
| gaa gat gtc att cga cac gga gca gat gct gtc cgc ggc tcc tgg cag | | 499 |
| Glu Asp Val Ile Arg His Gly Ala Asp Ala Val Arg Gly Ser Trp Gln | | |
| 120 | 125 | 130 |
| ggg gtg cct ggc cac aat ggt gct tgg gaa act tct gga ggc cat ggc | | 547 |
| Gly Val Pro Gly His Asn Gly Ala Trp Glu Thr Ser Gly Gly His Gly | | |
| 135 | 140 | 145 |
| atc ttt ggc tct caa ggt ggc ctt gga ggc cag ggc cag ggc aat cct | | 595 |
| Ile Phe Gly Ser Gln Gly Gly Leu Gly Gly Gln Gly Gln Gly Asn Pro | | |
| 150 | 155 | 160 | 165 |
| gga ggt ctg ggg act ccg tgg gtc cac gga tac ccc gga aac tca gca | | 643 |
| Gly Gly Leu Gly Thr Pro Trp Val His Gly Tyr Pro Gly Asn Ser Ala | | |
| 170 | 175 | 180 |
| ggc agc ttt gga atg aat cct cag gga gct ccc tgg ggt caa gga ggc | | 691 |
| Gly Ser Phe Gly Met Asn Pro Gln Gly Ala Pro Trp Gly Gln Gly Gly | | |
| 185 | 190 | 195 |
| aat gga ggg cca cca aac ttt ggg acc aac act cag gga gct gtg gcc | | 739 |
| Asn Gly Gly Pro Pro Asn Phe Gly Thr Asn Thr Gln Gly Ala Val Ala | | |
| 200 | 205 | 210 |
| cag cct ggc tat ggt tca gtg aga gcc agc aac cag aat gaa ggg tgc | | 787 |
| Gln Pro Gly Tyr Gly Ser Val Arg Ala Ser Asn Gln Asn Glu Gly Cys | | |
| 215 | 220 | 225 |
| acg aat ccc cca cca tct ggc tca ggt gga ggc tcc agc aac tct ggg | | 835 |
| Thr Asn Pro Pro Pro Ser Gly Ser Gly Gly Gly Ser Ser Asn Ser Gly | | |
| 230 | 235 | 240 | 245 |
| gga ggc agc ggc tca cag tcg ggc agc agt ggc agt ggc agc aat ggt | | 883 |
| Gly Gly Ser Gly Ser Gln Ser Gly Ser Ser Gly Ser Gly Ser Asn Gly | | |
| 250 | 255 | 260 |
| gac aac aac aat ggc agc agc agt ggt ggc agc agc agt ggc agc agc | | 931 |
| Asp Asn Asn Asn Gly Ser Ser Ser Gly Gly Ser Ser Ser Gly Ser Ser | | |
| 265 | 270 | 275 |
| agt ggc ggc agc agt ggc ggc agc agt ggt ggc agc agt ggc aac agt | | 979 |
| Ser Gly Gly Ser Ser Gly Gly Ser Ser Gly Gly Ser Ser Gly Asn Ser | | |
| 280 | 285 | 290 |
| ggt ggc agc aga ggt gac agc ggc agt gag tcc tcc tgg ggc agt tct | | 1027 |
| Gly Gly Ser Arg Gly Asp Ser Gly Ser Glu Ser Ser Trp Gly Ser Ser | | |
| 295 | 300 | 305 |
| ggg aat ggt gac caa ggc agc tac ggc cgc tcc cag gga tcc agc acc | | 1075 |
| Gly Asn Gly Asp Gln Gly Ser Tyr Gly Arg Ser Gln Gly Ser Ser Thr | | |
| 310 | 315 | 320 | 325 |
| ggc tcc tcc tcc ggc aac cac ggt ggg agc ggc gga gga aat gga cat | | 1123 |
| Gly Ser Ser Ser Gly Asn His Gly Gly Ser Gly Gly Gly Asn Gly His | | |
| 330 | 335 | 340 |
| aaa ccc ggg tgt gaa aag cca ggg aat gaa gcc cgc ggg agc ggg gaa | | 1171 |
| Lys Pro Gly Cys Glu Lys Pro Gly Asn Glu Ala Arg Gly Ser Gly Glu | | |
| 345 | 350 | 355 |
| tct ggg att cag ggc ttc aga gga cag gga gtt tcc agc aac atg agg | | 1219 |
| Ser Gly Ile Gln Gly Phe Arg Gly Gln Gly Val Ser Ser Asn Met Arg | | |
| 360 | 365 | 370 |
| gaa ata agc aaa gag ggc aat cgc ctc ctt gga ggc tct gga gac aat | | 1267 |
| Glu Ile Ser Lys Glu Gly Asn Arg Leu Leu Gly Gly Ser Gly Asp Asn | | |
| 375 | 380 | 385 |

```
tat cgg ggg caa ggg tcg agc tgg ggc agt gga gga ggt gac gct gtt    1315
Tyr Arg Gly Gln Gly Ser Ser Trp Gly Ser Gly Gly Gly Asp Ala Val
390                 395                 400                 405 ggt gga gtc aat att cag aac tct gag acg tct cct ggg atg ttt aac    1363
Gly Gly Val Asn Ile Gln Asn Ser Glu Thr Ser Pro Gly Met Phe Asn
                410                 415                 420 ttt gac act ttc tgg aag aat ttt aaa tcc aag ctg ggt ttc atc aac    1411
Phe Asp Thr Phe Trp Lys Asn Phe Lys Ser Lys Leu Gly Phe Ile Asn
            425                 430                 435 tgg gat gcc ata aac aag aac cag gtc ccg ccc ccc agc acc cga gcc    1459
Trp Asp Ala Ile Asn Lys Asn Gln Val Pro Pro Pro Ser Thr Arg Ala
        440                 445                 450 ctc ctc tac ttc agc cga ctc tgg gag gat ttc aaa cag aac act cct    1507
Leu Leu Tyr Phe Ser Arg Leu Trp Glu Asp Phe Lys Gln Asn Thr Pro
    455                 460                 465 ttc ctc aac tgg aaa gca att att gag ggt gcg gac gcg tca tca ctg    1555
Phe Leu Asn Trp Lys Ala Ile Ile Glu Gly Ala Asp Ala Ser Ser Leu
470                 475                 480                 485 cag aaa cgt gca ggc aga gcc gat cag ccg ggt gca gga tgg cag gag    1603
Gln Lys Arg Ala Gly Arg Ala Asp Gln Pro Gly Ala Gly Trp Gln Glu
                490                 495                 500 gtg gca gct gta act tcc aag aac tac aat tac aac cag cat gcg tat    1651
Val Ala Ala Val Thr Ser Lys Asn Tyr Asn Tyr Asn Gln His Ala Tyr
            505                 510                 515 ccc act gcc tat ggt ggg aag tac tca gtc aag acc cct gca aag ggg    1699
Pro Thr Ala Tyr Gly Gly Lys Tyr Ser Val Lys Thr Pro Ala Lys Gly
        520                 525                 530 gga gtc tca cct tct tcc tcg gct tcc cgg gtg caa cct ggc ctg ctg    1747
Gly Val Ser Pro Ser Ser Ser Ala Ser Arg Val Gln Pro Gly Leu Leu
    535                 540                 545 cag tgg gtg aag ttt tgg tag gcaatttctt gcaaccacca ccgaggcccc      1798
Gln Trp Val Lys Phe Trp
550                 555 gaaaagcact ggtcgtcagg gagctcctcc ccttggcccc cagcctgtgc cagccctggc   1858
ccggctgcca cacctctgtt tcctaggctg gggacccagc ttgtctctcc ttgtttcttc   1918
ccactgcact gtggtgcttc agtggccacc agcctcgtca catacaccag catctttctg   1978
tacctcctcc ctttggtgac ctgaagtcac tgtgacagtt ctccaggaag gaggagcttc   2038
ctacttttga gtttctctgt ggaaataaaa catgaatctt gtttccctaa aaaaaaaa    2097

<210> SEQ ID NO 3
<211> LENGTH: 555
<212> TYPE: PRT
<213> ORGANISM: Homo sapiens

<400> SEQUENCE: 3

Met Lys Phe Gln Gly Pro Leu Ala Cys Leu Leu Ala Leu Cys Leu
1               5                   10                  15

Gly Ser Gly Glu Ala Gly Pro Leu Gln Ser Gly Glu Ser Thr Gly
                20                  25                  30

Thr Asn Ile Gly Glu Ala Leu Gly His Gly Leu Gly Asp Ala Leu Ser
            35                  40                  45

Glu Gly Val Gly Lys Ala Ile Gly Lys Glu Ala Gly Ala Ala Gly
    50                  55                  60

Ser Lys Val Ser Glu Ala Leu Gly Gln Gly Thr Arg Glu Ala Val Gly
65                  70                  75                  80

Thr Gly Val Arg Gln Val Pro Gly Phe Gly Ala Ala Asp Ala Leu Gly
                85                  90                  95
```

```
Asn Arg Val Gly Glu Ala Ala His Ala Leu Gly Asn Thr Gly His Glu
            100                 105                 110

Ile Gly Arg Gln Ala Glu Asp Val Ile Arg His Gly Ala Asp Ala Val
            115                 120                 125

Arg Gly Ser Trp Gln Gly Val Pro Gly His Asn Gly Ala Trp Glu Thr
        130                 135                 140

Ser Gly Gly His Gly Ile Phe Gly Ser Gln Gly Gly Leu Gly Gly Gln
145                 150                 155                 160

Gly Gln Gly Asn Pro Gly Gly Leu Gly Thr Pro Trp Val His Gly Tyr
                165                 170                 175

Pro Gly Asn Ser Ala Gly Ser Phe Gly Met Asn Pro Gln Gly Ala Pro
            180                 185                 190

Trp Gln Gly Gly Asn Gly Gly Pro Pro Asn Phe Gly Thr Asn Thr
            195                 200                 205

Gln Gly Ala Val Ala Gln Pro Gly Tyr Gly Ser Val Arg Ala Ser Asn
        210                 215                 220

Gln Asn Glu Gly Cys Thr Asn Pro Pro Ser Gly Ser Gly Gly Gly
225                 230                 235                 240

Ser Ser Asn Ser Gly Gly Gly Ser Gly Ser Gln Ser Gly Ser Ser Gly
                245                 250                 255

Ser Gly Ser Asn Gly Asp Asn Asn Gly Ser Ser Ser Gly Gly Ser
            260                 265                 270

Ser Ser Gly Ser Ser Ser Gly Gly Ser Ser Gly Gly Ser Ser Gly Gly
        275                 280                 285

Ser Ser Gly Asn Ser Gly Gly Ser Arg Gly Asp Ser Gly Ser Glu Ser
        290                 295                 300

Ser Trp Gly Ser Ser Gly Asn Gly Asp Gln Gly Ser Tyr Gly Arg Ser
305                 310                 315                 320

Gln Gly Ser Ser Thr Gly Ser Ser Ser Gly Asn His Gly Gly Ser Gly
                325                 330                 335

Gly Gly Asn Gly His Lys Pro Gly Cys Glu Lys Pro Gly Asn Glu Ala
            340                 345                 350

Arg Gly Ser Gly Glu Ser Gly Ile Gln Gly Phe Arg Gly Gln Gly Val
        355                 360                 365

Ser Ser Asn Met Arg Glu Ile Ser Lys Glu Gly Asn Arg Leu Leu Gly
        370                 375                 380

Gly Ser Gly Asp Asn Tyr Arg Gly Gln Gly Ser Ser Trp Gly Ser Gly
385                 390                 395                 400

Gly Gly Asp Ala Val Gly Gly Val Asn Ile Gln Asn Ser Glu Thr Ser
                405                 410                 415

Pro Gly Met Phe Asn Phe Asp Thr Phe Trp Lys Asn Phe Lys Ser Lys
            420                 425                 430

Leu Gly Phe Ile Asn Trp Asp Ala Ile Asn Lys Asn Gln Val Pro Pro
        435                 440                 445

Pro Ser Thr Arg Ala Leu Leu Tyr Phe Ser Arg Leu Trp Glu Asp Phe
        450                 455                 460

Lys Gln Asn Thr Pro Phe Leu Asn Trp Lys Ala Ile Ile Glu Gly Ala
465                 470                 475                 480

Asp Ala Ser Ser Leu Gln Lys Arg Ala Gly Arg Ala Asp Gln Pro Gly
                485                 490                 495

Ala Gly Trp Gln Glu Val Ala Ala Val Thr Ser Lys Asn Tyr Asn Tyr
            500                 505                 510
```

```
Asn Gln His Ala Tyr Pro Thr Ala Tyr Gly Gly Lys Tyr Ser Val Lys
        515                 520                 525

Thr Pro Ala Lys Gly Gly Val Ser Pro Ser Ser Ala Ser Arg Val
    530                 535                 540

Gln Pro Gly Leu Leu Gln Trp Val Lys Phe Trp
545                 550                 555

<210> SEQ ID NO 4
<211> LENGTH: 1734
<212> TYPE: DNA
<213> ORGANISM: Homo sapiens
<220> FEATURE:
<221> NAME/KEY: CDS
<222> LOCATION: (184)..(1506)

<400> SEQUENCE: 4
gtggactctg agaagcccag gcagttgagg acaggagaga gaaggctgca gacccagagg      60
gagggaggac agggagtcgg aaggaggagg acagaggagg cacagagac gcagagcaag     120 ggcggcaagg aggagaccct ggtgggagga agacactctg agagagagg gggctgggca     180 gag atg aag ttc cag ggg ccc ctg gcc tgc ctc ctg ctg gcc ctc tgc      228
    Met Lys Phe Gln Gly Pro Leu Ala Cys Leu Leu Leu Ala Leu Cys
    1               5                   10                  15 ctg ggc agt ggg gag gct ggc ccc ctg cag agc gga gag gaa agc act      276
Leu Gly Ser Gly Glu Ala Gly Pro Leu Gln Ser Gly Glu Glu Ser Thr
                20                  25                  30 ggg aca aat att ggg gag gcc ctt gga cat ggc ctg gga gac gcc ctg      324
Gly Thr Asn Ile Gly Glu Ala Leu Gly His Gly Leu Gly Asp Ala Leu
            35                  40                  45 agc gaa ggg gtg gga aag gcc att ggc aaa gag gcc gga ggg gca gct      372
Ser Glu Gly Val Gly Lys Ala Ile Gly Lys Glu Ala Gly Gly Ala Ala
        50                  55                  60 ggc tct aaa gtc agt gag gcc ctt ggc caa ggg acc aga gaa gca gtt      420
Gly Ser Lys Val Ser Glu Ala Leu Gly Gln Gly Thr Arg Glu Ala Val
65                  70                  75 ggc act gga gtc agg cag gtt cca ggc ttt ggc gca gca gat gct ttg      468
Gly Thr Gly Val Arg Gln Val Pro Gly Phe Gly Ala Ala Asp Ala Leu
80                  85                  90                  95 ggc aac agg gtc ggg gaa gca gcc cat gct ctg gga aac act ggg cac      516
Gly Asn Arg Val Gly Glu Ala Ala His Ala Leu Gly Asn Thr Gly His
                100                 105                 110 gag att ggc aga cag gca gaa gat gtc att cga cac gga gca gat gct      564
Glu Ile Gly Arg Gln Ala Glu Asp Val Ile Arg His Gly Ala Asp Ala
            115                 120                 125 gtc cgc ggc tcc tgg cag ggg gtg cct ggc cac agt ggt gct tgg gaa      612
Val Arg Gly Ser Trp Gln Gly Val Pro Gly His Ser Gly Ala Trp Glu
        130                 135                 140 act tct gga ggc cat ggc atc ttt ggc tct caa ggt ggc ctt gga ggc      660
Thr Ser Gly Gly His Gly Ile Phe Gly Ser Gln Gly Gly Leu Gly Gly
145                 150                 155 cag ggc cag ggc aat cct gga ggt ctg ggg act ccg tgg gtc cac gga      708
Gln Gly Gln Gly Asn Pro Gly Gly Leu Gly Thr Pro Trp Val His Gly
160                 165                 170                 175 tac ccc gga aac tca gca ggc agc ttt gga atg aat cct cag gga gct      756
Tyr Pro Gly Asn Ser Ala Gly Ser Phe Gly Met Asn Pro Gln Gly Ala
                180                 185                 190 ccc tgg ggt caa gga ggc aat gga ggg cca cca aac ttt ggg acc aac      804
Pro Trp Gly Gln Gly Gly Asn Gly Gly Pro Pro Asn Phe Gly Thr Asn
            195                 200                 205 act cag gga gct gtg gcc cag cct ggc tat ggt tca gtg aga gcc agc      852
Thr Gln Gly Ala Val Ala Gln Pro Gly Tyr Gly Ser Val Arg Ala Ser
```

```
Thr Gln Gly Ala Val Ala Gln Pro Gly Tyr Gly Ser Val Arg Ala Ser
        210                 215                 220 aac cag aat gaa ggg tgc acg aat ccc cca cca tct ggc tca ggt gga           900
Asn Gln Asn Glu Gly Cys Thr Asn Pro Pro Pro Ser Gly Ser Gly Gly
        225                 230                 235 ggc tcc agc aac tct ggg gga ggc agc ggc tca cag tcg ggc agc agt           948
Gly Ser Ser Asn Ser Gly Gly Gly Ser Gly Ser Gln Ser Gly Ser Ser
240                 245                 250                 255 ggc agt ggc agc aat ggt gac aac aac aat ggc agc agc agt ggt ggc           996
Gly Ser Gly Ser Asn Gly Asp Asn Asn Asn Gly Ser Ser Ser Gly Gly
                260                 265                 270 agc agc agt ggc agc agc agt ggc agc agc agt ggc ggc agc agt ggc          1044
Ser Ser Ser Gly Ser Ser Ser Gly Ser Ser Ser Gly Gly Ser Ser Gly
            275                 280                 285 ggc agc agt ggt ggc agc agt ggc aac agt ggt ggc agc aga ggt gac          1092
Gly Ser Ser Gly Gly Ser Ser Gly Asn Ser Gly Gly Ser Arg Gly Asp
        290                 295                 300 agc ggc agt gag tcc tcc tgg gga tcc agc acc ggc tcc tcc tcc ggc          1140
Ser Gly Ser Glu Ser Ser Trp Gly Ser Ser Thr Gly Ser Ser Ser Gly
    305                 310                 315 aac cac ggt ggg agc ggc gga gga aat gga cat aaa ccc ggg tgt gaa          1188
Asn His Gly Gly Ser Gly Gly Gly Asn Gly His Lys Pro Gly Cys Glu
320                 325                 330                 335 aag cca ggg aat gaa gcc cgc ggg agc ggg gaa tct ggg att cag ggc          1236
Lys Pro Gly Asn Glu Ala Arg Gly Ser Gly Glu Ser Gly Ile Gln Gly
                340                 345                 350 ttc aga gga cag gga gtt tcc agc aac atg agg gaa ata agc aaa gag          1284
Phe Arg Gly Gln Gly Val Ser Ser Asn Met Arg Glu Ile Ser Lys Glu
            355                 360                 365 ggc aat cgc ctc ctt gga ggc tct gga gac aat tat cgg ggg caa ggg          1332
Gly Asn Arg Leu Leu Gly Gly Ser Gly Asp Asn Tyr Arg Gly Gln Gly
        370                 375                 380 tcg agc tgg ggc agt gga gga ggt gac gct gtt ggt gga gtc aat act          1380
Ser Ser Trp Gly Ser Gly Gly Gly Asp Ala Val Gly Gly Val Asn Thr
    385                 390                 395 gtg aac tct gag acg tct cct ggg atg ttt aac ttt gac act ttc tgg          1428
Val Asn Ser Glu Thr Ser Pro Gly Met Phe Asn Phe Asp Thr Phe Trp
400                 405                 410                 415 aag aat ttt aaa tcc aag ctg ggt ttc atc aac tgg gat gcc ata aac          1476
Lys Asn Phe Lys Ser Lys Leu Gly Phe Ile Asn Trp Asp Ala Ile Asn
                420                 425                 430 aag gac cag aga agc tct cgc atc ccg tga cctccagaca aggagccacc            1526
Lys Asp Gln Arg Ser Ser Arg Ile Pro
            435                 440 agattggatg ggagccccca cactccctcc ttaaaacacc accctctcat cactaatctc        1586
agcccttgcc cttgaaataa accttagctg ccccacaaaa aaaaaaaaaa aaaaaaaaaa        1646
aaaaaaaaaa aaaaaaaaaa aaaaaaaaaa aaaaaaaaaa aaaaaaaaaa aaaaaaaaaa        1706
aaaaaaaaaa aaaaaaaaa aaaaaaaa                                            1734

<210> SEQ ID NO 5
<211> LENGTH: 440
<212> TYPE: PRT
<213> ORGANISM: Homo sapiens

<400> SEQUENCE: 5

Met Lys Phe Gln Gly Pro Leu Ala Cys Leu Leu Leu Ala Leu Cys Leu
1               5                   10                  15

Gly Ser Gly Glu Ala Gly Pro Leu Gln Ser Gly Glu Glu Ser Thr Gly
```

-continued

```
                20                  25                  30
Thr Asn Ile Gly Glu Ala Leu Gly His Gly Leu Gly Asp Ala Leu Ser
             35                  40                  45
Glu Gly Val Gly Lys Ala Ile Gly Lys Glu Ala Gly Ala Ala Gly
         50                  55                  60
Ser Lys Val Ser Glu Ala Leu Gly Gln Gly Thr Arg Glu Ala Val Gly
 65                  70                  75                  80
Thr Gly Val Arg Gln Val Pro Gly Phe Gly Ala Ala Asp Ala Leu Gly
                 85                  90                  95
Asn Arg Val Gly Glu Ala Ala His Ala Leu Gly Asn Thr Gly His Glu
             100                 105                 110
Ile Gly Arg Gln Ala Glu Asp Val Ile Arg His Gly Ala Asp Ala Val
             115                 120                 125
Arg Gly Ser Trp Gln Gly Val Pro Gly His Ser Gly Ala Trp Glu Thr
         130                 135                 140
Ser Gly Gly His Gly Ile Phe Gly Ser Gln Gly Gly Leu Gly Gly Gln
145                 150                 155                 160
Gly Gln Gly Asn Pro Gly Gly Leu Gly Thr Pro Trp Val His Gly Tyr
                 165                 170                 175
Pro Gly Asn Ser Ala Gly Ser Phe Gly Met Asn Pro Gln Gly Ala Pro
             180                 185                 190
Trp Gly Gln Gly Gly Asn Gly Pro Pro Asn Phe Gly Thr Asn Thr
         195                 200                 205
Gln Gly Ala Val Ala Gln Pro Gly Tyr Gly Ser Val Arg Ala Ser Asn
         210                 215                 220
Gln Asn Glu Gly Cys Thr Asn Pro Pro Ser Gly Ser Gly Gly Gly
225                 230                 235                 240
Ser Ser Asn Ser Gly Gly Gly Ser Gly Ser Gln Ser Gly Ser Ser Gly
                 245                 250                 255
Ser Gly Ser Asn Gly Asp Asn Asn Gly Ser Ser Ser Gly Gly Ser
             260                 265                 270
Ser Ser Gly Ser Ser Ser Gly Ser Ser Ser Gly Gly Ser Ser Gly Gly
         275                 280                 285
Ser Ser Gly Gly Ser Ser Gly Asn Ser Gly Gly Ser Arg Gly Asp Ser
         290                 295                 300
Gly Ser Glu Ser Ser Trp Gly Ser Ser Thr Gly Ser Ser Ser Gly Asn
305                 310                 315                 320
His Gly Gly Ser Gly Gly Gly Asn Gly His Lys Pro Gly Cys Glu Lys
                 325                 330                 335
Pro Gly Asn Glu Ala Arg Gly Ser Gly Glu Ser Gly Ile Gln Gly Phe
             340                 345                 350
Arg Gly Gln Gly Val Ser Ser Asn Met Arg Glu Ile Ser Lys Glu Gly
         355                 360                 365
Asn Arg Leu Leu Gly Gly Ser Gly Asp Asn Tyr Arg Gly Gln Gly Ser
         370                 375                 380
Ser Trp Gly Ser Gly Gly Gly Asp Ala Val Gly Gly Val Asn Thr Val
385                 390                 395                 400
Asn Ser Glu Thr Ser Pro Gly Met Phe Asn Phe Asp Thr Phe Trp Lys
                 405                 410                 415
Asn Phe Lys Ser Lys Leu Gly Phe Ile Asn Trp Asp Ala Ile Asn Lys
             420                 425                 430
Asp Gln Arg Ser Ser Arg Ile Pro
         435                 440
```

```
<210> SEQ ID NO 6
<211> LENGTH: 1124
<212> TYPE: DNA
<213> ORGANISM: Homo sapiens
<220> FEATURE:
<221> NAME/KEY: CDS
<222> LOCATION: (44)..(805)

<400> SEQUENCE: 6
attgcgtagt tccgaatacc ctcggccaca cctggccttc tcc atg ctc gga ata         55
                                              Met Leu Gly Ile
                                              1 act tcc tgc agc gac caa cag gct aaa gag ggg gaa ggt ctg gag gga        103
Thr Ser Cys Ser Asp Gln Gln Ala Lys Glu Gly Glu Gly Leu Glu Gly
5               10                  15                  20 tcc agc acc ggc tcc tcc tcc ggc aac cac ggt ggg agc ggc gga gga        151
Ser Ser Thr Gly Ser Ser Ser Gly Asn His Gly Gly Ser Gly Gly Gly
                25                  30                  35 aat gga cat aaa ccc ggg tgt gaa aag cca ggg aat gaa gcc cgc ggg        199
Asn Gly His Lys Pro Gly Cys Glu Lys Pro Gly Asn Glu Ala Arg Gly
            40                  45                  50 agc ggg gaa tct ggg att cag ggc ttc aga gga cag gga gtt tcc agc        247
Ser Gly Glu Ser Gly Ile Gln Gly Phe Arg Gly Gln Gly Val Ser Ser
        55                  60                  65 aac atg agg gaa ata agc aaa gag ggc aat cgc ctc ctt gga ggc tct        295
Asn Met Arg Glu Ile Ser Lys Glu Gly Asn Arg Leu Leu Gly Gly Ser
    70                  75                  80 gga gac aat tat cgg ggg caa ggg tcg agc tgg ggc agt gga gga ggt        343
Gly Asp Asn Tyr Arg Gly Gln Gly Ser Ser Trp Gly Ser Gly Gly Gly
85                  90                  95                 100 gac gct gtt ggt gga gtc aat att cag aac tct gag acg tct cct ggg        391
Asp Ala Val Gly Gly Val Asn Ile Gln Asn Ser Glu Thr Ser Pro Gly
                105                 110                 115 atg ttt aac ttt gac act ttc tgg aag aat ttt aaa tcc aag ctg ggt        439
Met Phe Asn Phe Asp Thr Phe Trp Lys Asn Phe Lys Ser Lys Leu Gly
            120                 125                 130 ttc atc aac tgg gat gcc ata aac aag aac cag gtc ccg ccc ccc agc        487
Phe Ile Asn Trp Asp Ala Ile Asn Lys Asn Gln Val Pro Pro Pro Ser
        135                 140                 145 acc cga gcc ctc ctc tac ttc agc cga ctc tgg gag gat ttc aaa cag        535
Thr Arg Ala Leu Leu Tyr Phe Ser Arg Leu Trp Glu Asp Phe Lys Gln
    150                 155                 160 aac act cct ttc ctc aac tgg aaa gca att att gag ggt gcg gac gcg        583
Asn Thr Pro Phe Leu Asn Trp Lys Ala Ile Ile Glu Gly Ala Asp Ala
165                 170                 175                 180 tca tca ctg cag aaa cgt gca ggc aga gac gat cag ccg ggt gca gga        631
Ser Ser Leu Gln Lys Arg Ala Gly Arg Asp Asp Gln Pro Gly Ala Gly
                185                 190                 195 tgg cag gag gtg gca gct gta act tcc aag aac tac aat tac aac cag        679
Trp Gln Glu Val Ala Ala Val Thr Ser Lys Asn Tyr Asn Tyr Asn Gln
            200                 205                 210 cat gcg tat ccc act gcc tat ggt ggg aag tac tca gtc aag acc cct        727
His Ala Tyr Pro Thr Ala Tyr Gly Gly Lys Tyr Ser Val Lys Thr Pro
        215                 220                 225 gca aag ggg gga gtc tca cct tct tcc tcg gct tcc cgg gtg caa cct        775
Ala Lys Gly Gly Val Ser Pro Ser Ser Ser Ala Ser Arg Val Gln Pro
    230                 235                 240 ggc ctg ctg cag tgg gtg aag ttt tgg tag gcaatttctt gcaaccacca          825
Gly Leu Leu Gln Trp Val Lys Phe Trp
245                 250
```

```
ccgaggcccc gaaaagcact ggtcgtcagg gagctcctcc ccttggcccc cagcctgtgc      885
cagccctggc ccggctgcca cacctctgtt tcctaggctg gggacccagc ttgtctctcc      945
ttgtttcttc ccactgcact gtggtgcttc agtggccacc agcctcgtca catacaccag     1005
catctttctg tacctcctcc ctttggtgac ctgaagtcac tgtgacagtt ctccaggaag     1065
gaggagcttc ctacttttga gtttctctgt ggaaataaaa catgaatctt gtttcccta     1124

<210> SEQ ID NO 7
<211> LENGTH: 253
<212> TYPE: PRT
<213> ORGANISM: Homo sapiens

<400> SEQUENCE: 7

Met Leu Gly Ile Thr Ser Cys Ser Asp Gln Gln Ala Lys Glu Gly Glu
1               5                   10                  15

Gly Leu Glu Gly Ser Ser Thr Gly Ser Ser Ser Gly Asn His Gly Gly
            20                  25                  30

Ser Gly Gly Asn Gly His Lys Pro Gly Cys Glu Lys Pro Gly Asn
        35                  40                  45

Glu Ala Arg Gly Ser Gly Glu Ser Gly Ile Gln Gly Phe Arg Gly Gln
    50                  55                  60

Gly Val Ser Ser Asn Met Arg Glu Ile Ser Lys Glu Gly Asn Arg Leu
65                  70                  75                  80

Leu Gly Gly Ser Gly Asp Asn Tyr Arg Gly Gln Gly Ser Ser Trp Gly
                85                  90                  95

Ser Gly Gly Gly Asp Ala Val Gly Gly Val Asn Ile Gln Asn Ser Glu
            100                 105                 110

Thr Ser Pro Gly Met Phe Asn Phe Asp Thr Phe Trp Lys Asn Phe Lys
        115                 120                 125

Ser Lys Leu Gly Phe Ile Asn Trp Asp Ala Ile Asn Lys Asn Gln Val
    130                 135                 140

Pro Pro Pro Ser Thr Arg Ala Leu Leu Tyr Phe Ser Arg Leu Trp Glu
145                 150                 155                 160

Asp Phe Lys Gln Asn Thr Pro Phe Leu Asn Trp Lys Ala Ile Ile Glu
                165                 170                 175

Gly Ala Asp Ala Ser Ser Leu Gln Lys Arg Ala Gly Arg Asp Asp Gln
            180                 185                 190

Pro Gly Ala Gly Trp Gln Glu Val Ala Ala Val Thr Ser Lys Asn Tyr
        195                 200                 205

Asn Tyr Asn Gln His Ala Tyr Pro Thr Ala Tyr Gly Gly Lys Tyr Ser
    210                 215                 220

Val Lys Thr Pro Ala Lys Gly Gly Val Ser Pro Ser Ser Ser Ala Ser
225                 230                 235                 240

Arg Val Gln Pro Gly Leu Leu Gln Trp Val Lys Phe Trp
                245                 250

<210> SEQ ID NO 8
<211> LENGTH: 646
<212> TYPE: DNA
<213> ORGANISM: Homo sapiens
<220> FEATURE:
<221> NAME/KEY: CDS
<222> LOCATION: (61)..(510)

<400> SEQUENCE: 8
accgacgaag atagaaattg cgtatgctcc gaataccctc ggccacacct ggccttctcc       60
```

| | |
|---|---|
| atg ctc gga ata act tcc tgc agc gac caa cag gct aaa gag ggg gaa<br>Met Leu Gly Ile Thr Ser Cys Ser Asp Gln Gln Ala Lys Glu Gly Glu<br>1                  5                    10                15 | 108 |
| ggt ctg gag gga tcc agc acc ggc tcc tcc tcc ggc aac cac ggt ggg<br>Gly Leu Glu Gly Ser Ser Thr Gly Ser Ser Ser Gly Asn His Gly Gly<br>         20                    25                    30 | 156 |
| agc ggc gga gga aat gga cat aaa ccc ggg tgt gaa aag cca ggg aat<br>Ser Gly Gly Gly Asn Gly His Lys Pro Gly Cys Glu Lys Pro Gly Asn<br>        35                    40                45 | 204 |
| gaa gcc cgc ggg agc ggg gaa tct ggg att cag ggc ttc aga gga cag<br>Glu Ala Arg Gly Ser Gly Glu Ser Gly Ile Gln Gly Phe Arg Gly Gln<br>50                    55                    60 | 252 |
| gga gtt tcc agc aac atg agg gaa ata agc aaa gag ggc aat cgc ctc<br>Gly Val Ser Ser Asn Met Arg Glu Ile Ser Lys Glu Gly Asn Arg Leu<br>65                  70                    75                    80 | 300 |
| ctt gga ggc tct gga gac aat tat cgg ggg caa ggg tcg agc tgg ggc<br>Leu Gly Gly Ser Gly Asp Asn Tyr Arg Gly Gln Gly Ser Ser Trp Gly<br>                   85                    90                    95 | 348 |
| agt gga gga ggt gac gct gtt ggt gga gtc aat att cag aac tct gag<br>Ser Gly Gly Gly Asp Ala Val Gly Gly Val Asn Ile Gln Asn Ser Glu<br>                100                    105                  110 | 396 |
| acg tct cct ggg atg ttt aac ttt gac act ttc tgg aag aat ttt aaa<br>Thr Ser Pro Gly Met Phe Asn Phe Asp Thr Phe Trp Lys Asn Phe Lys<br>                115                    120                  125 | 444 |
| tcc aag ctg ggt ttc atc aac tgg gat gcc ata aac aag gac cag aga<br>Ser Lys Leu Gly Phe Ile Asn Trp Asp Ala Ile Asn Lys Asp Gln Arg<br>130                    135                    140 | 492 |
| agc tct cgc atc ccg tga cctccagaca aggagccacc agattggatg<br>Ser Ser Arg Ile Pro<br>145 | 540 |
| ggagccccca cactccctcc ttaaaacacc accctctcat cactaatctc agcccttgcc | 600 |
| cttgaaataa accttagctg ccccaaaaaa aaaaaaaaa aaaccc | 646 |

<210> SEQ ID NO 9
<211> LENGTH: 149
<212> TYPE: PRT
<213> ORGANISM: Homo sapiens

<400> SEQUENCE: 9

Met Leu Gly Ile Thr Ser Cys Ser Asp Gln Gln Ala Lys Glu Gly Glu
1                  5                    10                15

Gly Leu Glu Gly Ser Ser Thr Gly Ser Ser Ser Gly Asn His Gly Gly
         20                    25                    30

Ser Gly Gly Gly Asn Gly His Lys Pro Gly Cys Glu Lys Pro Gly Asn
        35                    40                45

Glu Ala Arg Gly Ser Gly Glu Ser Gly Ile Gln Gly Phe Arg Gly Gln
50                    55                    60

Gly Val Ser Ser Asn Met Arg Glu Ile Ser Lys Glu Gly Asn Arg Leu
65                  70                    75                    80

Leu Gly Gly Ser Gly Asp Asn Tyr Arg Gly Gln Gly Ser Ser Trp Gly
                 85                    90                    95

Ser Gly Gly Gly Asp Ala Val Gly Gly Val Asn Ile Gln Asn Ser Glu
              100                    105                  110

Thr Ser Pro Gly Met Phe Asn Phe Asp Thr Phe Trp Lys Asn Phe Lys
              115                    120                  125

Ser Lys Leu Gly Phe Ile Asn Trp Asp Ala Ile Asn Lys Asp Gln Arg
130                    135                    140

Ser Ser Arg Ile Pro
145

<210> SEQ ID NO 10
<211> LENGTH: 600
<212> TYPE: DNA
<213> ORGANISM: Homo sapiens
<220> FEATURE:
<221> NAME/KEY: CDS
<222> LOCATION: (6)..(272)

<400> SEQUENCE: 10

```
tgaac atg aag ccg gcc act gcc tct gct ctg ctc ctg ctc ctg ctg ggc      50
      Met Lys Pro Ala Thr Ala Ser Ala Leu Leu Leu Leu Leu Leu Gly
      1               5                  10                  15 ctg gcc tgg acc cag ggg agc cac ggc tgg ggt gcg gac gcg tca tca        98
Leu Ala Trp Thr Gln Gly Ser His Gly Trp Gly Ala Asp Ala Ser Ser
             20                  25                  30 ctg cag aaa cgt gca ggc aga gac gat cag aac tac aat tac aac cag       146
Leu Gln Lys Arg Ala Gly Arg Asp Asp Gln Asn Tyr Asn Tyr Asn Gln
         35                  40                  45 cat gcg tat ccc act gcc tat ggt ggg aag tac tca gtc aag acc cct       194
His Ala Tyr Pro Thr Ala Tyr Gly Gly Lys Tyr Ser Val Lys Thr Pro
     50                  55                  60 gca aag ggg gga gtc tca cct tct tcc tcg gct tcc cgg gtg caa cct       242
Ala Lys Gly Gly Val Ser Pro Ser Ser Ser Ala Ser Arg Val Gln Pro
 65                  70                  75 ggc ctg ctg cag tgg gtg aag ttt tgg tag gcaatttctt gcaaccacca         292
Gly Leu Leu Gln Trp Val Lys Phe Trp
 80                  85 ccgaggcccc gaaaagcact ggtcgtcagg gagctcctcc ccttggcccc cagcctgtgc     352
cagccctggc ccggctgcca cacctctgtt tcctaggctg gggacccagc ttgtctctcc     412
ttgtttcttc ccactgcact gtggtgcttc agtggccacc agcctcgtca catacaccag     472
catctttctg tacctcctcc ctttggtgac ctgaagtcac tgtgacagtt ctccaggaag     532
gaggagcttc ctacttttga gtttctctgt ggaaataaaa catgaatctt gtttccctaa     592
aaaaaaaa                                                              600
```

<210> SEQ ID NO 11
<211> LENGTH: 88
<212> TYPE: PRT
<213> ORGANISM: Homo sapiens

<400> SEQUENCE: 11

Met Lys Pro Ala Thr Ala Ser Ala Leu Leu Leu Leu Leu Leu Gly Leu
1               5                   10                  15

Ala Trp Thr Gln Gly Ser His Gly Trp Gly Ala Asp Ala Ser Ser Leu
            20                  25                  30

Gln Lys Arg Ala Gly Arg Asp Asp Gln Asn Tyr Asn Tyr Asn Gln His
        35                  40                  45

Ala Tyr Pro Thr Ala Tyr Gly Gly Lys Tyr Ser Val Lys Thr Pro Ala
    50                  55                  60

Lys Gly Gly Val Ser Pro Ser Ser Ser Ala Ser Arg Val Gln Pro Gly
65                  70                  75                  80

Leu Leu Gln Trp Val Lys Phe Trp
            85

<210> SEQ ID NO 12

```
<211> LENGTH: 24
<212> TYPE: DNA
<213> ORGANISM: Homo sapiens

<400> SEQUENCE: 12
ggctgggcag agatgaagtt ccag                                          24

<210> SEQ ID NO 13
<211> LENGTH: 20
<212> TYPE: DNA
<213> ORGANISM: Homo sapiens

<400> SEQUENCE: 13
tctgcctggg cagtggggag                                               20

<210> SEQ ID NO 14
<211> LENGTH: 25
<212> TYPE: DNA
<213> ORGANISM: Homo sapiens

<400> SEQUENCE: 14
atgctcggaa taacttcctg cagcg                                         25

<210> SEQ ID NO 15
<211> LENGTH: 21
<212> TYPE: DNA
<213> ORGANISM: Homo sapiens

<400> SEQUENCE: 15
gcagcgacca acaggctaaa g                                             21

<210> SEQ ID NO 16
<211> LENGTH: 22
<212> TYPE: DNA
<213> ORGANISM: Homo sapiens

<400> SEQUENCE: 16
atgaagccgg ccactgcctc tg                                            22

<210> SEQ ID NO 17
<211> LENGTH: 20
<212> TYPE: DNA
<213> ORGANISM: Homo sapiens

<400> SEQUENCE: 17
ctctgctcct gctcctgctg                                               20

<210> SEQ ID NO 18
<211> LENGTH: 20
<212> TYPE: DNA
<213> ORGANISM: Homo sapiens

<400> SEQUENCE: 18
gggccagggc tggcacaggc                                               20

<210> SEQ ID NO 19
<211> LENGTH: 21
<212> TYPE: DNA
<213> ORGANISM: Homo sapiens

<400> SEQUENCE: 19
cggggcctcg gtggtggttg c                                             21
```

```
<210> SEQ ID NO 20
<211> LENGTH: 25
<212> TYPE: DNA
<213> ORGANISM: Homo sapiens

<400> SEQUENCE: 20
tctggtggct ccttgtctgg aggtc                                    25

<210> SEQ ID NO 21
<211> LENGTH: 28
<212> TYPE: DNA
<213> ORGANISM: Homo sapiens

<400> SEQUENCE: 21
gtcacgggat gcgagagctt ctctggtc                                 28

<210> SEQ ID NO 22
<211> LENGTH: 17
<212> TYPE: DNA
<213> ORGANISM: Homo sapiens

<400> SEQUENCE: 22
gcttttcaca cccgggt                                             17

<210> SEQ ID NO 23
<211> LENGTH: 20
<212> TYPE: DNA
<213> ORGANISM: Homo sapiens

<400> SEQUENCE: 23
ggcggaggaa atggacataa                                          20

<210> SEQ ID NO 24
<211> LENGTH: 26
<212> TYPE: DNA
<213> ORGANISM: Homo sapiens

<400> SEQUENCE: 24
gcttggattt aaaattcttc cagaaa                                   26

<210> SEQ ID NO 25
<211> LENGTH: 21
<212> TYPE: DNA
<213> ORGANISM: Homo sapiens

<400> SEQUENCE: 25
gaggtgacag cggcagtgag t                                        21

<210> SEQ ID NO 26
<211> LENGTH: 30
<212> TYPE: DNA
<213> ORGANISM: Homo sapiens

<400> SEQUENCE: 26
ttaaaattct tccagaaagt gtcaaagtta                               30

<210> SEQ ID NO 27
<211> LENGTH: 20
<212> TYPE: DNA
<213> ORGANISM: Homo sapiens

<400> SEQUENCE: 27
attcagaact ctgagacgtc                                          20
```

```
<210> SEQ ID NO 28
<211> LENGTH: 26
<212> TYPE: DNA
<213> ORGANISM: Homo sapiens

<400> SEQUENCE: 28
tgttggtgga gtcaatactg tgaact                                          26

<210> SEQ ID NO 29
<211> LENGTH: 19
<212> TYPE: DNA
<213> ORGANISM: Homo sapiens

<400> SEQUENCE: 29
cgggatgcga gagcttctc                                                  19

<210> SEQ ID NO 30
<211> LENGTH: 24
<212> TYPE: DNA
<213> ORGANISM: Homo sapiens

<400> SEQUENCE: 30
cactttctgg aagaatttta aatc                                            24

<210> SEQ ID NO 31
<211> LENGTH: 17
<212> TYPE: DNA
<213> ORGANISM: Homo sapiens

<400> SEQUENCE: 31
ggagcggcgg aggaaat                                                    17

<210> SEQ ID NO 32
<211> LENGTH: 21
<212> TYPE: DNA
<213> ORGANISM: Homo sapiens

<400> SEQUENCE: 32
tgatgaaacc cagcttggat t                                               21

<210> SEQ ID NO 33
<211> LENGTH: 20
<212> TYPE: DNA
<213> ORGANISM: Homo sapiens

<400> SEQUENCE: 33
aaacccggga actctgagac                                                 20

<210> SEQ ID NO 34
<211> LENGTH: 21
<212> TYPE: DNA
<213> ORGANISM: Homo sapiens

<400> SEQUENCE: 34
ggcggaggaa atggacataa a                                               21

<210> SEQ ID NO 35
<211> LENGTH: 25
<212> TYPE: DNA
<213> ORGANISM: Homo sapiens

<400> SEQUENCE: 35
gagcttctct ggtccttgtt tatgg                                           25
```

<210> SEQ ID NO 36
<211> LENGTH: 19
<212> TYPE: DNA
<213> ORGANISM: Homo sapiens

<400> SEQUENCE: 36
aatctgggat tcagaactc                                                    19

<210> SEQ ID NO 37
<211> LENGTH: 17
<212> TYPE: DNA
<213> ORGANISM: Homo sapiens

<400> SEQUENCE: 37
gggtgcggac gcgtcat                                                      17

<210> SEQ ID NO 38
<211> LENGTH: 27
<212> TYPE: DNA
<213> ORGANISM: Homo sapiens

<400> SEQUENCE: 38
gtcttgactg agtacttccc accatag                                           27

<210> SEQ ID NO 39
<211> LENGTH: 23
<212> TYPE: DNA
<213> ORGANISM: Homo sapiens

<400> SEQUENCE: 39
acgatcagaa ctacaattac aac                                               23

<210> SEQ ID NO 40
<211> LENGTH: 1113
<212> TYPE: DNA
<213> ORGANISM: Homo sapiens

<400> SEQUENCE: 40
atgaagttcc aggggcccct ggcctgcctc ctgctggccc tctgcctggg cagtggggag        60
gctggccccc tgcagagcgg agaggaaagc actgggacaa atattgggga ggcccttgga       120
catggcctgg agacgcccct gagcgaaggg gtgggaaagg ccattggcaa agaggccgga       180
ggggcagctg gctctaaagt cagtgaggcc cttggccaag ggaccagaga agcagttggc       240
actggagtca ggcaggttcc aggctttggc gcagcagatg ctttgggcaa cagggtcggg       300
gaagcagccc atgctctggg aaacactggg cacgagattg cagacaggc agaagatgtc       360 attcgacacg gagcagatgc tgtccgcggc tcctggcagg gggtgcctgg ccacaatggt       420
gcttgggaaa cttctggagg ccatggcatc tttggctctc aaggtggcct tggaggccag       480
ggccagggca atcctggagg tctggggact ccgtgggtcc acggataccc cggaaactca       540
gcaggcagct ttggaatgaa tcctcaggga gctccctggg gtcaaggagg caatggaggg       600
ccaccaaact ttgggaccaa cactcaggga gctgtggccc agcctggcta tggttcagtg       660
agagccagca accagaatga aggtgcacg aatcccccac catctggctc aggtggaggc       720
tccagcaact ctggggagg cagcggctca cagtcgggca gcagtggcag tggcagcaat       780
ggtgacaaca acaatggcag cagcagtggt gcagcagca gtggcagcag cagtggcggc       840
agcagtggcg gcagcagtgg tggcagcagt ggcaacagtg gtggcagcag aggtgatagc       900

```
ggcagtgagt cctcctgggg atccagcacc ggctcctcct ccggcaacca cggtgggagc      960
ggcggaggag atggacataa acccgggtgt gaaaagccag gaatgaagc ccgcgggagc      1020 ggggaatctg ggattcaggg gcaagggtcg agctggggca gtggaggagg tgacgctgtt    1080
ggtggagtca atactgtgaa ctctgagacg tct                                   1113
```

<210> SEQ ID NO 41
<211> LENGTH: 371
<212> TYPE: PRT
<213> ORGANISM: Homo sapiens

<400> SEQUENCE: 41

```
Met Lys Phe Gln Gly Pro Leu Ala Cys Leu Leu Ala Leu Cys Leu
 1               5                  10                  15

Gly Ser Gly Glu Ala Gly Pro Leu Gln Ser Gly Glu Glu Ser Thr Gly
                20                  25                  30

Thr Asn Ile Gly Glu Ala Leu Gly His Gly Leu Gly Asp Ala Leu Ser
            35                  40                  45

Glu Gly Val Gly Lys Ala Ile Gly Lys Glu Ala Gly Ala Ala Gly
 50                  55                  60

Ser Lys Val Ser Glu Ala Leu Gly Gln Gly Thr Arg Glu Ala Val Gly
 65                  70                  75                  80

Thr Gly Val Arg Gln Val Pro Gly Phe Gly Ala Ala Asp Ala Leu Gly
                85                  90                  95

Asn Arg Val Gly Glu Ala Ala His Ala Leu Gly Asn Thr Gly His Glu
            100                 105                 110

Ile Gly Arg Gln Ala Glu Asp Val Ile Arg His Gly Ala Asp Ala Val
        115                 120                 125

Arg Gly Ser Trp Gln Gly Val Pro Gly His Asn Gly Ala Trp Glu Thr
130                 135                 140

Ser Gly Gly His Gly Ile Phe Gly Ser Gln Gly Gly Leu Gly Gly Gln
145                 150                 155                 160

Gly Gln Gly Asn Pro Gly Gly Leu Gly Thr Pro Trp Val His Gly Tyr
                165                 170                 175

Pro Gly Asn Ser Ala Gly Ser Phe Gly Met Asn Pro Gln Gly Ala Pro
            180                 185                 190

Trp Gly Gln Gly Gly Asn Gly Gly Pro Pro Asn Phe Gly Thr Asn Thr
        195                 200                 205

Gln Gly Ala Val Ala Gln Pro Gly Tyr Gly Ser Val Arg Ala Ser Asn
210                 215                 220

Gln Asn Glu Gly Cys Thr Asn Pro Pro Ser Gly Ser Gly Gly
225                 230                 235                 240

Ser Ser Asn Ser Gly Gly Ser Gly Ser Gln Ser Gly Ser Ser Gly
                245                 250                 255

Ser Gly Ser Asn Gly Asp Asn Asn Gly Ser Ser Gly Gly Ser
            260                 265                 270

Ser Ser Gly Ser Ser Ser Gly Gly Ser Ser Gly Gly Ser Gly Gly
        275                 280                 285

Ser Ser Gly Asn Ser Gly Gly Ser Arg Gly Asp Ser Gly Ser Glu Ser
        290                 295                 300

Ser Trp Gly Ser Ser Thr Gly Ser Ser Ser Gly Asn His Gly Gly Ser
305                 310                 315                 320

Gly Gly Gly Asp Gly His Lys Pro Gly Cys Glu Lys Pro Gly Asn Glu
                325                 330                 335
```

```
Ala Arg Gly Ser Gly Glu Ser Gly Ile Gln Gly Gln Gly Ser Ser Trp
            340                 345                 350

Gly Ser Gly Gly Gly Asp Ala Val Gly Gly Val Asn Thr Val Asn Ser
        355                 360                 365

Glu Thr Ser
    370
```

CNGH0010 SPECIFIC POLYNUCLEOTIDES, POLYPEPTIDES, ANTIBODIES, COMPOSITIONS, METHODS AND USES

CROSS-REFERENCED TO RELATED APPLICATION

The present application claims the benefit of priority of U.S. Provisional Application Ser. No. 60/777,740, filed 28 Feb. 2006, and is a continuation-in-part of U.S. application Ser. No. 10/835,904, filed 30 Apr. 2004, now U.S. Pat. No. 7,326,687, which claims priority to U.S. Provisional Application Ser. No. 60/466,573, filed 30 Apr. 2003. The entire contents of the foregoing applications are incorporated herein in their entirety.

BACKGROUND OF THE INVENTION

A. Field of the Invention

The present invention relates to CNGH0010 polypeptides, variants, and fragments thereof, and antibodies and anti-idiotype antibodies specific therefor, as well as nucleic acids encoding such CNGH0010 polypeptides, variants, fragments, antibodies, complementary nucleic acids, vectors, host cells, and methods of making and using thereof, including diagnostic and therapeutic formulations, administration and devices.

B. Background and Related Art

Psoriasis is a genetic, multifactorial, chronic inflammatory skin disease, with a prevalence of 2.6% in the U.S. population. The disease is characterized by pronounced hyperproliferation of keratinocytes, which results in rapid epidermal turnover and thickened, scaly, red plaques observed clinically. Other prominent histopathological features of the disease are alterations of cytokine production, fibroblast activation, vascular expansion, and leukocyte infiltration in the dermis and epidermis. Dysregulation in cytokine production from both activated cells in the dermis and the immune cells seems to play an important role in mediating the inflammatory events associated with psoriasis. To this end, a number of changes in gene and/or protein expression have been described previously in psoriasis and some of these genes and/or proteins have also been found to be associated with other inflammatory diseases. These include proinflammatory cytokines such as IL-1 and TNFα, adhesion molecules, such as intercellular adhesion molecule 1 (ICAM1) and vascular adhesion molecule 1 (VCAM1), chemokines, and defensins. Recently, gene expression microarray technology has been applied to profile gene expression patterns in normal versus psoriatic lesional skins on a more inclusive scale and has provided new insights into the pathogenesis of psoriasis.

cDNA microarray technology provides a format for the simultaneous measurement of the expression level of thousands of genes in a single hybridization assay. It is also amenable to an automated, high-throughput format. More importantly, microarray technology can be used to discover new genes, quantify and analyze gene expression and assign functionality to genes with unknown function. With the complete sequencing of the human genome, identification and cloning of new genes is now accomplished rapidly. However, the understanding of whether these genes encode new proteins and the further identification of the function of these new proteins have not advanced as rapidly. The impediment has become one of the main reasons for the use of high throughput cDNA microarray technology in a well-designed experimental setting to discover novel protein-encoding genes or genes with novel functions that may subsequently become potential therapeutic targets for a variety of human diseases.

Accordingly, there is a need to provide new polypeptides, polynucleotides, antibodies, or fragments thereof and uses thereof relevant to diseases and conditions, as well as improvements over known polypeptides, polynucleotides, antibodies or fragments thereof.

SUMMARY OF THE INVENTION

The present invention relates to an isolated CNGH0010 polypeptide having the sequence shown in one of SEQ ID NOS:3, 5, 7, 9, 11, and 41, variants, for example, those based on differential exon splicing as described in Table 2 below, and fragments thereof. Another aspect of the invention is an isolated polynucleotide comprising the sequence shown in one of SEQ ID NOS:2, 4, 6, 8, 10, and 40, variants (e.g., those based on differential exon splicing as described in Table 2 below) and fragments thereof, and complementary sequences. Another aspect of the invention is an isolated polynucleotide comprising a polynucleotide encoding the amino acid sequence shown in one of SEQ ID NOS:3, 5, 7, 9, 11, and 41, variants (e.g., those based on differential exon splicing as described in Table 2 below) and fragments thereof, and complementary sequences.

The invention also relates to isolated polypeptides having at least 70%, preferably, 75%, 80%, 90%, 95%, 99%, or 100% amino acid sequence identity to any of the amino acid sequences of SEQ ID NOS:3, 5, 7, 9, 11, and 41, variants, or fragments thereof, isolated polynucleotides having at least 70%, preferably, 75%, 80%, 90%, 95%, 99%, or 100% nucleic acid sequence identity to any of the polynucleotide sequences of SEQ ID NOS:2, 4, 6, 8, 10, and 40, variants, complementary sequences, or fragments thereof, and isolated polynucleotides having at least 70%, preferably, 75%, 80%, 90%, 95%, 99%, or 100% nucleic acid sequence identity to the polynucleotides encoding any of the amino acid sequences of SEQ ID NOS:3, 5, 7, 9, 11, and 41, and variants, complementary sequences, or fragments thereof.

The present invention also provides isolated nucleic acid molecules hybridizing to (a) a nucleic acid molecule encoding a polypeptide which has at least 70% amino acid sequence identity to an amino acid sequence of one of SEQ ID NOS:3, 5, 7, 9, 11, and 41, variants, and fragments thereof, or (b) a nucleic acid molecule having at least 70% sequence identity to any of the polynucleotide sequences of SEQ ID NOS:2, 4, 6, 8, 10, and 40, variants, and fragments thereof, and complementary nucleic acids. The present invention further provides recombinant vectors comprising the polypeptide encoding nucleic acid molecules, host cells containing such nucleic acids and/or recombinant vectors, as well as methods of making and/or using such nucleic acids, vectors and/or host cells.

In another aspect, the present invention relates to antibodies and antibody fragments capable of binding to (a) a polypeptide having at least 70% amino acid sequence identity to all or part of an amino acid sequence of one of SEQ ID NOS:3, 5, 7, 9, 11, and 41 or variants, or (b) a polypeptide encoded by a polynucleotide having at least 70% nucleic acid identity to all or part of any of the polynucleotide sequences of SEQ ID NOS:2, 4, 6, 8, 10, and 40 or variants. In addition, the invention comprises antibody compositions, formulations, devices, and transgenic mice and plants. The present invention also provides methods for generating and characterizing human, primate, rodent, mammalian, chimeric, single chain, humanized and/or CDR-grafted anti-CNGH0010 antibodies, immunoglobulins, cleavage products and other specified portions and variants thereof The present invention further provides at least one CNGH0010 anti-idiotype antibody to at least one CNGH0010 antibody of the present invention.

The nucleic acid sequences encoding CNGH0010 polypeptides, or fragments thereof, can be operably linked to a nucleic acid sequence encoding a heterologous amino acid sequence to form a fusion protein. A further embodiment is a mimetibody which comprises at least a fragment of a CNGH0010 polypeptide fused to at least part of an immunoglobulin region. A preferred mimetidoby comprises at least one $CH_3$ region directly linked with at least one $CH_2$ region directly linked with at least one hinge region or fragment thereof optionally directly linked with at least one partial V region, directly linked with an optional linker sequence, directly linked to at least a fragment of a CNGH0010 polypeptide, optionally, further directly linked with at least a portion of at least one variable antibody sequence. In a further preferred embodiment, the immunoglobulin is IgG1 or IgG4.

Another aspect of the invention provides recombinant expression vectors, comprising a CNGH0010 polynucleotide. In another embodiment, the invention provides isolated host cells, e.g., mammalian and non-mammalian cells, containing such a vector and/or a CNGH0010 polynucleotide. The invention also provides methods for producing a CNGH0010 polypeptide by culturing, in a suitable medium, a host cell of the invention containing a recombinant expression vector encoding a CNGH0010 polypeptide such that the polypeptide is produced.

The present invention also provides at least one method for expressing a CNGH0010 polypeptide, anti-CNGH0010 antibody, or CNGH0010 anti-idiotype antibody, in a host cell, comprising culturing a host cell as described herein under conditions wherein at least one such CNGH0010 polypeptide, anti-CNGH0010 antibody or CNGH0010 anti-idiotype antibody is expressed in detectable and/or recoverable amounts.

In yet another aspect, the present invention provides a fusion protein comprising a polypeptide which has at least 70%, preferably, 75%, 80%, 90%, 95%, 99%, or 100% amino acid sequence identity to an amino acid sequence of one of SEQ ID NOS:3, 5, 7, 9, 11, and 41, fused to a heterologous amino acid sequence.

The present invention also provides at least one composition comprising (a) an isolated CNGH0010 polynucleotide, polypeptide, polypeptide agonist or antagonist, antibody, and/or anti-idiotype antibody as described herein; and (b) a suitable carrier or diluent. The carrier or diluent can optionally be pharmaceutically acceptable, according to known carriers or diluents. The composition can optionally further comprise at least one further compound, protein or composition.

The present invention also relates to methods of treatment and/or diagnosis of CNGH0010 related diseases, such as but not limited to, psoriasis, rheumatoid arthritis, emphysema, asthma, diabetes, autoimmune thyroiditis, inflammatory bowel diseases, including Crohn's disease and ulcerative colitis, different types of dermatitis including allergic dermatitis, contact dermatitis, actinic keratosis, wound healing, scar formation, various renal diseases, various respiratory diseases, various diseases of reproductive organs, such as endometriosis, melanoma, squamous cell carcinoma, ovarian cancer, breast cancer, lung cancer, colon cancer, prostate cancer, renal cell carcinoma, Grave's diseases and other inflammatory and hyperproliferative diseases. In a preferred embodiment, the CNGH0010 related disease is an epithelial-related disease or condition such that the disease or condition impacts epithelial cells and related cells, including, without limitation, psoriasis, inflammatory bowel diseases including Crohn's disease and ulcerative colitis, different types of dermatitis (allergic dermatitis, contact dermatitis), Actinic keratosis, wound healing, scar formation, different renal diseases, different respiratory diseases, different diseases of reproductive organs such as endometriosis, melanoma, squamous cell carcinoma, ovarian cancer, breast cancer, lung cancer, colon cancer, prostate cancer, renal cell carcinoma, emphysema, Grave's disease, diabetes, pemphigus, bullous pemphigoid, Herpes, Linear IgA disease, drug eruption, epidermolysis bullosa, stomatitis, aphthous ulcer, peptic ulcers, gastric polyposis, chronic obstructive pulmonary diseases, bronchiectasis, cystic fibrosis, renal cystic disease, cystitis, and other inflammatory and hyperproliferative diseases. The methods utilize (1) an isolated polypeptide comprising at least one of the sequences selected from SEQ ID NOS:3, 5, 7, 9, 11, and 41, variants, derivatives, and fragments thereof, (2) an isolated polynucleotide comprising at least one of the sequences of SEQ ID NOS:2, 4, 6, 8, 10, and 40, variants, derivatives, and fragments thereof, and complementary sequences, (3) an isolated polypeptide encoded by a polynucleotide comprising at least one of the sequences of SEQ ID NOS:2, 4, 6, 8, 10, and 40, variants and fragments thereof, and (4) agonists and antagonists to such polypeptides and nucleotide to diagnose and/or treat inflammatory and hyperproliferative diseases and conditions. The present invention also provides methods of treatment and/or diagnosis of CNGH0010 related diseases utilizing a CNGH0010 agonist or antagonist, anti-CNGH0010 antibody and/or CNGH0010 anti-idiotype antibody.

The present invention further provides any invention described herein.

DESCRIPTION OF THE FIGURES

FIG. 8A shows the exons 1 and 2 specific riboprobe; FIG. 8B shows the exons 18-23 specific riboprobe.

DESCRIPTION OF THE INVENTION

Figure 1:
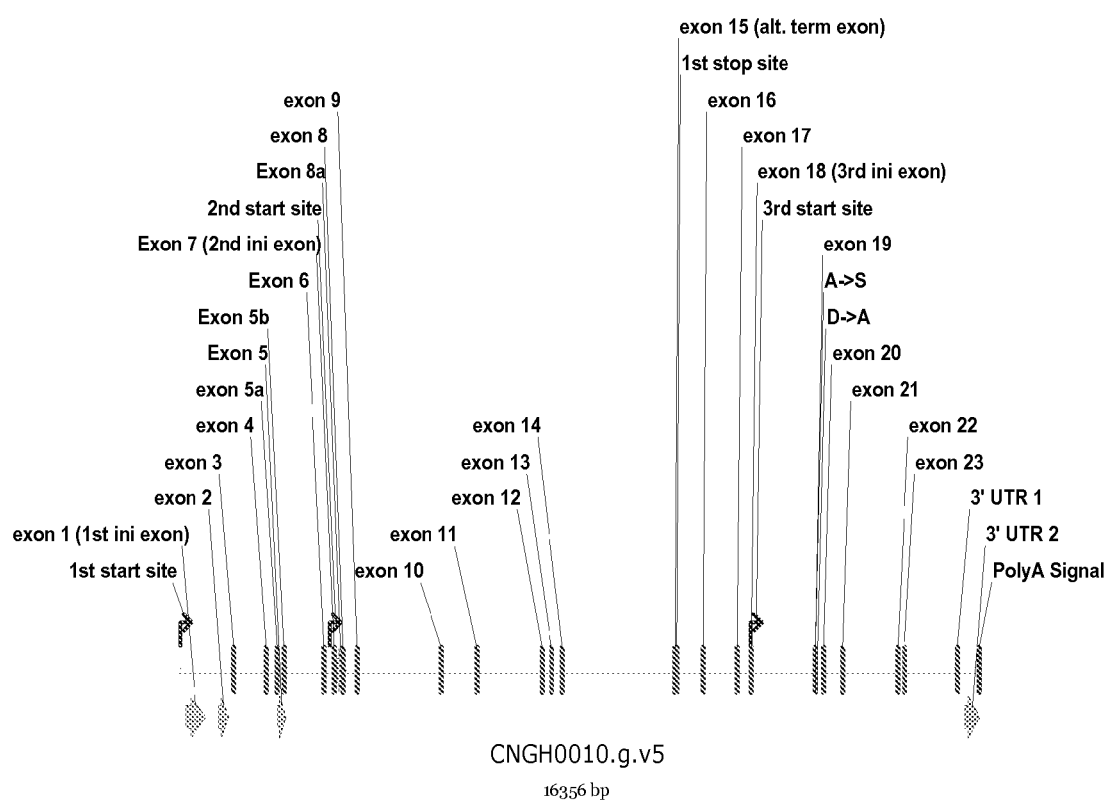
FIG. 1 shows the genomic structure of the CNGH0010 gene with exons being represented by vertical lines and the transcription start sites represented by curved arrows.

As used herein, "CNGH0010 polypeptide(s) or protein(s)," or "polypeptide(s) or protein(s) of the invention" encompass isolated polypeptides comprising at least one of the sequences selected from SEQ ID NOS:3, 5, 7, 9, 11, and 41, variants, derivatives, and fragments thereof. "CNGH0010 nucleic acids, polynucleotide(s), or gene(s)," or "nucleic acids, polynucleotide(s), or gene(s) of the invention" refer to isolated polynucleotides comprising at least one of the sequences of SEQ ID NOS:2, 4, 6, 8, 10, and 40, variants, derivatives, and fragments thereof, and complementary sequences.

Splice variants of the CNGH0010 protein and nucleic acids encoding these variants have been identified in epithelial cell types through use of RACE, RT-PCR, and Northen blot techniques. The exons and untranslated regions of the genomic CNGH0010 DNA sequence (SEQ ID NO: 1) were identified (Table 1). As shown in Table 2, the CNGH0010 gene has multiple possible variants as a result of differential transcription initiation and termination sites, i.e., alternative splicing. The primary variants are labeled CNGH0010.1, CNGH0010.2, CNGH0010.3, CNGH0010.4, CNGH0010.5, and truncated CNGH0010.2 (represented by SEQ ID NOS:2, 4, 6, 8, 10, and 40 (nucleic acids) and 3, 5, 7, 9, 11, and 41 (amino acids), respectively). Additional variants of the invention are encompassed by different combinations of exons as seen in analysis of the genomic sequence and RT-PCR products. This is demonstrated in Table 2 as shown by the exons that may be added or deleted to the coding sequences.

RT-PCR analysis of CNGH0010 transcripts present in A431 cells indicate that the CNGH0010.1 transcripts are heterogeneous with regard to the presence or absence of at least exons 11 and 20, whereas the CNGH0010.2 transcripts have heterogeneity with regard to exon 9. Also, CNGH0010.4 transcripts are heterogeneous with regard to the presence or absence of exons 9, 10, 11, and 12.

The similarities of the CNGH0010 molecules to extracellular matrix molecules (collagens) and cytokines (adiponectin) suggest that they may participate in the regulation of cell-cell or cell-matrix interactions, or bind to or influence the binding of a cytokine to a receptor. Both types of activities would ultimately influence the proliferation, migration, and differentiation status of cells and tissues. Therefore, proteins and polynucleotides of the invention represent ideal targets for therapeutic intervention using monoclonal antibodies, synthetic polypeptides, small molecule drugs, or other natural or synthetic drugs.

Accordingly, the present invention provides novel amino acid and nucleic acid sequences identified as the CNGH0010 protein and gene. The sequences comprise an isolated polypeptide comprising a polypeptide having the sequence shown in one of SEQ ID NOS:3, 5, 7, 9, 11, and 41 or variants thereof; an isolated polynucleotide comprising a polynucleotide having the sequence shown in one of SEQ ID NOS:2, 4, 6, 8, 10, and 40 or a complementary sequence; an isolated polynucleotide comprising a polynucleotide encoding the amino acid sequence shown in one of SEQ ID NOS:3, 5, 7, 9, 11, and 41 or a complementary sequence; isolated polypeptides comprising a polypeptide having at least 70% amino acid sequence identity to any of the amino acid sequences of SEQ ID NOS:3, 5, 7, 9, 11, and 41 or variants thereof; isolated polynucleotides having at least 70% nucleic acid sequence identity to any of the polynucleotide sequences of SEQ ID NOS:2, 4, 6, 8, 10, and 40, complementary sequences, or variants thereof; isolated polynucleotides having at least 70% nucleic acid sequence identity to the polynucleotides encoding any of the amino acid sequences of SEQ ID NOS:3, 5, 7, 9, 11, and 41, complementary sequences, or variants thereof; and isolated nucleic acid molecules hybridizing to a nucleic acid molecule encoding a polypeptide which has at least 70% amino acid sequence identity to an amino acid sequence of one of SEQ ID NOS:3, 5, 7, 9, 11, and 41, a nucleic acid molecule having at least 70% sequence identity to any of the polynucleotide sequences of SEQ ID NOS:2, 4, 6, 8, 10, and 40, or complementary nucleic acids; and fragments of these polypeptide and polynucleotide sequences.

As used herein, "identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in (Computational Molecular Biology, Lesk, A. M., ed., Oxford University Press, New York, 1988; Biocomputing:Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990). The BLAST X program is publicly available from NCBI and other sources (BLAST Manual, Altschul, S., et al., NCBINLM NIH Bethesda, Md. 20894: Altschul, S., et al., J. Mol. Biol. 215: 403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3

Available as: The "gap" program from Genetics Computer Group, Madison Wis. These are the default parameters for nucleic acid comparisons.

By way of example, a polynucleotide sequence of the present invention may be identical to the sequence of SEQ ID NO:2, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:2 by the numerical percent of the respective percent identity (divided by 100) and subtracting that product from the total number of nucleotides in SEQ ID NO:2, or:

$n_n \le x_n - (x_n \cdot y)$, wherein $n_n$ is the number of nucleotide alterations, $x_n$ is the total number of nucleotides in SEQ ID NO:2, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the polypeptide of SEQ ID NO:3 may create nonsense, missense or frameshift mutations in this coding sequence and thereby alter the polypeptide encoded by the polynucleotide following such alterations. Similarly, a polypeptide sequence of the present invention may be identical to the reference sequence of SEQ ID NO:3, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitutions, or insertions, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:3 by the numerical percent of the respective percent identity (divided by 100) and then subtracting that product from the total number of amino acids in SEQ ID NO:3, or:

$n_a \le x_a - (x_a \cdot y)$, wherein $n_a$ is the number of amino acid alterations, $x_a$ is the total number of amino acids in SEQ ID NO:3, and y is, for instance, 0.70 for 70%, 0.80 for 80%, 0.85 for 85% etc., and wherein any non-integer produce of $x_a$ and y is rounded down to the nearest integer prior to subtracting it from $x_a$.

As used herein, a "fragment" is a variant polypeptide having an amino acid sequence that is entirely the same as part but not all of any amino acid sequence of any polypeptide of the invention or a variant polynucleotide having a nucleic acid sequence that is entirely the same as part but not all of any nucleic acid sequence of any polynucleotide of the invention. Fragments can include, e.g., truncation polypeptides having a portion of an amino acid sequence as shown in the amino acid sequences of SEQ ID NOS:3, 5, 7, 9, 11, or 41 or of variants thereof, such as a continuous series of residues that include a heterologous amino- and/or carboxy-terminal amino acid sequence. Degradation forms of the polypeptides of the invention produced by or in a host cell are also included. Other exemplary fragments are characterized by structural or functional attributes, such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions.

Further exemplary fragments include an isolated polypeptide comprising an amino acid sequence having at least 15, 20, 30, 40, 50 or 100 contiguous amino acids from the amino acid sequence set forth in SEQ ID NOS:3, 5, 7, 9, 11 or 41 and variants, or an isolated polypeptide comprising an amino acid sequence having at least 15, 20, 30, 40, 50 or 100 contiguous amino acids truncated or deleted from the amino acid sequence set forth in amino acid sequence shown in SEQ ID NOS:3, 5, 7, 9, 11, or 41 and variants. Fragments also include isolated polynucleotides having similar sizes and characteristics.

The polypeptides and derivatives of the invention are useful as agents to inhibit the binding of the CNGH0010 polypeptide to its ligand and reduce or block subsequent signal transduction. The polypeptides and polypeptide constructs can be used as immunogens or as binding partners useful for generating, selecting, and characterizing human, primate, rodent, mammalian, chimeric, single chain, humanized and/or CDR-grafted anti-CNGH0010 antibodies, immunoglobulins, cleavage products and other specified portions and variants thereof. In addition, the antibody amino acid sequences, and encoding nucleic acid molecules comprising at least one polynucleotide encoding at least one anti-CNGH0010antibody or anti-idiotype antibody can be determined by methods well-known in the art and as described herein.

At least one human CNGH0010 polypeptide sequence as described herein is antigenic and offers a method for the generation of anti-CNGH0010 antibodies. The polypeptides described herein comprise a new class of CNGH0010 antigens that contain critical epitopes for diagnostic and therapeutic CNGH0010 antibodies. The polypeptides can be synthesized as described herein based on the amino acid sequence of the human CNGH0010 polypeptide sequences of the invention.

The CNGH0010 polypeptide or anti-CNGH0010 antibody can be incorporated into a method or composition for administering a therapeutically or prophylactically effective amount to modulate or treat at least one CNGH0010-related condition in a cell, tissue, organ, animal or patient and/or, prior to, subsequent to, or during a related condition, as known in the art and/or as described herein. The CNGH0010 polypeptide or anti-CNGH0010 antibody can be incorporated into a method or composition for diagnosing at least one CNGH0010-related condition in a cell, tissue, organ, animal or patient and/or, prior to, subsequent to, or during a related condition, as known in the art and/or as described herein.

The CNGH0010 polypeptide or anti-CNGH0010 antibody can be incorporated into a method for diagnosing or treating a CNGH0010-related condition in a cell, tissue, organ or animal, comprising contacting or administering a composition comprising an effective amount of at least one isolated CNGH0010 polypeptide or anti-CNGH0010 antibody composition of the invention with, or to, the cell, tissue, organ or animal. The method can optionally further comprise using an effective amount of 0.001-50 mg/kilogram of the polypeptide or antibody. The method can optionally further comprise treating the CNGH0010-related condition with the polypeptide or antibody by administering the polypeptide or antibody by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

The present invention provides for novel proteins and polypeptides from CNGH0010's receptor binding region that can be used to generate anti-CNGH0010 antibodies and fragments thereof First, the methods of identifying, isolating, and creating the novel polypeptides are discussed below. Then, the generation of antibodies, applications, formulations, and therapeutic treatments are presented.

All publications cited herein are entirely incorporated herein by reference, whether or not specifically designated accordingly, as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

A human CNGH0010 polypeptide of the present invention includes those of SEQ ID NOS:3, 5, 7, 9, 11, and 41 and their variants, including, without limitation, alternative splice variants, and can include one or more amino acid substitutions, deletions or additions, either from natural mutations or human manipulation, as specified herein. Such mutations or substitutions can include muteins, whose mutations can be significant enough to alter the properties of the polypeptide without altering the biological activity of the polypeptide to inhibit the binding of human CNGH0010 to its ligand. Included within the invention are CNGH0010 polypeptides having amino acid sequences in addition to those of SEQ ID NOS:3, 5, 7, 9, 11, and 41 and their variants.

Of course, the number of amino acid substitutions a skilled artisan would make depends on many factors, including those described above. Generally speaking, the number of amino acid substitutions, insertions or deletions for any given CNGH0010 polypeptide, fragment or variant will not be more than 1-5, or any range or value therein, as specified herein.

Amino acids in a CNGH0010 polypeptide of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one CNGH0010 neutralizing activity.

Synthesis of CNGH0010 Polypeptides

Polypeptides having the amino acid sequences set forth and described above, may be synthesized using standard Boc or FMOC chemistry. The resulting polypeptides can be injected as is, cross-linked, or conjugated to a carrier molecule. To facilitate conjugation to carriers, an N-terminal N-acetyl-cysteine or C-terminal amides can be formed and the C-terminal amino acid can be amidated. A variety of linking groups may be interspaced between the polypeptide and the carrier molecule to allow for proper conformational folding and presentation of the antigenic polypeptide.

It is envisioned that the CNGH0010 polypeptides of this invention may also be produced by cell lines derived from bacteria, yeast, insect, or mammal. Recombinant expression cassettes comprising the nucleic acids encoding the novel polypeptides can be introduced into at least one host cell. Vectors containing the CNGH0010 nucleic acid sequence and necessary promoter elements may be used to express CNGH0010 polypeptides. Nucleic acid sequences encoding a CNGH0010 polypeptide in conjunction with a signal peptide may be included to facilitate secretion and purification of desired polypeptides. Those of ordinary skill in the art are knowledgeable in the numerous expression systems available for expression of a nucleic acid encoding a polypeptide of the present invention. Cell-free translation systems can also be employed to produce such polypeptides using RNAs derived from the DNA constructs of the invention.

Nucleic Acid Molecules

Nucleic acid sequences encoding human CNGH0010 polypeptides of the present invention may be obtained by cloning, for example, by RT-PCR amplification of RNA samples. Alternatively, the DNA encoding CNGH0010 polypeptides may be obtained by DNA synthesis or from any cDNA library prepared from tissues believed to possess the CNGH0010 mRNA or from a genomic DNA library. The nucleic acid sequences can be cloned by PCR amplification or by traditional methods of DNA hybridization and expression cloning.

Using the information provided herein (methods described herein or as known in the art), such as the nucleotide sequences encoding at least 70-100% of the contiguous amino acids of at least one of SEQ ID NOS:3, 5, 7, 9, 11, and 41 or specified fragments, variants or consensus sequences thereof, or a vector comprising at least one of these sequences, a nucleic acid molecule of the present invention encoding at least one CNGH0010 polypeptide or anti-CNGH0010 antibody can be obtained.

Nucleic acid molecules of the present invention can be in the form of RNA, such as mRNA, hnRNA, or any other form, or in the form of DNA, including, but not limited to, cDNA and genomic DNA obtained by cloning or produced synthetically, or any combinations thereof The DNA can be triple-stranded, double-stranded or single-stranded, or any combination thereof Any portion of at least one strand of the DNA or RNA can be the coding strand, also known as the sense strand, or it can be the non-coding strand, also referred to as the anti-sense strand.

As indicated herein, nucleic acid molecules of the present invention which comprise a nucleic acid encoding a CNGH0010 polypeptide or anti-CNGH0010 antibody can include, but are not limited to, those encoding the amino acid sequence of a polypeptide or antibody fragment, by itself, the coding sequence for the entire polypeptide or antibody or a portion thereof, the coding sequence for a polypeptide or antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); and an additional coding sequence that codes for additional amino acids, such as those that provide additional functionalities. Thus, the sequence encoding a polypeptide or antibody can be fused to a marker sequence, such as a sequence encoding a peptide that facilitates purification of the fused antibody comprising an antibody fragment or portion thereof.

Construction of Nucleic Acids and Expression and Purification of Polypeptides

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

A great variety of expression systems can be used to produce the polypeptides of the invention. Such systems include chromosomal-, episomal- and virus-derived vectors, such as vectors derived from bacterial plasmids, bacteriophage, transposons, yeast episomes, insertion elements, yeast chromosomal elements, baculoviruses, papova viruses, such as SV40, vaccinia viruses, adenoviruses, fowl pox viruses, pseudorabies viruses, picornaviruses and retroviruses and vectors derived from combinations thereof, such as cosmids and phagemids. The expression system constructs may contain control regions that regulate or cause expression. Generally, any system or vector suitable to maintain or propagate polynucleotides and/or to express polypeptides in a host may be used for expression. An appropriate DNA sequence may be inserted into the expression system by any of a variety of techniques well known to those skilled in the art, such as, e.g., those set forth in Sambrook et al, supra.

In eukaryotic expression systems, polypeptides of the invention can be secreted into the lumen of the endoplasmic reticulum or extracellular environment by inclusion of appropriate secretion signals, such as a signal peptide or leader sequence.

Polypeptides of the invention can be recovered and purified from recombinant cell cultures by well-known methods, including ammonium sulfate or ethanol precipitation, acid extraction, high-performance liquid chromatography, anion or cation exchange chromatography, phosphocellulose chromatography, hydrophobic interaction chromatography, affinity chromatography, hydroxyapatite chromatography and lectin chromatography. Well-known techniques for refolding protein may be employed to regenerate an active conformation when the protein is denatured during isolation and/or purification.

In an alternate method of obtaining the nucleic acid of the invention, encoding the CNGH0010 polypeptides, a cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide.

For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 80-100%, or any range or value therein. However, it should be understood that minor sequence variations in the probes and primers can be compensated for by reducing the stringency of the hybridization and/or wash medium. An example of stringent hybridization conditions includes overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091, 310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990).

Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Polynucleotides Selectively Hybridizing to a Polynucleotide as Described

As described above, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of a protein or an antibody encoded by the polynucleotides described herein. The polynucleotides of this invention embrace nucleic acid sequences that can be employed for selective hybridization to a polynucleotide encoding a protein or an antibody of the present invention. See, e.g., Ausubel, supra; Colligan, supra, each entirely incorporated herein by reference.

Use of CNGH0010 Polypeptides and Polynucleotides

The polynucleotides and polypeptides of the invention are also useful for assaying a medium for the presence of a substance that modulates CNGH0010 protein function by affecting the binding of a CNGH0010 analog protein to cellular binding partners, such as the CNGH0010 receptor. Examples of modulators include polypeptides or small organic molecules.

Polypeptides of the invention may also be used to identify lead compounds for drug development. The structure of the polypeptides described herein can be readily determined by a number of methods such as NMR and X-ray crystallography. A comparison of the structures of polypeptides similar in sequence, but differing in the biological activities that they elicit in target molecules can provide information about the structure-activity relationship of the target. Information obtained from the examination of structure-activity relationships can be used to design either modified polypeptides, or other small molecules or lead compounds which can be tested for predicted properties as related to the target molecule. The activity of the lead compounds can be evaluated using assays similar to those described herein.

Information about structure-activity relationships may also be obtained from co-crystallization studies. In these studies, a polypeptide with a desired activity is crystallized in association with a target molecule, and the X-ray structure of the complex is determined. The structure can then be compared to the structure of the target molecule in its native state, and information from such a comparison may be used to design compounds expected to possess desired activities.

The invention also contemplates methods for identifying novel compounds that bind to the polypeptides of the invention thereby affecting a CNGH0010-signaling pathway. Protein-protein interactions may be identified using conventional methods such as co-immunoprecipitation, crosslinking and co-purification through gradients or chromatographic columns. Methods may also be employed that result in the simultaneous identification of genes which encode proteins interacting with a molecule. These methods include probing expression libraries with labeled molecules. Additionally, x-ray crystallographic studies may be used as a means of evaluating interactions with substances and molecules.

It will be appreciated that fusion proteins and recombinant proteins may be used in the above described methods. The reagents suitable for applying the methods of the invention to evaluate substances and compounds that affect or modulate a CNGH0010 signaling pathway may be packaged into convenient kits providing the necessary materials packaged into suitable containers. The kits may also include suitable supports useful in performing the methods of the invention.

Mature CNGH0010 or its analogs can be used to modulate, i.e., increase or decrease, eukaryotic cell activity and/or number, such as proliferation and activation. Moreover, mature CNGH0010 or its analogs can be used to regulate cell differentiation and migration. Since CNGH0010 can be secreted, mature CNGH0010 or its analogs can also be used to treat various kinds of immune-mediated inflammatory diseases that are dependent on cell proliferation, differentiation, and migration, such as but not limited to, psoriasis, rheumatoid arthritis, emphysema, asthma, diabetes, autoimmune thyroiditis, inflammatory bowel diseases, including Crohn's disease and ulcerative colitis, different types of dermatitis including allergic dermatitis, contact dermatitis, actinic keratosis, wound healing, scar formation, various renal diseases, various respiratory diseases, various diseases of reproductive organs, such as endometriosis, melanoma, squamous cell carcinoma, ovarian cancer, breast cancer, lung cancer, colon cancer, prostate cancer, renal cell carcinoma, Grave's diseases and other inflammatory and hyperproliferative diseases. In addition, mature CNGH0010 or its analogs can be used to enhance immune responses to an infectious disease. Mature CNGH0010 or its analogs can be used alone or in combination with an antigen as an adjuvant to treat or prevent various infectious, hyperprolifeative and inflammatory diseases.

The mode of administration for therapeutic use of the polypeptides of the invention may be any suitable route that delivers the agent to the host, such as parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Polypeptides of the invention may be prepared as pharmaceutical compositions containing an effective amount of the binding agent as an active ingredient in a pharmaceutically acceptable carrier. An aqueous suspension or solution containing the binding agent, preferably buffered at physiological pH, in a form ready for injection is preferred. The compositions for parenteral administration will commonly comprise a solution of the binding agent of the invention or a cocktail thereof dissolved in a pharmaceutically acceptable carrier, preferably, an aqueous carrier. A variety of aqueous carriers may be employed, e.g., 0.4% saline, 0.3% glycine and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions, such as pH adjusting and buffering agents, etc. The concentration of the polypeptides of the invention in such pharmaceutical formulations can vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g., about 50 ng to about 30 mg or more, preferably, about 5 mg to about 25 mg, of a polypeptide of the invention. Similarly, a pharmaceutical composition of the invention for intravenous infusion could be made up to contain about 250 ml of sterile Ringer's solution, and about 1 mg to about 30 mg and preferably 5 mg to about 25 mg of a polypeptide of the invention. Actual methods for preparing parenterally administrable compositions are well known or will be apparent to those skilled in the art and are described in more detail in, for example, *Remington, the Science and Practice of Pharmacy*, 19th ed., Mack Publishing Company, Easton, Pa. (1995).

The polypeptides of the invention, when in a pharmaceutical preparation, can be present in unit dose forms. The appropriate therapeutically effective dose can be determined readily by those of skill in the art. A determined dose may, if necessary, be repeated at appropriate time intervals that are selected as appropriate by a physician during the treatment period.

The polypeptides of the invention can be lyophilized for storage and reconstituted in a suitable carrier prior to use. This technique has been shown to be effective with conventional protein preparations and lyophilization and reconstitution techniques known in the art can be employed.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cell must first be lysed before the polypeptide is recovered.

This invention also relates to the use of polynucleotides of the present invention as diagnostic reagents. Detection of a mutated form of the gene characterized by the polynucleotide of SEQ ID NO:2 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled CNGH0010 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85:4397-4401). In another embodiment, an array of oligonucleotides probes comprising CNGH0010 nucleotide sequences or fragments thereof can be constructed to conduct efficient screening of e.g., genetic mutations. Array technology methods are well known and have general applicability and can be used to address a variety of questions in molecular genetics, including gene expression, genetic linkage, and genetic variability (see for example: M. Chee et al., Science, Vol 274, pp 610-613 (1996)).

The diagnostic assays offer a process for diagnosing or determining a susceptibility to the relevant diseases through detection of mutation in the CNGH0010 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance, PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably, one of the nucleotide sequences of SEQ ID NOS:2, 4, 6, 8, 10, and 40 and variants, polynucleotides with at least 70% identity to any of SEQ ID NOS:2, 4, 6, 8, 10, and 40 or variants, or a fragment thereof, (b) a nucleotide sequence complementary to that of (a);

(c) a polypeptide of the present invention, preferably, one of the polypeptides of SEQ ID NOS:3, 5, 7, 9, 11, and 41 and variants, polypeptides with at least 70% identity to any of SEQ ID NOS:3, 5, 7, 9, 11, and 41 and variants, or a fragment thereof, or (d) an antibody to a polypeptide of the present invention, variants, and fragments thereof, preferably, to one of the polypeptides of SEQ ID NOS:3, 5, 7, 9, 11, and 41 and variants.

It will be appreciated that in any such kit, components (a), (b), (c), or (d) from above may comprise a substantial component. Such a kit will be of use in diagnosing a disease or susceptibility to a disease, such as but not limited to, psoriasis, rheumatoid arthritis, emphysema, asthma, diabetes, autoimmune thyroiditis, inflammatory bowel diseases including Crohn's disease and ulcerative colitis, various types of dermatitis including allergic dermatitis, contact dermatitis, actinic keratosis, wound healing, scar formation, various renal diseases, various respiratory diseases, various diseases of reproductive organs, such as endometriosis, melanoma, squamous cell carcinoma, ovarian cancer, breast cancer, lung cancer, colon cncer, prostate cancer, renal cell carcinoma, Grave's diseases and other inflammatory and hyperproliferative diseases.

The nucleotide sequences of the present invention are also valuable for chromosome identification. Each genomic sequence is specifically targeted to, and can hybridize with, a particular location on an individual human chromosome. The mapping of relevant sequences to chromosomes according to the present invention may be useful in correlating those sequences with gene-associated diseases and conditions. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region can then be identified through linkage analysis (i.e., coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease. The polynucleotides, polypeptides and antibodies to the polypeptides of the present invention may also be used to configure screening methods for detecting the effect of added compounds on the production of mRNA and polypeptide in cells. For example, an ELISA assay may be constructed for measuring secreted or cell-associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques, such as surface plasmon resonance and spectroscopy. These screening methods may also be used to identify agonists and antagonists of the polypeptide that compete with the binding of the polypeptide to its receptors, if any. Standard methods for conducting these assays are well understood in the art.

Examples of potential polypeptide antagonists include antibodies or, in some cases, oligonucleotides or proteins which are closely related to the ligands, substrates, receptors, enzymes, etc., of the polypeptide. For example, a fragment of the ligands, substrates, receptors, enzymes, etc.; or small molecules may bind to the polypeptide of the present invention but may not elicit a response, i.e., to the activity of the polypeptide.

Thus in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:
(a) a polypeptide of the present invention;
(b) a recombinant cell expressing a polypeptide of the present invention;
(c) a cell membrane expressing a polypeptide of the present invention; or
(d) antibody to a polypeptide of the present invention, which polypeptide is preferably one of SEQ ID NOS:3, 5, 7, 9, 11, and 41 or splice variants.

It will be appreciated that in any such kit, components (a), (b), (c), or (d) may comprise a substantial component.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

It will be further appreciated that this will normally be an interactive process.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of retroviral plasmid vector. The cells are then introduced into the subject.

Anti-CNGH0010 Antibodies

An antibody of the invention binds at least one specified epitope specific to a CNGH0010 protein, subunit, fragment, portion of the invention, or any combination thereof. The epitope can comprise an antibody binding region that comprises at least one portion of the amino acid sequence of SEQ ID NOS:3, 5, 7, 9, 11, and 41 or its variants (e.g., splice variants described below), which epitope is preferably comprised of at least 1-5 amino acids of the sequences. The antibody can include or be derived from any mammal, such as, but not limited to, a human, a mouse, a rabbit, a rat, a rodent, a primate, or any combination thereof, and the like.

An anti-CNGH0010 antibody, as described herein, has at least one activity, such as, but not limited to neutralizing CNGH0010-dependent receptor phosphorylation, receptor internalization, cell adhesion, migration and invasion, and induction of signaling molecules or adaptation of cell markers. An anti-CNGH0010 antibody can thus be screened for a corresponding activity according to known methods, such as but not limited to, at least one biological activity of human CNGH0010. The antibody can be used to measure or affect a cell, tissue, organ or animal (including mammals and humans), to diagnose, monitor, modulate, treat, alleviate, help prevent the incidence of, or reduce the symptoms of, at least one CNGH0010-related disease or condition, selected from, but not limited to, at least one of an immune disorder or disease, a cardiovascular disorder or disease, an infectious, malignant, and/or neurologic disorder or disease, or other known or specified CNGH0010-related condition.

Definition & Characterization of an Anti-CNGH0010 Antibody

As used herein, an "anti-CNGH0010 antibody," "anti-CNGH0010 antibody portion," or "anti-CNGH0010 antibody fragment" and/or "anti-CNGH0010 antibody variant" and the like include any protein or polypeptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a CNGH0010 receptor or binding protein derived from a CNGH0010 protein or polypeptide of the invention, which can be incorporated into an antibody of the present invention. Such antibody optionally further affects a specific ligand, such as but not limited to, where such antibody modulates, decreases, increases, antagonizes, angonizes, mitigates, alleviates, blocks, inhibits, abrogates and/or interferes with at least one CNGH0010 activity or binding, or with CNGH0010 ligand activity or binding, in vitro, in situ and/or in vivo. As a non-limiting example, a suitable anti-CNGH0010 antibody, specified portion or variant of the present invention can bind at least one CNGH0010 protein or polypeptide of the invention, or specified portions, variants or domains thereof. A suitable anti-CNGH0010 antibody, specified portion, or variant can also optionally affect at least one of CNGH0010 activity or function, such as but not limited to, RNA, DNA or protein synthesis, CNGH0010 release, CNGH0010 receptor signaling, CNGH0010 activity, CNGH0010 production and/or synthesis.

The term "antibody" is further intended to encompass antibodies, digestion fragments, specified portions and variants thereof, including antibody mimetics or portions of antibodies that mimic the structure and/or function of an antibody or specified fragment or portion thereof, including single chain antibodies and fragments thereof. Functional fragments include antigen-binding fragments that bind to a mammalian CNGH0010. For example, antibody fragments capable of binding to CNGH0010 or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, CL, CH domains (e.g., $CH_1$, $CH_2$, $CH_3$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies of the invention can include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, a Fv can comprise a linker peptide, such as 2 to about 8 glycine or other amino acid residues, which connects the variable region of the heavy chain and the variable region of the light chain. Such linker peptides are considered to be of human origin.

The isolated antibodies of the present invention comprise any isolated or prepared antibody prepared as described herein. Preferably, the human antibody or antigen-binding fragment binds human CNGH0010 and, thereby, partially or substantially neutralizes at least one biological activity of the protein. An antibody, or specified portion or variant thereof, that partially or preferably substantially neutralizes at least one biological activity of at least one CNGH0010 protein or fragment can bind the protein or fragment and thereby inhibit activities mediated through the binding of CNGH0010 to the CNGH0010 receptor or through other CNGH0010-dependent or mediated mechanisms. As used herein, the term "neutralizing antibody" refers to an antibody that can inhibit a CNGH0010-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-CNGH0010 antibody to inhibit a CNGH0010-dependent activity is preferably assessed by at least one suitable CNGH0010 protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4. Antibodies of this type can be prepared by employing a transgenic mouse or other trangenic non-human mammal comprising at least one human light chain (e.g., IgG, IgA and IgM (e.g., $\gamma1$, $\gamma2$, $\gamma3$, $\gamma4$) transgenes as described herein and/or as known in the art. In another embodiment, the anti-human CNGH0010 human antibody comprises an IgG1 heavy chain and an IgG1 light chain.

At least one antibody of the invention binds at least one specified epitope specific to at least one CNGH0010 protein, subunit, fragment, portion or any combination thereof, as described herein. The at least one epitope can comprise at least one antibody binding region that comprises at least one portion of the protein sequences corresponding to the peptide sequences from the receptor binding region of human CNGH0010, as described herein, which epitope is preferably comprised of at least one extracellular, soluble, hydrophilic, external or cytoplasmic portion of the protein.

Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region.

Bispecific, heterospecific, heteroconjugate or similar antibodies can also be used that are monoclonal, preferably, human or humanized, antibodies that have binding specificities for at least two different antigens. In the present case, one of the binding specificities is for at least one CNGH0010 protein of the invention, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, and 4,676,980, WO 91/00360, WO 92/00373, EP 03089, Traunecker et al., EMBO J. 10:3655 (1991), and Suresh et al., Methods in Enzymology 121:210 (1986), each entirely incorporated herein by reference.

Anti-CNGH0010 antibodies useful in the methods and compositions of the present invention can optionally be characterized by high affinity binding to CNGH0010 and, optionally and preferably, having low toxicity. In particular, an antibody, specified fragment or variant of the invention, where the individual components, such as the variable region, constant region and framework, individually and/or collectively, optionally and preferably, possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably, less than about 100 measured with a double antigen enzyme immunoassay) (Elliott et al., Lancet 344:1125-1127 (1994), entirely incorporated herein by reference).

Application of the anti-CNGH0010 antibody can comprise administering an effective amount of a composition or a pharmaceutical composition comprising at least one anti-CNGH0010 antibody to a cell, tissue, organ, animal, or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. Lipid molecules such as a disteroylphosphatidyl ethanolamine moiety, either alone or covalently bonded to a hydrophilic polymer, are useful. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-Δ9-octadecanoate (C18, oleate), all cis-Δ5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (HS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom such as oxygen, nitrogen or sulfur. Suitable linker moieties include, for example, tetraethylene glycol, —(CH$_2$)$_3$—, —NH—(CH$_2$)$_6$—NH—, —(CH$_2$)$_2$—NH— and —CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, a NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Generation of Monoclonal Antibodies

Monoclonal antibodies of this invention may be raised by traditional immunization and hybridoma technology. After immunization of mice with human CNGH0010 antigenic compositions comprising the polypeptides of the invention, spleen cells or lymphocytes from lymph node tissue from immunized animals are recovered and immortalized by fusion with myeloma cells or by Epstein-Barr (EB)-virus transformation. Monoclonal antibodies are obtained by screening for clones expressing the desired antibody. While mice are frequently employed as the test model, it is contemplated that any mammalian subject, including human subjects or antibody-producing cells, can be manipulated according to the processes of this invention to serve as the basis for production of mammalian, including human and hybrid cell lines. Techniques for cloning recombinant DNA of antibody molecule directly from an antibody-expressing B cell are within the scope of this invention. Such B cells can be isolated by the fluorescence activated cell sorter.

While routinely, mouse monoclonal antibodies are generated, the invention is not so limited. For therapeutic applications, human or humanized antibodies are desired. Such antibodies can be obtained by using human hybridomas or by generating humanized antibodies. Humanized antibodies can be developed by replacing the specific segments of a non-human antibody with corresponding segments of a human antibody gene. This process retains most or all of CDR regions of the light and heavy chain variable regions of parental antibody and largely replaces the framework regions with human sequences [EP Patent No. 184187; EP Patent No. 171496; EP Patent No. 173494 and WO Patent No. 86/01533]. Human monoclonal antibodies are also generated in transgenic mice that contain genes or gene segments encoding human antibodies in their genome [U.S. Pat. No. 6,162,963; WO Patent No. 93/12227; U.S. Pat. Nos. 5,877, 5397; 5,874,299; 5,814,318; 5,789,650; 5,770,429; 5,661, 016; 5,625,126; 5,569,825; 5,545,806; and WO Patent No. 91/10741].

Human monoclonal antibodies are also obtained from recombinant antibody libraries, generated in vitro or in vivo, using phage display, ribosome display, or related screening or selection techniques. Examples of procedures for generating antibody libraries, primarily of human origin, are disclosed by A. Knappik and others [65] [U.S. Pat. Nos. 6,291,158; 6,291,159; 6,291,160 and 6,291,161]. Examples of methods for selections of human antibodies to specific antigen targets from such libraries are disclosed by B. Krebs and others [66] [U.S. Pat. Nos. 5,955,341; 5,759,817; 5,658,727; 6,235,469; 5,969,108; 5,886,793].

Detailed Description of Methods to Generate Anti-CNGH0010 Antibodies

At least one anti-CNGH0010 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley &

Sons, Inc., NY (1994-2001); Colligan et al., Current Protocols in Protein Science, John Wiley & Sons, NY, N.Y., (1997-2001), each entirely incorporated herein by reference.

Human antibodies that are specific for human CNGH0010 proteins (as described herein), variants, or fragments thereof can be raised against an appropriate immunogenic antigen as described herein, such as the isolated and/or CNGH0010 proteins, variants, or portions thereof (including synthetic molecules, such as synthetic polypeptides) as described herein. Other specific or general mammalian antibodies can be similarly raised. Preparation of immunogenic antigens, and monoclonal antibody production can be performed using any suitable technique.

In one approach, a hybridoma is produced by fusing a suitable immortal cell line, e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, heteromylomas, fusion products thereof, any cell or fusion cell derived therefrom, or any other suitable cell line as known in the art (See, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid molecule, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof See, e.g., Ausubel, supra, and Colligan, Immunology, supra, chapter 2, entirely incorporated herein by reference.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells that produce antibodies with the desired specificity can be selected by a suitable assay (e.g., ELISA).

Other suitable methods of producing or isolating antibodies of the requisite specificity can be used, including, but not limited to, methods that select recombinant antibody from a polypeptide or protein display library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Biolnvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350260(May 12, 1994); PCT/GB94/01422; PCT/GB94/02662; PCT/GB97/01835; (CAT/MRC); WO90/14443; WO90/14430; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., at www.ncbi.nlm.nih.gov/entrez/query.fcgi; www.atcc.org/phage/hdb.html; www.sciquest.com/;

www.abcam.com/; www.antibodyresource.com/onlinecomp.html;

www.public.iastate.edu/~pedro/research_tools.html; www.mgen.uni-heidelberg.de/SD/IT/IT.html;

www.whfreeman.com/immunology/CH05/kuby05.htm;

www.library.thinkquest.org/12429/Immune/Antibody.html;

www.hhmi.org/grants/lectures/1996/vlab/; www.path.cam.ac.uk/~mrc7/mikeimages.html;

www.antibodyresource.com/;

mcb.harvard.edu/BioLinks/Immunology.html.www.immunologylink.com;

pathbox.wustl.edu/~hcenter/index.html; www.biotech.ufl.edu/~hcl/;

www.pebio.com/pa/340913/340913.html; www.nal.usda.gov/awic/pubs/antibody/;

www.m.ehime-u.ac.jp/~yasuhito/Elisa.html; www.biodesign.com/table.asp;

www.icnet.uk/axp/facs/davies/links.html; www.biotech.ufl.edu/~fccl/protocol.html; www.isac-net.org/sites_geo.html; aximt1 imt.uni-marburg.de/~rek/AEPStart.html;

baserv.uci.kun.nl/~jraats/links1.html; www.recab.uni-hd.de/immuno.bme.nwu.edu/; www. mrc-cpe.cam.ac.uk/imt-doc/public/INTRO.html;www.ibt.unam.mx/vir/V_mice.html; imgt.cnusc.fr:8104/;

www.biochem.ucl.ac.uk/~martin/abs/index.html; antibody. bath.ac.uk/;
abgen.cvm.tamu.edu/lab/wwwabgen.html; www.unizh.ch/~honegger/AHOseminar/Slide01.html;
www.cryst.bbk.ac.uk/~ubcg07s/; www.nimr.mrc.ac.uk/CC/ccaewg/ccaewg.htm;
www.path.cam.ac.uk/~mrc7/humanisation/TAHHP.html;
www.ibt.unam.mx/vir/structure/stat_aim.html; www.biosci.missouri.edu/smithgp/index.html;
www.cryst.bioc.cam.ac.uk/~fmolina/Web-pages/Pept/spot-tech.html; www.jerini.de/fr_products.htm;
www.patents.ibm.com/ibm.html.Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to, those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos: 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567, PCT/:US98/16280, US96/18978, US91/09630, US91/05939, US94/01234, GB89/01334, GB91/01134, GB92/01755; WO90/14443, WO90/14424, WO90/14430, and EP 229246, each entirely incorporated herein by reference, included references cited therein.

The anti-CNGH0010 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-CNGH0010 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5,000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754 and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, and U.S. Pat. No. 5,698,417, assigned to Xoma, Colligan, supra; Ausubel, supra; or Sambrook, supra, each of the above patents and publications entirely incorporated herein by reference.

Antibodies of the present invention can also be prepared in milk by administering at least one anti-CNGH0010 antibody encoding nucleic acid to transgenic animals or mammals, such as goats, cows, horses, sheep, and the like, that produce antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-CNGH0010 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbiol. Immunol. 240:95-118 (1999) and references cited therein. Also, transgenic maize has been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies of the invention can bind human CNGH0010 with a wide range of affinities (KD). In a preferred embodiment, at least one human mAb of the present invention can optionally bind human CNGH0010 with high affinity. For example, a human mAb can bind human CNGH0010 with a KD equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Purification of an Antibody

An anti-CNGH0010 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Cloning and Expression of Anti-CNGH0010 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences, and intervening sequences flanked by donor and acceptor sites for RNA splicing. Highly efficient transcription can be achieved with the early and late promoters from SV40, the long terminal repeats (LTRS) from Retroviruses, e.g., GAS-6, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pGAS-6cat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Anti-Idiotype Antibodies to Anti-CNGH0010 Antibody Compositions

In addition to monoclonal or chimeric anti-CNGH0010 antibodies, the present invention is also directed to an anti-idiotypic (anti-Id) antibody specific for such antibodies of the invention. An anti-Id antibody is an antibody that recognizes unique determinants generally associated with the antigen-binding region of another antibody. The anti-Id can be prepared by immunizing an animal of the same species and genetic type (e.g., mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

CNGH0010 Polypeptide or Antibody Compositions

The present invention also provides CNGH0010 polypeptide or CNGH0010 antibody compositions comprising at least one CNGH0010 polypeptide or CNGH0010 antibodies as described herein that are provided in a non-naturally occurring composition, mixture or form. Such compositions comprise non-naturally occurring compositions comprising at least one or two full length, C- and/or N-terminally deleted variants, domains, fragments, or specified variants, of the CNGH0010 polypeptide amino acid sequence selected from the group consisting of 80-100% of the contiguous amino acids of SEQ ID NOS:3, 5, 7, 9, 11, and 41, or CNGH0010 antibody or specified fragments, domains or variants thereof, optionally, in combination with a pharmaceutically acceptable carrier or diluent.

CNGH0010 polypeptides or antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the anti-CNGH0010 antibody, fragment or variant composition as well known in the art or as described herein.

Pharmaceutical excipients and additives useful in the present composition include, but are not limited to, proteins, polypeptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-CNGH0010 polypeptide or antibody compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-CNGH0010 antibody compositions of the invention can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-CNGH0010 antibody, portion or variant compositions according to the invention are known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference. Preferrred carrier or excipient materials are carbohydrates (e.g., saccharides and alditols) and buffers (e.g., citrate) or polymeric agents.

Anti-CNGH0010 antibody compositions of the present invention can further comprise at least one of any suitable and effective amount of a composition or pharmaceutical composition comprising at least one anti-CNGH0010 antibody contacting or administering to a cell, tissue, organ, animal or patient in need of such modulation, treatment or therapy, optionally, further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquino lone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Non-limiting examples of such cytokines include, but are not limited to, any of the interleukins from IL-1 to IL-29. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci.* See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Applications

The present invention provides a method for modulating or treating at least one CNGH0010 related disease, in a cell, tissue, organ, animal, or patient, as known in the art or as described herein, using at least one CNGH0010 polypeptide or CNGH0010 antibody of the present invention.

Compositions of CNGH0010 binding polypeptides or CNGH0010 antibody or polypeptide antagonists may find therapeutic use in the treatment of disease conditions such as cancer or other human diseases with deregulated matrix production and remodeling, including lung fibrosis, liver cirrhosis, osteoporosis, rheumatoid arthritis, and asthma. Potential disease indications may also include diseases with defects in cell mechanics, tissure structure, or deregulation of mechanochemical conversion caused by pathological alteration of matrix (Ingber D., Mechanolbiology and diseases of mechanotransduction, Annals of Medicine, in press).

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

Any method of the present invention can comprise administering an effective amount of a composition or pharmaceutical composition comprising at least one anti-CNGH0010 antibody to a cell, tissue, organ, animal, or patient in need of such modulation, treatment or therapy. Such a method can optionally further comprise co-administration or combination therapy for treating such immune diseases, wherein the administration of the CNGH0010 polypeptide or CNGH0010 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquino lone, a macro lide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Typically, treatment of pathologic conditions is effected by administering an effective amount or dosage of at least one anti-CNGH0010 antibody composition that total, on average, a range from at least about 0.01 to 500 milligrams of at least one anti-CNGH0010 antibody per kilogram of patient per dose, and, preferably, from at least about 0.1 to 100 milligrams antibody/kilogram of patient per single or multiple administration, depending upon the specific activity of contained in the composition. Alternatively, the effective serum concentration can comprise 0.1-5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually, a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions, the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations

As noted above, the invention provides for stable formulations, which preferably contain a phosphate buffer with saline or a chosen salt, as well as preserved solutions and formulations containing a preservative as well as multi-use preserved formulations suitable for pharmaceutical or veterinary use, comprising at least one anti-CNGH0010 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to, 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-CNGH0010 antibody with the prescribed buffers and/or preservatives, optionally, in an aqueous diluent, wherein the packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-CNGH0010 antibody, and a second vial comprising an aqueous diluent of prescribed buffer or preservative, wherein the packaging material comprises a label that instructs a patient to reconstitute the at least one anti-CNGH0010 antibody in the aqueous diluent to form a solution that can be held over a period of twenty-four hours or greater.

The at least one anti-CNGH0010 antibody used in accordance with the present invention can be produced by recombinant means, including from mammalian cell or transgenic preparations, or can be purified from other biological sources, as described herein or as known in the art.

The range of at least one anti-CNGH0010 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-CNGH0010 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-CNGH0010 antibody and preservative in an aqueous diluent is carried out using conventional dissolution and mixing procedures. To prepare a suitable formulation, for example, a measured amount of at least one anti-CNGH0010 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized, at least one anti-CNGH0010 antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one anti-CNGH0010 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized (at least one) anti-CNGH0010 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized (at least one) anti-CNGH0010 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the (at least one) anti-CNGH0010 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-CNGH0010 antibody and a selected buffer, preferably, a phosphate buffer containing saline or a chosen salt. Mixing the (at least one) anti-CNGH0010 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized (at least one) anti-CNGH0010 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stablizing the anti-CNGH0010 antibody may result in other than a clear solution of lyophilized powder comprising the antibody. Among non-clear solutions are formulations comprising particulate suspensions, the particulates being a composition containing the anti-CNGH0010 antibody in a structure of variable dimension and known variously as a microsphere, microparticle, nanoparticle, nanosphere, or liposome. Such relatively homogenous essentially spherical particulate formulations containing an active agent can be formed by contacting an aqueous phase containing the active and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active and a polymer dispersed in a continuous solvent and removing the solvent from the suspension by freeze-drying or dilution-extraction-precipitation as taught in U.S. Pat. No. 4,818,542. Preferred polymers for such preparations are natural or synthetic copolymers or polymer selected from the group consisting of gleatin agar, starch, arabinogalactan, albumin, collagen, polyglycolic acid, polylactic aced, glycolide-L(-)lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(-)lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing the first phase through an orifice in a nozzle to effect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 99/16419. The stabilized dispersions may be administered to the lung of a patient using a metered dose inhaler. Equipment useful in the commercial manufacture of spray dried medicaments are manufactured by Buchi Ltd. or Niro Corp.

At least one anti-CNGH0010 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

EXAMPLES OF INVENTION

Having generally described the invention, the same will be more readily understood by reference to the following examples, which are provided by way of illustration and are not intended as limiting.

It will be clear that the invention can be practiced otherwise than as particularly described in the foregoing description and examples.

Numerous modifications and variations of the present invention are possible in light of the above teachings and, therefore, are within the scope of the appended claims.

EXAMPLE 1

CNGH0010 Sequence Data

The CNGH0010 genomic nucleotide sequence (SEQ ID NO:1) spans 16356 bp. Based on modeling with several gene prediction algorithms, such as GeneScan, Fgenesh (genome.ucsc.edu/) and the Acembly program (www.acedb.org/Cornell/acembly/), CNGH0010 is predicted to comprise 25 exons (FIG. 1, Table 1). Exons 1, 7 and 18 each contain a start codon and are downstream from promoter, enhancer, and other regulatory motifs; these exons may be utilized as initiation exons. Exons 15 and 23 contain a stop codon and can be utilized as termination exons. Five categories of alternatively spliced transcripts have been identified and are exemplified in CNGH0010.1, CNGH0010.2, CNGH0010.3, CNGH0010.4, and CNGH0010.5 (SEQ ID NOS: 2, 4, 6, 8, and 10, respectively, Table 2).

TABLE 1

CNGH0010 exon composition and description

| Exon # | start position | stop position | # of bp | frame | Note |
|---|---|---|---|---|---|
| 1 | 101 | 526 | 426 | In | 1st ini. Exon; Constant for 10.1 and 10.2 |
| 2 | 786 | 986 | 201 | In | Constant for 10.1 and 10.2 |
| 3 | 1099 | 1155 | 57 | In | Constant for 10.1 and 10.2 |
| 4 | 1763 | 1813 | 51 | In | Constant for 10.1 and 10.2 |
| 5 | 1983 | 2165 | 183 | In | Constant for 10.1 and 10.2 |
| 5a | 1983 | 2076 | 85 | out | left exon |
| 5b | 2117 | 2165 | 91 | out | right exon |
| 6 | 2936 | 2980 | 45 | In | rare exon |
| 7 | 3149 | 3205 | 57 | In | 2nd initiation exon; Constant for 10.3 and 10.4 |
| 7a | 3168 | 3197 | 30 | out | |
| 8 | 3324 | 3392 | 69 | In | Constant for 10.3 and 10.4 |
| 8a | 3189 | 3392 | 204 | out | overlap with exon 8 but longer |
| 9 | 3615 | 3665 | 51 | In | Alternatively spliced |
| 10 | 5336 | 5371 | 36 | In | Alternatively spliced |
| 11 | 6065 | 6118 | 54 | In | Alternatively spliced |
| 12 | 7391 | 7450 | 60 | In | Alternatively spliced |
| 13 | 7590 | 7637 | 48 | In | Constant for 10.1, 10.2, 10.3, and 10.4 |
| 14 | 7811 | 7858 | 48 | In | Constant for 10.1, 10.2, 10.3, and 10.4 |
| 15 | 10129 | 10155 | 27 | In | 1st term. Exon |
| 16 | 10690 | 10746 | 57 | In | Constant for 10.1, 10.2, 10.3, and 10.4 |
| 17 | 11393 | 11440 | 48 | In | Constant for 10.1, 10.2, 10.3, and 10.4 |
| 18 | 11679 | 11753 | 75 | In | 3rd initiation exon, constant for 10.5 |
| 19 | 12996 | 13043 | 48 | In | Constant for 10.1, 10.3 and 10.5 |
| 20 | 13157 | 13198 | 42 | In | Alternatively spliced |
| 21 | 13547 | 13618 | 72 | In | Constant for 10.1, 10.3 and 10.5 |
| 22 | 14679 | 14702 | 24 | In | Constant for 10.1, 10.3 and 10.5 |
| 23 | 14813 | 14860 | 48 | In | Constant for 10.1, 10.3 and 10.5 |
| 24 | 15895 | 15929 | 35 | NA | 3'UTR-1 |
| 25 | 16038 | 16356 | 319 | NA | 3'UTR-2 |

Table 2 shows the various CNGH0010 transcripts and exons contained within each transcript. The exons shown in bold are constant in each transcript, while the other exons listed for each transcript are alternatively spliced and, optionally, part of various transcripts. As shown in Table 2, the nucleotide and amino acid sequences for each transcript vary depending on the exact combination of exons present.

TABLE 2

CNGH0010 transcripts description

| Transcript | Exons | Nucleotide Length (bp) | Peptide Length (aa) |
|---|---|---|---|
| CNGH0010.1 | 1, 2, 3, 4, 5, 6, 8, 9, 10, 11, 12, 13, 14, 16, 17, 19, 20, 21, 22, 23, 24, 25 | 1809/2132 | 459/555 |
| CNGH0010.2 | 1, 2, 3, 4, 5, 8, 9, 10, 11, 12, 13, 14, 15 | 1533/1734 | 373/440 |
| CNGH0010.3 | 7, 8, 9, 10, 11, 12, 13, 14, 16, 17, 19, 20, 21, 22, 23, 24, 25 | 881/1159 | 172/253 |
| CNGH0010.4 | 7, 8, 9, 10, 11, 12, 13, 14, 15 | 445/646 | 82/149 |
| CNGH0010.5 | 18, 19, 21, 22, 23, 25 | 600 | 88 |

CNGH0010.1 is any transcript that starts with exon 1 and ends at exon 25, excluding exons 7, 15, and 18. It may have as few as 15 exons (i.e., exons 1-5, 8, 13, 14, 16, 17, 19, 21-23, and 25) or as many as 22 exons (i.e., exons 1-6, 8-14, 16, 17, and 19-25). Exons 6, 9-12, 20, and 24 can be differentially spliced, either individually or in any combination. Therefore, CNGH0010.1 transcripts range from 1809 to 2132 bp. They encode peptides ranging from 459 to 555 amino acids, depending on the exon composition.

CNGH0010.2 is any transcript that starts with exon 1 and ends at exon 15, excluding exons 6 and 7. It may have as few as 9 exons (i.e., exons 1-5, 8, and 13-15) or as many as 13 exons (i.e., exons 1-5 and 8-15). Exons 9-12 can be differentially spliced, either individually or in any combination. Therefore, CNGH0010.2 transcripts range from 1533 to 1734 bp, encoding peptides ranging from 373 to 440 amino acids, depending on the exon composition.

CNGH0010.3 is any transcript that starts with exon 7 and ends at exon 25, excluding exons 15 and 18. It may have as few as 11 exons (i.e., exons 7, 8, 13, 14, 16, 17, 19, 21-23, and 25) or as many as 17 exons (i.e., exons 7-14, 16, 17, and 19-25). Exons 9-12, 20, and 24 can be differentially spliced, either individually or in any combination. Therefore, CNGH0010.3 transcripts range from 881 to 1159 bp, encoding peptides ranging from 172 to 253 amino acids, depending on the exon composition.

CNGH0010.4 is any transcript that starts with exon 7 and ends at exon 15. It may have as few as 5 exons (i.e., exons 7, 8, and 13-15) or as many as 9 exons (i.e., exons 7-15). Exons 9-12 can be differentially spliced, either individually or in any combination. Therefore, CNGH0010.4 transcripts range from 445 to 646 bp, encoding peptides ranging from 82 to 149 amino acids, depending on the exon composition.

CNGH0010.5 is any transcript that starts with exon 18 and ends at exon 25, excluding exons 20 and 24. It has 6 exons, i.e., exons 18, 19, 21-23, and 25. The CNGH0010.5 transcript contains 600 bp encoding a peptide of 88 amino acids.

In addition to these 5 categories, a transcript that contains exons 5a, 5b, 7a, or 8a will have out-of-frame splicing at the site where these exons begin in the corresponding transcripts; this may result in truncated proteins at the site of the exon or downstream of the exon. Often, the truncated proteins use an alternative initiation ATG codon in exon 13, at nucleotide position 7611.

The CNGH0010.1 amino acid sequence of SEQ ID NO:3 has 94% identity over 449 residues to GenBank Accession No. AY358412 (Pat. Publ. No. WO/200061623); the CNGH0010.2 amino acid sequence of SEQ ID NO:5 has 100% identity over 440 residues to Dgen No. AAF54238 (Pat. Publ. No. WO/200078961); the CNGH0010.3 amino acid sequence of SEQ ID NO:7 has 99% identity over 127 residues to DgenNo. AAH23810 (Pat. Publ. No. WO/200132888); the CNGH0010.4 amino acid sequence of SEQ ID NO:9 has 98% identity over 93 residues to Dgen No. ADE28278 (Pat. Publ. No. WO/2003046152); and the CNGH0010.5 amino acid sequence of SEQ ID NO:11 has 85% identity over 102 residues to DgenNo. AAF97894 (Pat. Publ. No WO/200121658).

EXAMPLE 2

CNGH0010 Transcripts

5' and 3'-RACE (Rapid Analysis of cDNA Ends) was performed on total RNA from A431 cells and normal adult human male skin tissue according to the manufacturer's protocol (Catalog number L1502-01, Invitrogen, Corp., Carlsbad, Calif.). Briefly, 5 μg of total RNA was dephosphorylated with calf intestine alkaline phosphatase to remove phosphogroups from non-mRNA or truncated mRNA. The RNA was then treated with Tobacco Acid Pyrophosphatase to remove the 5' cap structure from mature mRNA. An RNA oligonucleotide of known sequence was then ligated to the 5' ends of mature mRNA, and then used as a template for reverse transcription with Superscript RT enzyme, primed with an oligo dT primer that also contained a unique known sequence. RT was carried out at 42° C. for 1.5 hours. The resulting cDNAs contained common sequences at their 5' ends and 3' ends, and could be used with nested oligonucleotides specific for the CNGH0010 gene (SEQ ID NOS:12-21, Table 3) to amplify all or part of the cDNA through PCR.

TABLE 3

RACE primers

| SEQ ID NO: | Olligo name | Sequence | and exon |
|---|---|---|---|
| 12 | CNGH0010EX1F | GGC TGG GCA GAG ATG AAG TTC CAG | EXON1 |
| 13 | CNGH0010EX1FNEST | TCT GCC TGG GCA GTG GGG AG | EXON1 |
| 14 | CNGH0010EX7F | ATG CTC GGA ATA ACT TCC TGC AGC G | EXON7 |
| 15 | CNGH0010EX7FNEST | GCA GCG ACC AAC AGG CTA AAG | EXON7 |
| 16 | CNGH0010EX18F | ATG AAG CCG GCC ACT GCC TCTG | EXON18 |

TABLE 3-continued

RACE primers

| SEQ ID NO: | Olligo name | Sequence and exon | |
|---|---|---|---|
| 17 | CNGH0010EX18FNEST | CTC TGC TCC TGC TCC TGC TG | EXON18 |
| 18 | CNGH0010UTR2R | GGG CCA GGG CTG GCA CAG GC | UTR2 |
| 19 | CNGH0010UTR2NEST | CGG GGC CTC GGT GGT GGT TGC | UTR2 |
| 20 | CNGH0010EX15R | TCT GGT GGC TCC TTG TCT GGA GGT C | EXON15 |
| 21 | CNGH0010EX15RNEST | GTC ACG GGA TGC GAG AGC TTC TCT GGT C | EXON15 |

Figure 2:
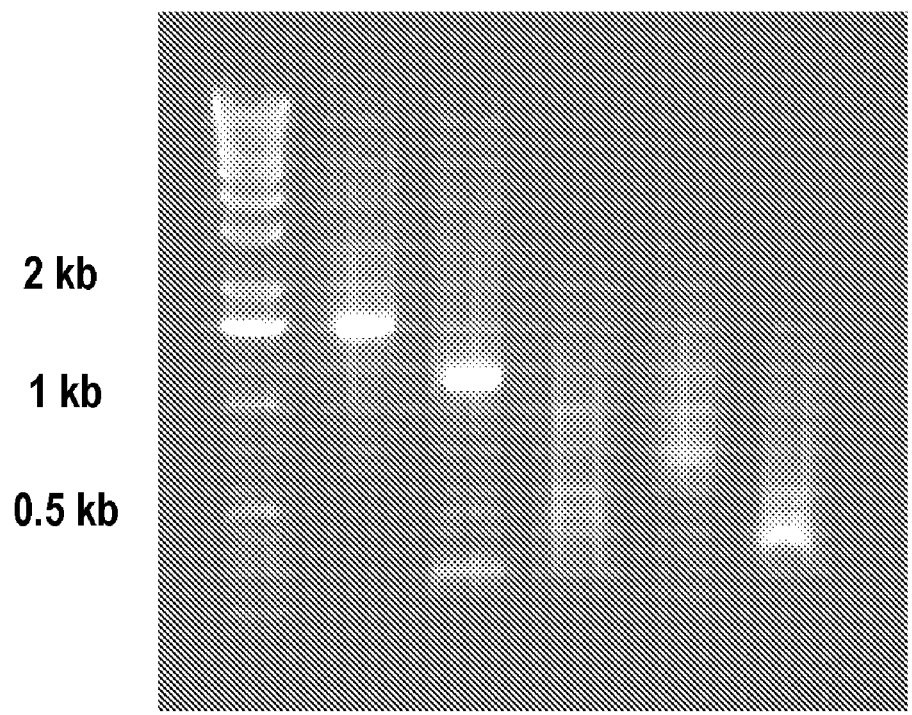
FIG. 2 shows relative transcript levels as determined by RT-PCR using RNA from A431 cells.

SEQ ID NOS:12 or 13 in exon 1 with SEQ ID NOS:18 or 19 in exon 25 (3'UTR-2) were used to amplify CNGH0010.1 transcripts. SEQ ID NOS:12 or 13 with SEQ ID NOS:20 or 21 in exon 15 were used to amplify CNGH0010.2 transcripts. SEQ ID NOS:14 or 15 in exon 7 with SEQ ID NOS:18 or 19 in exon 25 were used to amplify CNGH0010.3 trancripts. SEQ ID NOS:14 or 15 in exon 7 with SEQ ID NOS:20 or 21 in exon 15 were used to amplify CNGH0010.4 transcripts. SEQ ID NOS:16 or 17 in exon 18 with SEQ ID NOS:18 or 19 in exon 25 were used to amplify CNGH0010.5 transcripts. RT-PCR data, as shown in FIG. 2, demonstrated that the transcripts of CNGH0010.1 (SEQ ID NO:2), 10.2 (SEQ ID NO:4) are at the highest level, followed by 10.5 (SEQ ID NO:10) at a lower level, 10.4 (SEQ ID NO:8) at a significantly lower level, and 10.3 (SEQ ID NO:6) at the lowest level of all of the transcripts.

As shown in Table 4 below, five sets of forward/reverse primers and probes were designed to identify the five dominant splice variants by real time PCR application. For each splice variant, the forward and reverse primers and Taqman probe are shown. Total RNA extracted from A431 and HCT116 cells treated with various concentrations of TNFα, LPS, and IL-12 was reversed transcribed into a cDNA template, which was then amplified by real time PCR using these 5 sets of primers/probes. CNGH0010.2 and CNGH0010.5 were upregulated by various concentrations of TNFα, LPS, and IL-12.

TABLE 4

Forward/reverse primers and probes of real time PCR for splice variants

| Splice variant | Forward primer | Reverse primer | Taqman Probe |
|---|---|---|---|
| CNGH0010.1 | SEQ ID NO:25: GAGGTGACAGCGG CAGTGAGT | SEQ ID NO:26: TTAAAATTCTTCC AGAAAGTGTCAAA GTTA | SEQ ID NO:27: ATTCAGAACTCTG AGACGTC |
| CNGH0010.2 | SEQ ID NO:28: TGTTGGTGGAGTC AATACTGTGAACT | SEQ ID NO:29: CGGGATGCGAGAG CTTCTC | SEQ ID NO:30: CACTTTCTGGAAG AATTTTAAATC |
| CNGH0010.3 | SEQ ID NO:31: GGAGCGGCGGAGG AAAT | SEQ ID NO:32: TGATGAAACCCAG CTTGGATT | SEQ ID NO:33: AAACCCGGGAACT CTGAGAC |
| CNGH0010.4 | SEQ ID NO:34: GGCGGAGGAAATG GACATAAA | SEQ ID NO:35: GAGCTTCTCTGGT CCTTGTTTATG | SEQ ID NO:36: AATCTGGGATTCA GAACTC |
| CNGH0010.5 | SEQ ID NO:37: GGGTGCGGACGCG TCAT | SEQ ID NO:38: GTCTTGACTGAGT ACTTCCCACCATA | SEQ ID NO:39: ACGATCAGAACTA CAATTACAAC G |

EXAMPLE 3

Predicted CNGH0010 Protein Domains

Figure 3:
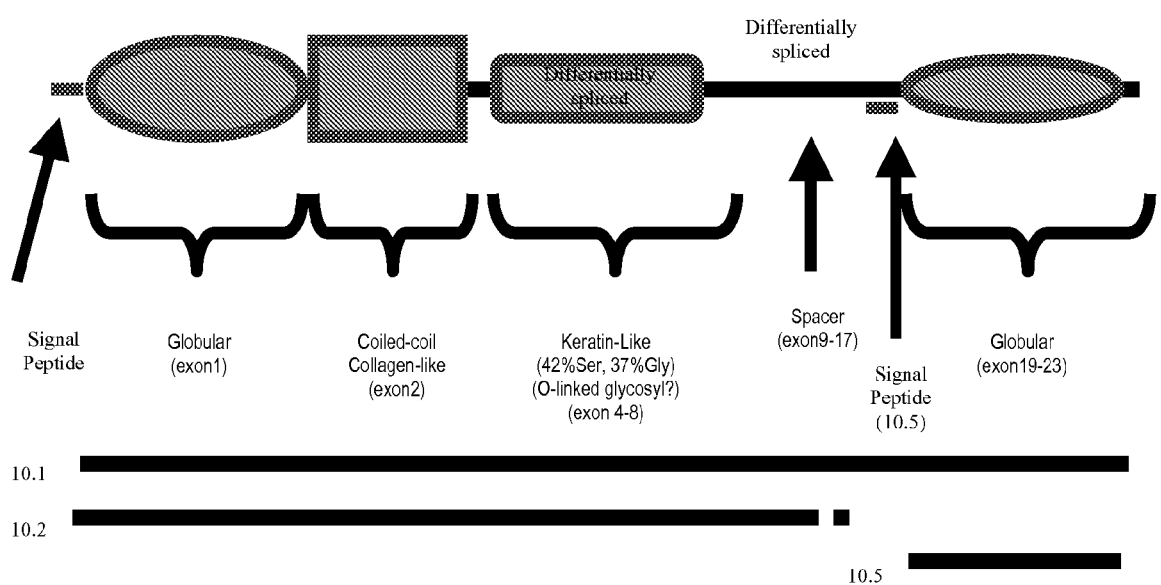
FIG. 3 shows predicted protein domains based on expression data and analysis of the amino acids coded by CNGH0010 transcripts.

The CNGH0010.1 and CNGH0010.2 polypeptides may contain up to 555 and 440 amino acids, respectively (SEQ ID NOS:3 and 5, respectively). The first 21 amino acids encode a signal peptide, followed by five major domains (FIG. 3). The first domain, which includes the signal peptide, is encoded by exon 1, and has no significant homology to any known proteins or protein domains. This domain is predicted to form at least 6 subdomains of alpha-helical secondary structure based on the NNPredict program. The second domain, encoded by exon 2, possesses 19 Glycine-X-Y repeats that are known to form coiled-coiled structures, as seen in collagen and collagen-like molecules. This domain is then followed by a differentially spliced serine-glycine rich domain (up to 42% serine, 37% glycine), encoded by exons 4-8. The differential splicing appears to alter the size and amount of serine-glycine residues.

A differentially spliced spacer domain is encoded by exons 9-17. The exons encoding this region are very small, ranging in size from 36 to 60 nucleotides. This region is predicted to have minimal if any secondary structure using the NNPredict program. The differential splicing that occurs in this region appears to regulate the distance between the serine-glycine rich domain, and the C-terminal domain. The CNGH0010.1 (SEQ ID NO:3) terminates in another domain encoded by exons 19-23 that has no homology to any known proteins. This domain is predicted to have at least 2 regions of predicted alpha-helix. The CNGH0010.2 (SEQ ID NO:5) polypeptide possesses all of the domains included in the 10.1 (SEQ ID NO:3) polypeptide, except for the C-terminal domain encoded by exons 19-23. The CNGH0010.3 (SEQ ID NO:7) polypeptide may contain up to 253 amino acids and contains part of the differentially spliced Serine-Glycine rich domain, the differentially spliced spacer domain, and the C-terminal domain. The CNGH0010.4 (SEQ ID NO:9) polypeptide may contain up to 149 and includes part of the differentially spliced Serine-Glycine rich domain and the differentially spliced spacer domain. Finally, the CNGH0010.5 (SEQ ID NO:11) polypeptide has 88 amino acids and contains essentially the C-terminal domain, preceeded by a signal peptide encoded by exon 18.

Figure 4:
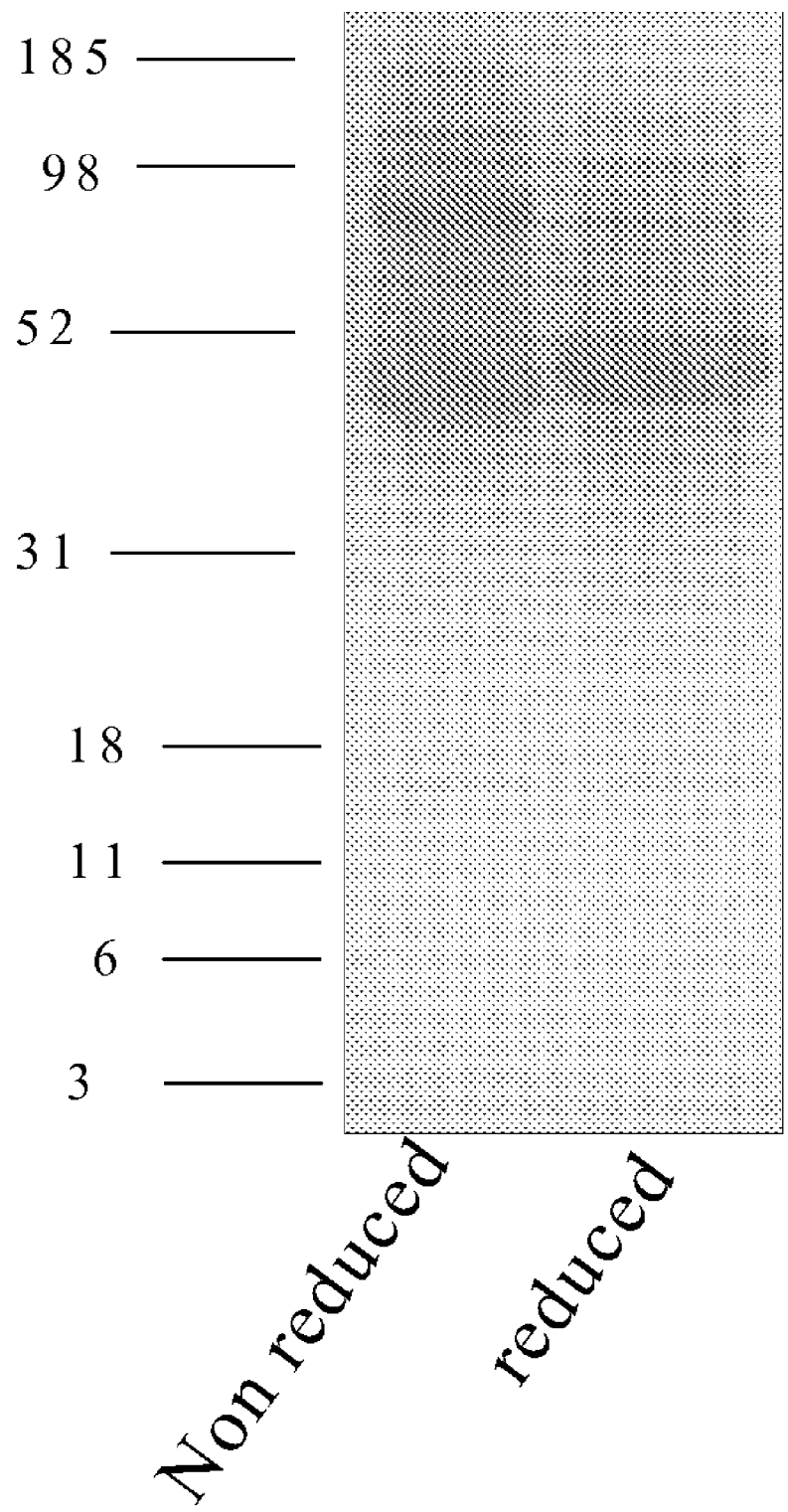
FIG. 4 shows SDS-PAGE analysis of CNGH0010.2 expressed in HEK293 cells in reduced and non-reduced samples.

The domains of CNGH0010 allow for the assembly of a homo (all CNGH0010.1 (SEQ ID NO:3)) or all CNGH0010.2 (SEQ ID NO:5)) or hetero (mixture of CNGH0010.1 (SEQ ID NO:3) and CNGH0010.2 (SEQ ID NO:5))-trimers, such as collagens or adiponectin, through the collagen-like coiled-coil region. The presence of proline residues at some of the X-Y positions of the Gly-X-Y repeat is thought to stabilize these trimers, by unknown mechanisms and thus provides further evidence that the molecule might form collagen-like structures. Preliminary biochemical characterization of recombinantly expressed CNGH0010.2 (SEQ ID NO:5) polypeptide indicates that this molecule does indeed form oligomers. SDS-PAGE analysis (as shown in FIG. 4) indicates that molecules with molecular weights of 2, 3 and 4 times that of the single chain exist in both non-reduced and reduced samples, indicating that some of the oligomers are covalently bound. This result has been confirmed by SELDI mass spectrometry and gel filtration HPLC. As seen in collagen molecules, covalent cross-linking between trimer chains can be seen by post-translational modification of Lysine residues present in the polypeptide. This modification results in covalent dimer, trimer, and multimers (fibrils) of the polypeptide. The CNGH0010.5 (SEQ ID NO:11) molecules are essentially the C-terminal domain and may have unique functional activity.

EXAMPLE 4

Secretion of CNGH0010 Polypeptides

The CNGH0010.1 and 10.2 polypeptides contain the same predicted signal sequence (amino acids 1-21 in SEQ ID NOS:3 and 5). The predicted CNGH0010.5 polypeptide sequence has a different signal sequence (amino acids 1-24 in SEQ ID NO:11). In vitro transient expression of a His tagged CNGH0010.2 fusion protein, as well as a CNGH0010.5 mimetibody (the details of which are described in Example 6), confirmed that the signal sequences indeed target these polypeptides for extracellular secretion. Therefore, CNGH0010.1 (SEQ ID NO:3), 10.2 (SEQ ID NO:5), and 10.5 (SEQ ID NO:11) polypeptides probably are secreted into the extracellular space where they might exert their effects. CNGH0010.3 and CNGH0010.4 (SEQ ID NOS:7 and 9) do not contain a signal sequence.

EXAMPLE 5

Relative CNGH0010 Transcript Levels in Selected Disease Tissues

CNGH0010 primers and probes, Primers: CNGH00010ss1—GGC GGA GGA AAT GGA CAT AA (SEQ ID NO:23), CNGH00010as1—GCT TGG ATT TAA AAT TCT TCC AGA AA (SEQ ID NO:24), TaqMan MGB Probe: CNGH00010p1—6FAM—GCT TTT CAC ACC CGG GT—MGBNFQ (SEQ ID NO:22) were designed using Primer Express software and synthesized by Applied Biosystem (Foster City, Calif.). Total RNAs were isolated from different tissues, reverse transcribed and amplified by PCR using these primers/probes. Relative transcript levels of CNGH0010 are shown below in Table 5.

TABLE 5

Distribution of CNGH0010 in different human disease tissues

| Tissues | Disease | Fold change* |
|---|---|---|
| Brain | Normal | 1.00 |
| Lung | Emphysema | 4.58 |
| Lung | respiratory infection | 0.19 |
| Tonsil | Tonsillitis | 1.63 |
| Thyroid | grave's disease | 8.35 |
| Thyroid | lymphocytic thyroidities | 3.90 |
| Pancreas | Diabetes | 9.45 |
| Pancreas | Pancreatitis | 0.86 |
| Liver | Cirrhosis | 0.45 |
| Colon | Colitis | 0.24 |
| Colon | UC | 0.22 |
| Synovium | osteoarthritis/DJD | 0.14 |
| Catilage | osteoarthritis/DJD | 1.32 |
| Ovary | endometriosis | 2.18 |
| Bladder | cystitis | 0.19 |
| Lymphoma | hodgkin | 0.06 |
| Sarcoma |  | 0.21 |

*The level of CNGH0010 in each tissue is compared to the level in normal brain tissue that acts as the control (1.00 Fold Change).

When compared with calibration tissue, normal human brain RNA, an increase in CNGH0010 mRNA level was detected in emphysematous lung tissue, thyroid tissue from Grave's disease patient or inflammatory thyroiditis, inflamed tonsil, ovary from endometriosis patient, diabetic pancreas and osteoarthritic cartilage.

EXAMPLE 6

Protein Expression

Expression of the CNGH0010.2 (SEQ ID NO:5) protein was performed by cloning most of a CNGH0010.2 transcript containing exons 1-5, 8, 9, 12 and part of 13 inframe of a hexa-His tag in an expression vector driven by a CMV promoter. This construct was transfected into HEK293 cells and purified with the His tag. The N-terminal sequence of the expressed and purified material confirmed the identity of the purified protein and demonstrated signal peptide cleavage. SDS-PAGE analysis of the expressed and purified protein indicated that the molecule forms oligomers (FIG. 4), which was confirmed by non-reducing MS-SELDI (surface enhanced laser desorption/ionization) and gel filtration HPLC. This data indicates that the CNGH0010.2 and CNGH0010.1 transcripts, since they contain the same signal sequence encoded by exon 1, have the ability to be secreted extracellularly. In addition, the SDS-PAGE, SELDI-MS, and gel filtration HPLC indicate that this molecule has the ability to form oligomers.

CNGH0010.5 (SEQ ID NO:11) could not be expressed alone in HEK293 cells; however, it was engineered as a mimetibody. Most of the CNGH0010.5 coding region containing amino acids 1 to 86 were engineered into an expression plasmid that contained the human IgH J2 segment fused to the human IgG1 hinge, $CH_2$ and $CH_3$. The plasmid contained a CMV promoter for transcription of recombinant genes, and utilized the CNGH0010.5 endogenous signal sequence encoding amino acids 1-24. This construct was transiently transfected into HEK293 cells, and the resulting secreted molecules purified by protein A affinity beads. SDS-PAGE analysis confirmed that a protein of predicted molecular weight containing the CNGH0010.5 mature amino acid sequence, followed by the J2, hinge, $CH_2$ and $CH_3$ of the human IgG1 had been expressed.

The expression levels of the CNGH0010.2 (SEQ ID NO:5) and CNGH0010.5 (SEQ ID NO:11) proteins in A431 and HCT116 cells were measured in response to stimulation by TNF-α and LPS. Stimulation by TNF-α and LPS caused an increase in CNGH0010.2 (SEQ ID NO:5) and CNGH0010.5 (SEQ ID NO:11) expression. Similarly, expression of CNGH0010.2 (SEQ ID NO:5) and CNGH0010.5 (SEQ ID NO:11) was increased in the presence of IL-12. Additionally, IL-6, IL-8, and GMCSF levels were increased by TNF-α treatment in A431 cells and they were reduced in the presence of a chimeric, anti-TNF-α antibody. IL-6 is an important inflammatory cytokine, the increase of this cytokine accompanied by the increase of CNGH0010.2 and 10.5 with TNF-α treatment indicates a possible mechanism of CNGH0010 and inflammatory Reponses. IL-8 is a chemokine that plays a critical role in inflammation. It recruits lymphocytes and leukocytes to the inflammatory site and stimulates other cytokine production. GMCSF is a stimulator for macrophage/monocytes as well as other lymphocytes, which also play roles in the inflammatory responses. This evidence suggests that CNGH0010 may play a role in the inflammatory regulation, therefore it could be a good target for therapeutic development.

EXAMPLE 7

Protein Analysis cDNAs for CNGH0010.1, 10.2, a truncated 10.2 (exons 1-5, 8, 9, 12, and 13) (SEQ ID NO:40), and 10.5 were cloned into commercial vector pcDNA3.1 mychis using novel restriction sites present in the vector and cDNA. These expression plasmids were sequenced, and then transfected into HEK293H cells using Lipofectamine 2000. Using a carboxyl terminal 6× Histidine tag, recombinantly expressed protein was purified on a Talon resin.

Figure 5:
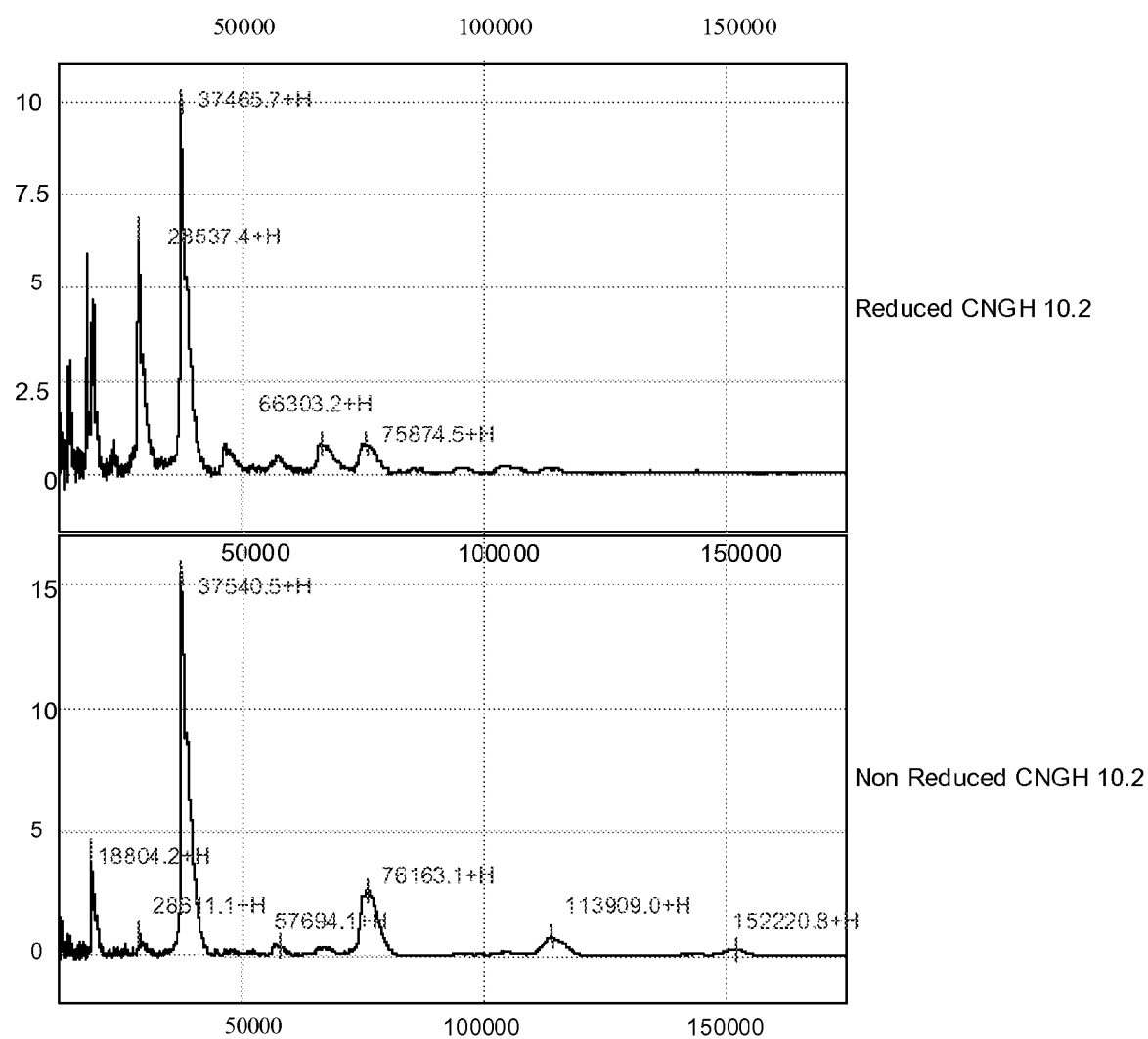
FIG. 5 shows the mass spectrum analysis of CNGH0010 (exons 1-13).
Figure 6:
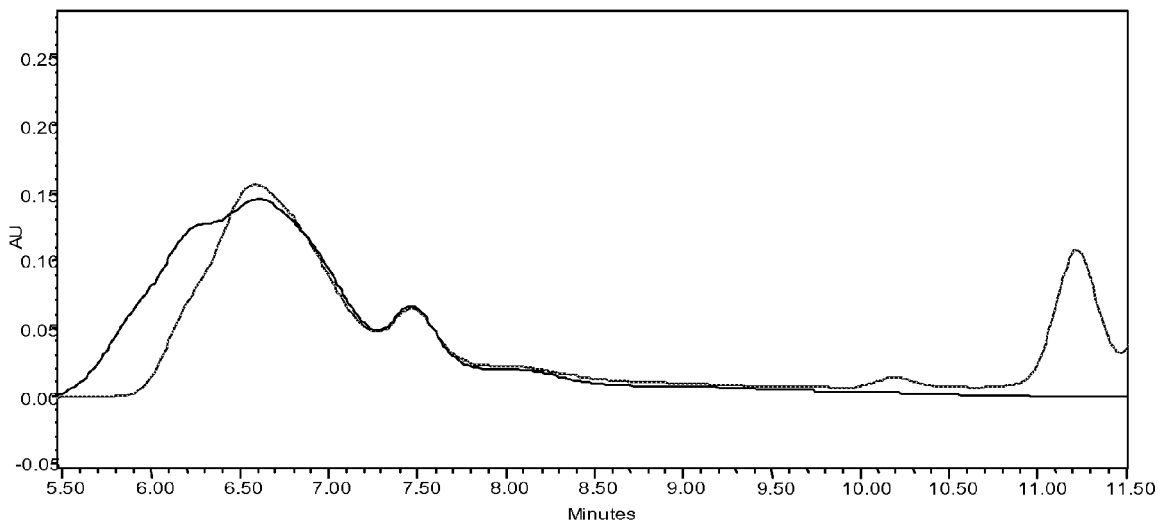
FIG. 6 shows the SEC-HPLC analysis of CNGH0010 (exons 1-13).

Recombinantly expressed proteins were analyzed by SDS-PAGE, anti-myc western blot, MALDI-MS, and SEC HPLC. In addition, O-linked glycosylation was analyzed by first treating the proteins with O-glycosidase with and without sialidase. The released O-glycans were labeled with anthranilic acid and analyzed by HPLC. The truncated CNGH0010.2 protein containing exons 1-5, 8, 9, 12, and 13 (SEQ ID NO:41) is predicted to be 37.5 kDa. However, SDS-PAGE analysis clearly shows this molecule running at an apparent molecular weight of 45 kDa. In addition, it appears as if the molecule has a propensity to multimerize, as non-reduced analysis by SDS-PAGE, SELDI-MS (FIG. 5), and SEC-HPLC (FIG. 6), all indicate that dimeric and trimeric forms of the truncated CNGH0010.2 molecule exist in solution.

Figure 7:
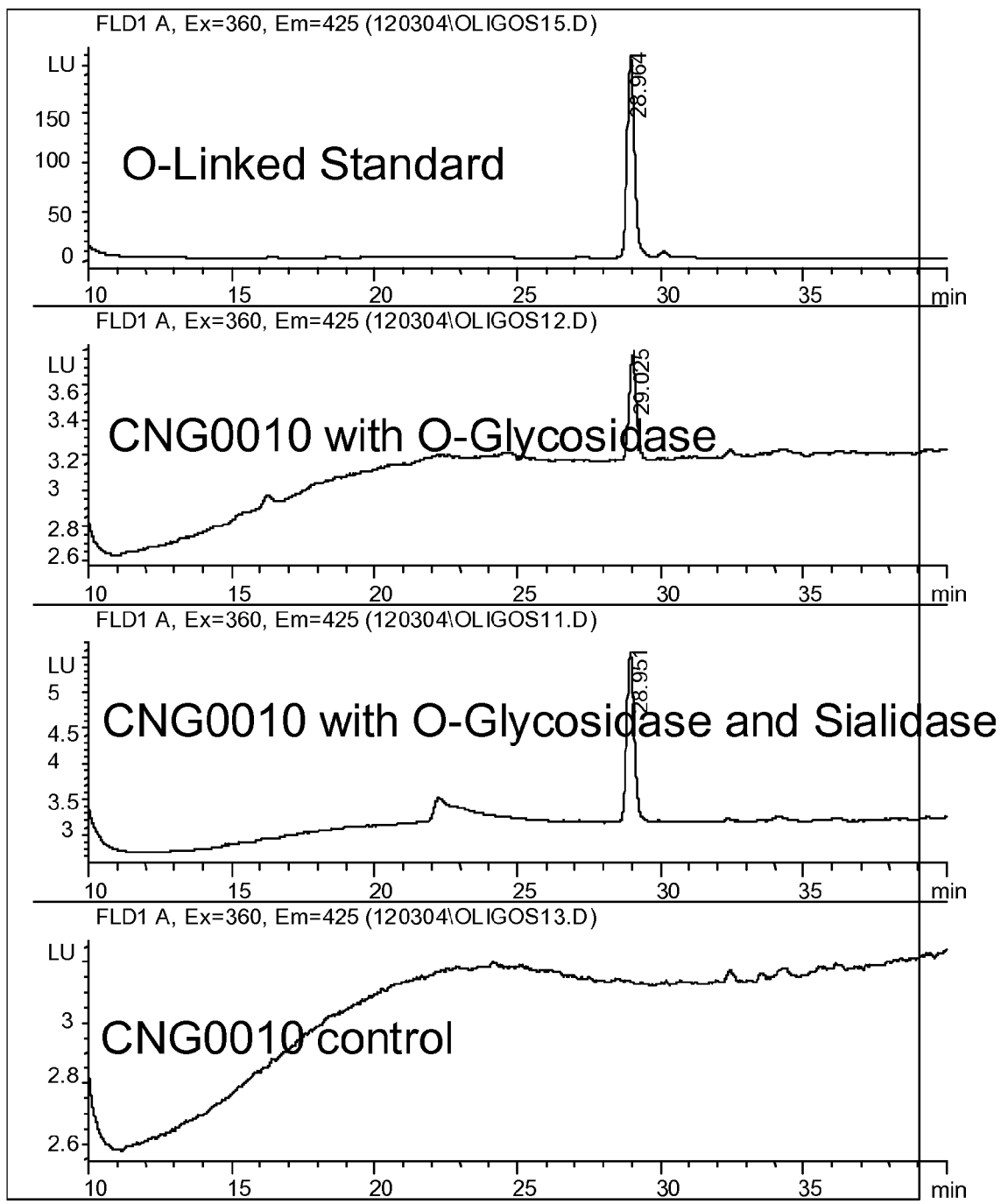
FIG. 7 shows the glycosylation analysis of CNGH0010 (exons 1-13).

The apparent discrepancy between the predicted MW and the observed by SDS-PAGE, might be explained by the presence of O-linked oligosaccharides covalently attached to the molecule. Glycosylation analysis of this protein clearly indicates the presence of such moieties (FIG. 7). The function of such groups on molecules is not completely understood. It has been speculated that they may aid in solubility, or delineate a region that is resistant to protease cleavage.

SDS-PAGE analysis of recombinantly expressed and tagged CNGH0010.1, CNGH0010.2, and CNGH0010.5 similarly showed discrepancies between predicted and apparent molecular weight (data not shown). Interestingly, all four proteins have stretches of serine and/or threonine residues that could serve as O-linked glycosylation sites that might be modified. This would account for the differences in the predicted and actual molecular weight migration on SDS-PAGE. The CNGH0010.1 and CNGH0010.2 variants possess identical stretches to those in the truncated CNGH0010.2 (SEQ ID NO:41) that has been confirmed to contain such glycosylation sites, and therefore, likely do as well.

EXAMPLE 8

Antibody Generation

Rabbit Anti-CNGH0010 Polyclonal Antibody Generation

Recombinantly expressed CNGH0010 protein (exons 1-5, 8, 9, 12, and 13) or chemically synthesized CNGH0010.5 was used to immunize New Zealand White rabbits on weeks 0, 2, 7, and 8. After 10 weeks, CNGH0010 specific antibodies were affinity purified using the recombinant CNGH0010 or chemically synthesized CNGH0010.5. These antibodies were tested for specificity by western blot analysis, with recombinant CNGH0010 isoforms as the target.

Mouse Anti-CNGH0010 Monoclonal Antibody Generation

Three Balb/c mice (Charles River Laboratories) were immunized intraperitoneally (IP) with 1 nanomole of prostaglandin E2 (PGE2) (Sigma) on day 1, then 3 hours later, received a second IP injection with 50 μg of human recombinant CNGH0010.2 truncated protein (SEQ ID NO:41) emulsified in Titermax adjuvant (Sigma). On days 2 and 3, the mice received additional IP injections of PGE2 and were then subsequently boosted with 50 μg truncated CNGH0010.2 in Titermax on days 21, 42, and 100. The mice were bled at various time points throughout the immunization schedule.

A cell bank of the non-secreting Balb/c mouse myeloma fusion partner, FO, was purchased from ATCC (#CRL-1646). One frozen vial of FO cells was received, thawed and resuspended in αMEM (modified) medium (JRH Biosciences) supplemented with 10% (v/v) FBS (Cell Culture Labs), 1 mM sodium pyruvate, 0.1 mM NEAA, 2 mM L-glutamine (all from JRH Biosciences). The cells were expanded, cryopreserved in 95% FBS and 5% DMSO (Sigma) and stored in a vapor phase liquid nitrogen freezer in CBS. The cell bank was sterile (internal Quality Control) and free of mycoplasma (tested by Bionique Laboratories). This cell line was thawed and maintained in log phase growth in the media described above for several days prior to fusion. The cells were washed in αMEM, counted, and viability determined (>85%) by Guava Viacount prior to fusion.

Six days prior to fusion, the mice were boosted IP with 50 μg of truncated CNGH0010.2 diluted in 200 μl PBS and three days prior to fusion, the mice were boosted with 100 μg anti-CD40 agonist Mab (R&D Systems). On fusion day, the mice were sacrificed by cervical dislocation and the spleens were removed aseptically and immersed in 10 mL of cold phosphate-buffered saline (PBS) containing 100 U/mL penicillin, 0.1 mg/mL streptomycin, and 0.25 μg/mL amphotericin B (PSA) (Sigma). The splenocytes were harvested by grinding through a fine mesh screen with a small pestle and rinsing with warm αMEM. The cells were washed and diluted to 2×10$^7$ cells/mL. The cells were then layered onto Lympholyte-M density separation medium (Accurate) and centrifuged at 1200×g for 20 minutes at RT. PBMC at the interface were removed and washed once more in warm αMEM. Fusions were carried out at a 1:1 ratio of FO murine myeloma cells to viable spleen cells according to the method of De St. Groth. Briefly, spleen and myeloma cells were mixed together, pelleted and washed twice in 50 mL of αMEM supplemented with 2 mM L-glutamine (JRH Biosciences) and 25 μg/mL gentamicin (Sigma). The pellet was resuspended with 1-2 mL of polyethylene glycol (PEG) solution (2 g PEG molecular weight 4000, 2 mL αMEM, 0.4 mL DMSO) at 37° C. over 1 minute. The cell/fusion mixture was then immersed in a 37° C. water bath for approximately 60 seconds with gentle agitation. The fusion reaction was stopped by adding 37° C. αMEM: 1 mL in the first minute, 15 mL in the next 3 minutes, and approximately 33 mL in the following minute. The fused cells were allowed to rest for 5 minutes at RT and then centrifuged at 150×g for 5 minutes. The cells were resuspended in HAT medium (αMEM (modified), supplemented with 20% FBS, 5% Origen, 1 mM sodium pyruvate, 0.1 mM NEAA, 2 mM L-glutamine, 25 µg/mL gentamicin (Sigma) and HAT (100 µM hypoxanthine, 0.4 µM aminopterin, and 16 µM thymidine—Sigma)) and then seeded in 96-well flat bottom polystyrene tissue culture plates (Coming #25860). The fusion plates were then placed in a humidified 37° C. incubator containing 7% $CO_2$ and left undisturbed for 7-10 days.

Solid phase EIA was used to screen mouse sera for titers and hybridoma supernatants for antibodies specific for human CNGH0010. Briefly, plates (Nunc-Maxisorp #446612) were coated overnight with human CNGH0010 at 2 µg/mL in PBS. After washing in 0.15 M saline containing 0.02%(w/v) Tween 20, the wells were blocked with 1% (w/v) bovine serum albumin (BSA) in PBS for 1 hr at 37° C. Mouse sera dilutions or undiluted hybridoma supernatants were incubated on coated plates for 1 hour at 37° C. Plates were washed and probed with HRP-labeled goat anti-murine IgG (Sigma) diluted 1:10,000 in 1% BSA/PBS for 30 minutes at 37° C. Plates were again washed then incubated for 15 minutes at RT with 100 µL/well of citrate-phosphate substrate solution (0.1 M citric acid and 0.2 M sodium phosphate, 0.01% $H_2O_2$, and 1 mg/mL OPD). Substrate development was stopped by addition of 4N sulfuric acid at 25 µL/well and the absorbance was measured at 490 nm via an automated plate spectrophotometer. Because the CNGH0010 protein generated in-house contains a His-tag, the reactive hybrids were cross-screened against His to determine specificity to CNGH0010. Plates were coated with hexa-his (Centocor) as described above and positive hybrid supernatants were incubated, probed and developed as described. All hybrid cell lines that demonstrated specificity to CNGH0010 were subcloned twice by limiting dilution at 1 cell/well in cloning plates. The homogeneous cell lines were cryopreserved in freezing medium (90% FBS, 10% DMSO) and stored in liquid nitrogen.

Binding characteristics for the antibodies were assessed using a solid phase CNGH0010 EIA. CNGH0010 coated plates were incubated with antibody supernatants with known IgG concentrations in two-fold serial dilutions from a starting concentration of 5 µg/mL for 30 minutes at 37° C. Plates were washed, probed and processed as described above.

EXAMPLE 9

Mouse Anti-CNGH0010 Affinity Analysis

Mouse anti-CNGH0010 monoclonal antibodies were individually captured on anti-murine Fc surfaces of a Biacore 3000 biosensor. CNGH0010.2 was injected in duplicate at increasing concentrations (7.4 to 600 nM). Affinities were calculated from the ratio of measured rate constants ($k_d/k_a$) and are shown in Table 6.

TABLE 6

Kinetic analysis data

| mAb | Capture (RU) | $k_a\ M^{-1}s^{-1}$ | $k_d\ s^{-1}$ | $K_D$ nM |
|---|---|---|---|---|
| 1291 | 300 | $6.24 \times 10^4 \pm 0.01$ | $5.1 \times 10^{-4} \pm 0.2$ | 8.1 |
| 1292 | 400 | $7.09 \times 10^4 \pm 0.02$ | $1.0 \times 10^{-5}$ | <0.14 |
| 1324 | 200 | $2.66 \times 10^4 \pm 0.01$ | $1.25 \times 10^{-3} \pm 0.04$ | 46.9 |
| 1329 | 290 | $8.21 \times 10^4 \pm 0.02$ | $9.5 \times 10^{-4} \pm 0.1$ | 11.6 |
| 1332 | 325 | $1.35 \times 10^5 \pm 0.04$ | $2.21 \times 10^{-3} \pm 0.02$ | 16.3 |
| 1333 | 200 | $1.41 \times 10^5 \pm 0.01$ | $4 \times 10^{-4}$ | 7.0 |
| 1339 | 200 | $5.00 \times 10^4 \pm 0.02$ | $7 \times 10^{-5} \pm 1$ | 1.4 |
| 1354 | 230 | $6.55 \times 10^4 \pm 0.02$ | $1.0 \times 10^{-5}$ | <0.15 |

EXAMPLE 10

CNGH0010 Expression Analysis in Tissues

Protocols for immunohistochemistry have been previously described (D'Andrea, et al, 1994; D'Andrea et al, 1998a). All incubations were performed at room temperature. After microwaving the slides in Target (Dako, Carpenturia, Calif.), the slides were placed in $dH_2O$, then 3% $H_2O_2$, rinsed in 10× Automation Buffer (Biomeda), treated with Avidin blocking, rinsed in buffer, & treated with Biotin blocking (15 minutes each, from Vector, catalog #SP-2001). Normal goat blocking serum (Vectastain, PK-6101) was then added for 10 minutes. Subsequently, the rabbit polyclonal primary antibody to 58 (or 60) (homemade antibodies) was applied to the slides for 30 minutes. Antibody diluent (Zymed, 00-3118) was substituted as the primary antibody for the negative control. After several PBS washes, a biotinylated secondary goat anti-rabbit antibody (Vector Labs, Burlingame, Calif.) was placed on the slides for 30 minutes. Subsequently, the slides were washed in PBS and then the avidin-biotin complex (ABC, Vector Labs, Burlingame, Calif.) was applied to the slides for 30 minutes. The presence of the primary antibodies was detected by adding DAB (3'-diaminobenzidine HCl; Biomeda, Foster City, Calif.) for 2 times 5 minutes each. Slides were briefly exposed to Mayer's hematoxylin (Sigma-Aldrich, MHS-32) for 1 minute, dehydrated and coverslipped.

Utilizing the rabbit polyclonal anti-CNGH0010 antibody to immunolocalize CNGH0010 isoforms in tissues and tumors, it is obvious that this gene product is expressed in a variety of both epithelial and non-epithelial tissues, including kidney, pancreas, lung, and skin. Specifically, CNGH0010 is expressed in the tubular epithelium of the kidney, the islet cells of the pancreas, the endothelial cells and macrophages of the lung, and the differentiated keratinocytes of the skin. Similarly, CNGH0010 is over-expressed in a number of tumors of both epithelial (carcinomas) and non-epithelial (sarcomas) origin, e.g., esophagus, gastro-intestinal stromal, liver, lung, osteosarcom, squamous cell (skin), thyroid, basal cell carcinoma, breast, and colon. It remains to be seen if the observed CNGH0010 over-expression in these tumors confers any growth advantage to them.

EXAMPLE 11

In Situ Hybridization

Figure 8A:
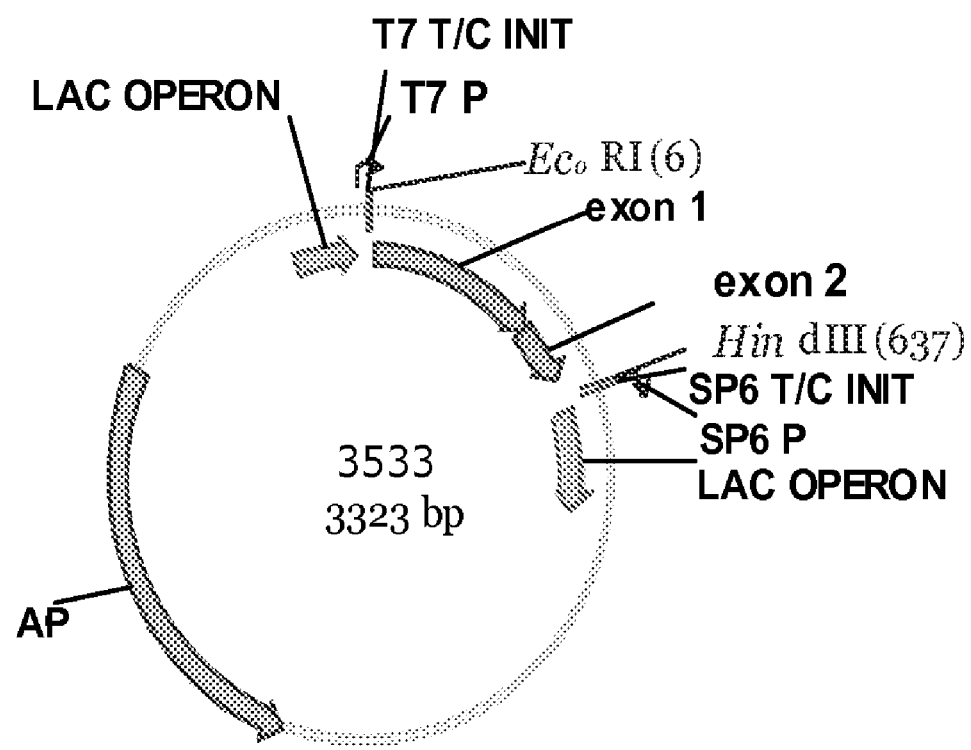
FIGS. 8A and 8B show the vector maps of the plasmids used to generate the CNGH0010 riboprobes.
Figure 8B:
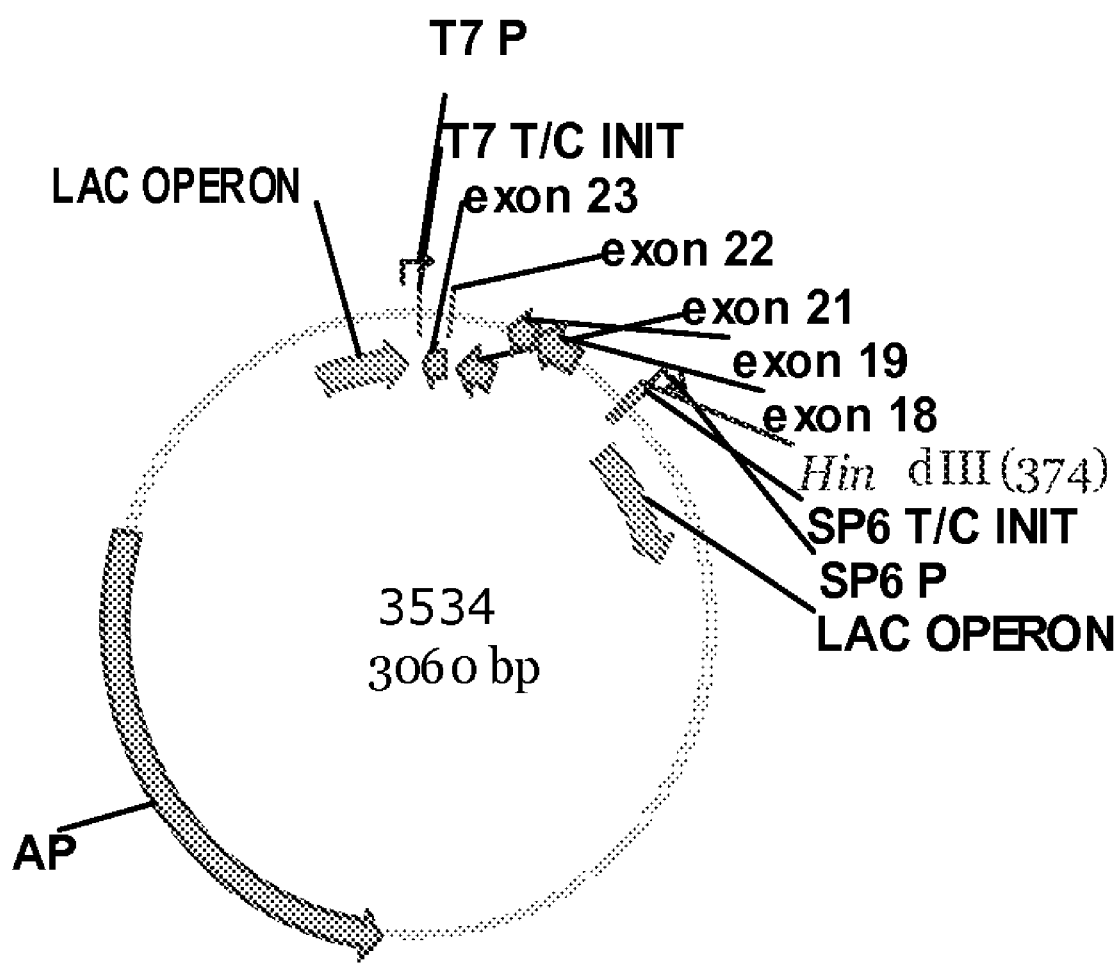

Fragments from the CNGH0010 cDNA were cloned into pGEM3Z for in vitro transcription using digoxigenin labeled ribonucleotides. Sense and anti-sense riboprobes were generated from these vectors after linearization with appropriate restriction enzymes. Plasmid p3533 was used to generate a CNGH0010.1 and 10.2 specific riboprobe using the SP6 promoter (FIG. 8A), and plasmid p3534 was used to generate a CNGH0010.1 and 10.5 specific riboprobe using the T7 promoter (FIG. 8B).

Human skin and human multi-tissue slides were routinely dewaxed and left to air dry for 30 minutes at room temperature. The tissues were digested with pepsin (Invitrogen, Carlsbad, Calif.) for 10 minutes at 37° C. Following this digestion, slides were washed briefly in dH$_2$O and placed into 3% H$_2$O$_2$ for 10 minutes at room temperature. The slides were thoroughly washed, dehydrated in alcohols 70%-95% for 1 minute each and then left again to air dry for 30 minutes at room temperature. Each probe was diluted to 15.0 ng/µl (Table 1) in probe diluent (Biomeda, Foster City, Calif.). Fifty microliters of probe cocktail was added on the tissue and a cover slip was placed atop the solution. The slides were denatured for 10 minutes at 95° C. and then placed into a humidity chamber (Slide Moat, Boekel Scientific, Feasterville, Pa.) for a 37° C. overnight incubation. After hybridization, the slides were then immediately placed into a low stringency wash (2×SSC for 5 minutes at 42° C.) and then into a high stringency wash (0.1×SSC) for 5 minutes at 42° C. The slides were washed in 1× auto buffer and then incubated with a horseradish peroxidase anti-dig antibody (anti-digoxigenin-POD, Fab fragments, Roche, Indianapolis, Ind.) for 1 hour at room temperature. The slides were washed and then exposed to 3-3' diaminobenzidine tetrahydrochloride chromogen for 2 times 5 minutes at room temperature. The slides were routinely stained with hematoxylin and then dehydrated, cleared in xylene, coverslipped in Permount (Fisher Scientific, Pittsburg, Pa.) then photographed under an Olympus BX51 light microscope. The positive control included a digoxigenin labeled mRNA riboprobe, β-actin. The negative controls included 1) the absence of the probe in the probe cocktail; 2) a sense strand of the targeted probed; and 3) pre-digestion of the tissues with a high concentration of RNase (32.5 mg/ml, Sigma, St. Louis, Mo.) for 2 hours at 37° C.

Figure 9A:
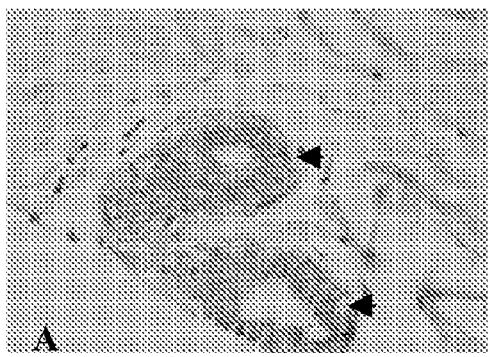
FIGS. 9A-F show the results of in situ hybridization of CNGH0010 in human tissue samples (breast FIG. 9A, small intestine FIG. 9B, skin FIG. 9C, prostate FIG. 9D, liver FIG. 9E, pancreas FIG. 9F).
Figure 9B:
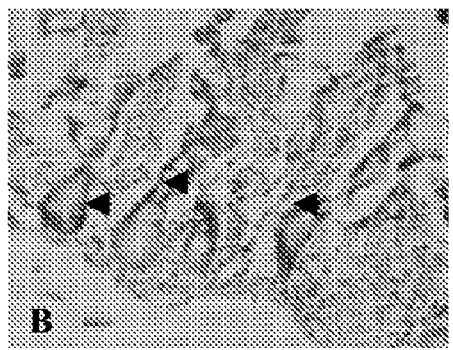
Figure 9C:
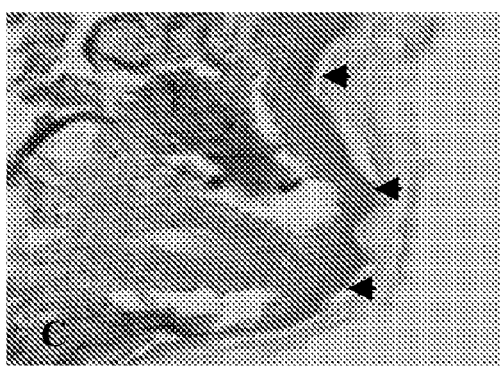
Figure 9D:
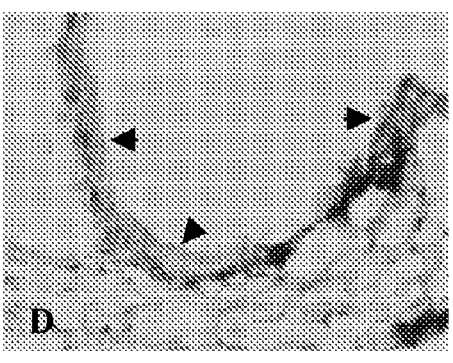
Figure 9E:
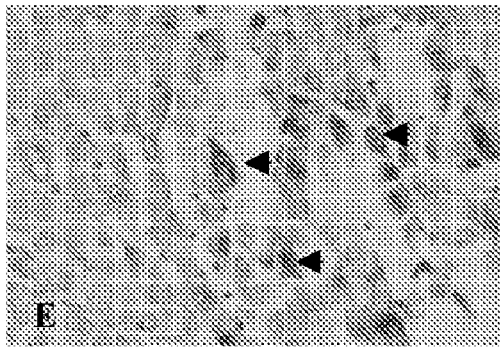
Figure 9F:
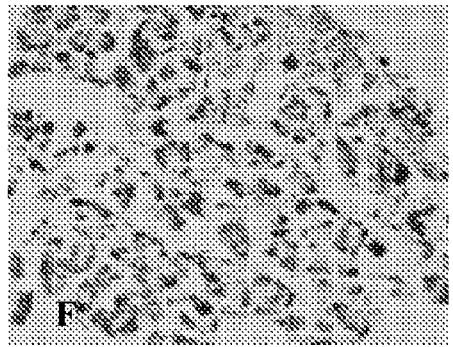

As shown in FIGS. 9A-F, in situ hybridization analysis of CNGH0010 shows expression in various tissues: breast (FIG. 9A), small intestine (FIG. 9B), skin (FIG. 9C), prostate (FIG. 9AD), liver (FIG. 9E), and pancreas (FIG. 9F). A digoxigenin labeled anti-sense riboprobe specific for the 5' and 3' ends of the CNGH0010 gene was used in the analysis. A sense probe was used to assess non-specific hybridization, and was negative on all samples (data not shown). The data obtained localizes the expression of the CNGH0010 gene to 6 epithelial tissue types that are often the sites of inflammation in various disease states. As a result, this data can allow the determination of which tissues to target for therapy with CNGH0010 agonists and/or antagonists, e.g., anti-CNGH0010 therapeutics. For example, CNGH0010 may be relevant to pathologic conditions like inflammatory disorders and cancer.

Although illustrated and described above with reference to certain specific embodiments, the present invention is nevertheless not intended to be limited to the details shown. Rather, the present invention is directed to the CNGH0010 polypeptides, polynucleotides, antibodies, apparatus, and kits disclosed herein and uses thereof, and various modifications may be made in the details within the scope and range of equivalents of the claims and without departing from the spirit of the invention.

What is claimed is:

1. An isolated polypeptide comprising the amino acid sequence of SEQ ID NO: 11.

2. The polypeptide according to claim 1, wherein said polypeptide has at least one activity of a CNGH0010 polypeptide.

3. The polypeptide of claim 2, wherein the polypeptide is glycosylated.

4. The polypeptide of claim 3, wherein the polypeptide is O-linked glycosylated.

5. A composition comprising the polypeptide of claim 1.

6. A fusion polypeptide comprising the polypeptide of claim 1 operably linked to a heterologous polypeptide.

7. The fusion polypeptide of claim 6 wherein the heterologous polypeptide is a member of the immunoglobulin protein family or a fragment of said member.

8. A device comprising the polypeptide of claim 1, wherein said device is suitable for contacting or administering said polypeptide by one or more modes selected from the group consisting of parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, and transdermal.

9. An article of manufacture for human pharmaceutical or diagnostic use, comprising packaging material and a container comprising the polypeptide of claim 1.

10. The article of manufacture of claim 9, wherein said container is a component of a parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal delivery device or system.

* * * * *